US010253052B2

(12) United States Patent
Kung et al.

(10) Patent No.: US 10,253,052 B2
(45) Date of Patent: Apr. 9, 2019

(54) HBED-BISPHOSPHONATES, RADIOMETAL CONJUGATES AND THEIR USE AS THERANOSTIC AGENTS

(71) Applicant: Five Eleven Pharma Inc., Philadelphia, PA (US)

(72) Inventors: Hank F. Kung, Springfield, PA (US); Zehui Wu, Philadelphia, PA (US); Seok Rye Choi, Aston, PA (US); Karl Plössl, Wilmington, DE (US); Zhihao Zha, Philadelphia, PA (US)

(73) Assignee: Five Eleven Pharma Inc., Philadelphia, PA (US)

( * ) Notice: Subject to any disclaimer, the term of this patent is extended or adjusted under 35 U.S.C. 154(b) by 146 days.

(21) Appl. No.: 15/203,602

(22) Filed: Jul. 6, 2016

(65) Prior Publication Data

US 2017/0022224 A1    Jan. 26, 2017

Related U.S. Application Data

(60) Provisional application No. 62/189,652, filed on Jul. 7, 2015, provisional application No. 62/320,296, filed on Apr. 8, 2016.

(51) Int. Cl.
| | |
|---|---|
| A61K 51/04 | (2006.01) |
| A61K 49/10 | (2006.01) |
| C07F 9/38 | (2006.01) |
| C07F 9/6515 | (2006.01) |
| C07F 9/6524 | (2006.01) |

(52) U.S. Cl.
CPC ........ C07F 9/3873 (2013.01); A61K 51/0489 (2013.01); A61K 51/0497 (2013.01); C07F 9/3817 (2013.01); C07F 9/6515 (2013.01); C07F 9/6524 (2013.01)

(58) Field of Classification Search
CPC combination set(s) only.
See application file for complete search history.

(56) References Cited

U.S. PATENT DOCUMENTS

| | | | |
|---|---|---|---|
| 7,161,000 B2 | 1/2007 | Higashimura et al. | |
| 2004/0242631 A1 | 12/2004 | Garlich et al. | |
| 2012/0148492 A1 | 6/2012 | Dozono | |
| 2014/0038873 A1 | 2/2014 | Herrmann et al. | |

FOREIGN PATENT DOCUMENTS

| | | |
|---|---|---|
| EP | 2867857 A1 | 4/2015 |
| WO | WO-2017007790 A9 | 1/2017 |

OTHER PUBLICATIONS

Matthias Eder et al. Tetrafluorophenolate of HBED-CC: a versatile conjugation agent for 68Ga-labeled small recombinant antibodies, Eur. J. Nucl Med Mol Imaging, 35, 1878-1886. (Year: 2008).*

M. Fellner et al., 68Ga-BPAMD: Pet-imaging of bone metastases with a generator based positron emitter, Nuclear Medicine and Biology, 39, 993-999. (Year: 2012).*

Afshar-Oromieh, A., et al., "Comparison of PET/CT and PET/MRI hybrid systems using a $^{68}$Ga-labelled PSMA ligand for the diagnosis of recurrent prostate cancer: initial experience," European Journal of Nuclear Medicine and Molecular Imaging 41(5):887-897, Springer-Verlag, Germany (2014).

Afshar-Oromieh, A., et al., "The Diagnostic Value of PET/CT Imaging with the $^{68}$Ga-Labelled PSMA ligand HBED-CC in the Diagnosis of Recurrent Prostate Cancer," European Journal of Nuclear Medicine and Molecular Imaging 42(2):197-209, Springer-Verlag, Germany (2015).

Akhtar, N.H., et al., "Prostate-specific Membrane Antigen-based Therapeutics," Advances in Urology 2012:973820, Hindawi Publishing Corporation. Egypt, 9 pages (2012).

Banerjee, S.R. and Pomper, M.G., "Clinical Applications of Gallium-68," Applied Radiation and Isotopes 76:2-13, Elsevier Ltd., England (2013).

Banerjee, S.R., et al., "$^{68}$Ga-labeled Inhibitors of Prostate-specific Membrane Antigen (PSMA) for Imaging Prostate Cancer," Journal of Medicinal Chemistry 53(14):5333-5341, American Chemical Society, United States (2010).

(Continued)

Primary Examiner — Michael G. Hartley
Assistant Examiner — Jagadishwar R Samala
(74) Attorney, Agent, or Firm — Sterne, Kessler, Goldstein & Fox P.L.L.C.

(57) ABSTRACT

The present invention relates to compounds according to Formula I or Formula II, which are potential bone imaging agents. Certain compounds labeled with $^{68}$Ga displayed excellent bone uptake and retention. The present invention also relates to pharmaceutical compositions comprising a pharmaceutical acceptable carrier and a compound of Formula I or Formula II or a pharmaceutically acceptable salt thereof.

28 Claims, 6 Drawing Sheets

(56) References Cited

OTHER PUBLICATIONS

Baur, B., et al., "Synthesis, Radiolabelling and In Vitro Characterization of the Gallium-68-,Yttrium-90- and Lutetium-177-Labelled PSMA Ligand, CHX-A"-DTPA-DUPA-Pep," Pharmaceuticals 7(5):517-529, MDPI, Switzerland (2014).

Broan, C.J., et al., "Structure and Solution Stability of Indium and Gallium Complexes of 1,4,7-Triazacyclononanetriacetate and of Yttrium Complexes of 1,4,7,10-Tetraazacyclododecanetetraacetate and Related Ligands: Kinetically Stable Complexes for Use in Imaging and Radioimmunotherapy. X-Ray Molecular Structure of the Indium and Gallium Complexes of 1,4,7-Triazacyclononane-1,4,7-triacetic Acid", Journal of the Chemical Society, Perkin Transactions II 21:87-99, Royal Society of Chemistry, England (1991).

Chakraborty, P.S., et al., "Metastatic Poorly Diffetentiated Prostate Carcinoma with Neuroendocrine Differentiation: Negative on $^{68}$-Ga-PSMA PET/CT," Clinical Nuclear Medicine 40(2):e163-e166. Wolters Kluwer Health, Inc., United States (2015).

Chappell, L.L., et al., "Synthesis and Evaluation of Novel Bifunctional Chelating Agents Based on 1,4,7,10-Tetraazacyclododecane,-N,N',N",N'''-Tetraacetic Acid for Radiolabeling Proteins," Nuclear Medicine and Biology 30(6):581-595, Elsevier Inc., United States (2003).

Clarke, E.T. and Martell, E., "Stabilities of Trivalent Metal Ion Complexes of the Tetraacetate Derivatives of 12-, 13- and 14-Membered Tetraazamacrocycles," Inorganica Chimica Acta 190:37-46. Elsevier Sequoia, Ireland (1991).

Davis, M.I., et al., "Crystal Structure of Prostate-specific membrane Antigen, a Tumor Marker and Peptidase," Proceedings of the National Academy of Science USA 102(17):5981-5986, National Academy of Sciences, United States (2005).

De Leon-Rodriguez, L.M. and Kovacs, Z., "The Synthesis and Chelation Chemistry of DOTA-Peptide Conjugates," Bioconjugate Chemistry 19(2):391-402, American Chemical Society, United States (2008).

Eder, M., et al., "$^{68}$Ga-Complex Lipophilicity and the Targeting Property of Urea-based PSMA Inhibitor for PET Imaging," Bioconjugate Chemistry 23(4):688-697, American Chemical Society, United States (2012).

Eder, M., et al., "Novel Preclinical and Radiopharmaceutical Aspects of [$^{68}$Ga]Ga-PSMA-HBED-CC: A New PET Tracer for Imaging of Prostate Cancer," Pharmaceuticals 7(7):779-796, MDPI, Switzerland (2014).

Eiber, M., et al., "$^{68}$Ga-PSMA PET/MR with Multimodality Image Analysis for Primary Prostate Cancer," Abdominal Imaging 40(6):1769-1771, Springer Science+Business Media, United States (2015).

Eiber, M., et al., "Evaluation of Hybrid $^{68}$Ga-PSMA Ligand PET/CT in 248 Patients with Biochemical Recurrence After Radical Prostatectomy," Journal of Nuclear Medicine 56(5):668-674, Society of Nuclear Medicine, United States (2015).

Eisenwiener, K.P., et al., "NODAGATOC, a New Chelator-Coupled Somatostatin Analogue Labeled with [$^{67/68}$Ga] and [$^{111}$In] for SPECT, PET, and Targeted Therapeutic Applications of Somatostatin Receptor (hsst2) Expressing Tumors," Bioconjugate Chemistry 13(3):530-541, American Chemical Society, United States (2002).

Fani, M., et al., "In Vivo Imaging of Folate Receptor Positive Tumor Xenografts using Novel $^{68}$Ga-NODAGA-Folate Conjugates," Molecular Pharmaceutics 9(5):1136-1145, American Chemical Society, United States (2012).

Fellner, M., et al., "$^{68}$Ga-BPAMD: PET-Imaging of Bone Metastases with a Generator Based Positron Emitter," Nuclear Medicine and Biology 39(7):993-999, Elsevier Inc., United States (2012).

Fellner, M., et al., "PET/CT Imaging of Osteoblastic Bone Metastses with $^{68}$Ga-Gisphosphonates: First Human Study," European Journal of Nuclear Medicine and Molecular Imaging 37(4):834, Springer-Verlag, Germany (2010).

Holub, J., et al, "Gallium(III) Complexes of NOTA-bis(phosphonate) Conjugates as PET Radiotracers for Bone Imaging," Contrast Media & Molecular Imaging 10(2):122-134, John Wiley & Sons, Ltd., United States (2015).

Huang, S.S., et al., "Improving the Biodistribution of PSMA-targeting Tracers with a Highly Negatively Charge Linker," Prostate 74(7):702-713, Wiley-Liss, United States (2014).

Huigen, Y.M., et al., "The Binding of $^{99m}$Tc(Sn)-MDP Complexes to Human Serum Albumin and Other Blood Protein Determined with Gel Chromatography and Ultrafiltration," International Journal of Radiation Applications and Instrumentation. Part A, Applied Radiation and Isotopes 40(7):629-635, Pergamon Press, England (1989).

Iagaru, A., et al., "Pilot Prospective Evaluation of $^{99m}$Tc-MDP Scintigraphy, $^{18}$F NaF PET/CT, $^{18}$F FDG PET/CT and Whole-Body MRI for Detection of Skeletal Metastases," Clinical Nuclear Medicine 38(7):e290-e296, Lippincott Williams & Wilkins, United States (2013).

Jadvar, H., et al., "Sodium $^{18}$F-fluoride PET/CT of Bone, Joint, and Other Disorders," Seminars in Nuclear Medicine 45(1):58-65, Elsevier Inc., United States (2015).

Jadvar, H., "Molecular Imaging of Prostate Cancer with PET," Journal of Nuclear Medicine 54(10):1685-1688, Society of Nuclear Medicine and Molecular Imaging, Inc., United States (2013).

Knetsch, P.A., et al., "[$^{68}$Ga]NODAGA-RGD for Imaging $\alpha_v\beta_3$ Integrin Expression," European Journal of Nuclear Medicine and Molecular Imaging 38(7):1303-1312, Springer-Verlag Berlin, Germany (2011).

Malik, N., et al., "Radiofluorination of PSMA-HBED via Al$^{18}$F$^{2+}$ Chelation and Biological Evaluations in Vitro," Molecular Imaging and Biology 17(6):777-785, World Molecular Imaging Society, United States (2015).

Manzoni, L., et al., "Synthesis of Gd and $^{68}$Ga Complexes in Conjugation with a Conformationally Optimized RGD Sequence as Potential MRI and PET Tumor-imaging Probes," ChemMedChem 7(6):1084-1093, Wiley-VCH, Germany (2012).

Maurer, T., et al., "Positron Emission Tomography/magnetic Resonance Imaging with $^{68}$Gallium-labeled Ligand of Prostate-specific Membrane Antigen: Promising Novel Option in Prostate Cancer Imaging?," International Journal of Urology 21(12):1286-1288, The Japanese Urological Association, Australia (2014).

Maurer, T., et al., "Prostate-specific Membrane Antigen-radioguided Surgery for Metastatic Lymph Nodes in Prostate Cancer," European Urology 68(3):530-534, Elsevier B.V., Netherlands (2015).

Meckel, M., et al., "In Vivo Comparison of DOTA Based $^{68}$Ga-labeled Bisphosphonates for Bone Imaging in Non-tumour Models," Nuclear Medicine and Biology 40(6):823-830, Elsevier Inc., United States (2013).

Mjos, K.D. and Orvig, C., "Metallodrugs in Medicinal Inorganic Chemistry," Chemical Reviews 114(8):4540-4563, American Chemical Society, United States (2014).

Morgat, C., et al., "Gallium-68: Chemistry and Readiolabeled Peptides Exploring Different Oncogenic Pathways," Cancer Biotheraphy & Radiopharmaceuticals 28(2):85-97, Mary Ann Liebert, Inc., United States (2013).

Motekaitis, R.J., et al., "Stability and Structure of Activated Macrocycles Ligands with Biological Applications," Inorganic Chemistry 35(13):3821-3827, American Chemical Society, United States (1996).

Nedrow, J.r., et al., "Positron Emission Tomographic Imaging of Copper 64- and Gallium 68-labeled Chelator Conjugates of the Somatostatin Agonist Tyr$^3$-Octreotate," Molecular Imaging 13:25 pages, Decker Intellectual Properties, United States (2014).

Notni, J., et al., "Phosphinic Acid Functionalized Polyazacycloalkane Chelators for Radiodiagnostics and Raiotherapeutics: Unique Characteristics and Applications," ChemMedChem 9(6):1107-1115, Wiley-VCH, Germany (2014).

Ogawa, K., et al., "Preparation and Evaluation of a Radiogallium Complex-conjugated Bisphosphonate as a Bone Scintigraphy Agent," Nuclear Medicine and Biology 38(5):631-636, Elsevier Inc., United States (2011).

Osborne, J.R., et al., "Prostate-specific Membrane Antigen-based Imaging," Urologic Oncology: Seminars and Original Investigations 31(2):144-154, Elsevier Inc., United States (2013).

Oxboel, J., et al., "Comparison of Two New Angiogenesis PET Tracers $^{68}$Ga-NODAGA-E[c(RGDyK)]$_2$ and $^{64}$Cu-NODAGA-

(56) References Cited

OTHER PUBLICATIONS

E[c(RGDyK)]$_2$; in vivo Imaging Studies in Human Xenograft Tumors," Nuclear Medicine and Biology 41(3):259-267, Elsevier Inc., United States (2014).
Pohle, K., et al., "$^{68}$Ga-NODAGA-RGD is a Suitable Substitute for $^{18}$F-Glacto-RGD and can be Produced with High Specific Activity in a cGMP/GRP Compliant Automated Process," Nuclear Medicine and Biology 39(6):777-784, Elsevier Inc., United States (2012).
Price, E.W. and Orvig, C., "Matching Chelators to Radiometals for Radiopharmaceuticals," Chemical Society Reviews 43(1):260-290, The Royal Society of Chemistry, England (2014).
Ramogida, C.F., et al., "H$_2$CHXdedpa and H$_4$CHXoctapa-Chiral Acyclic Chelating Ligands for $^{67/68}$Ga and $^{111}$In Radiopharmaceuticals," Inorganic Chemistry 54(4):2017-2031, American Chemical Society, United States (2015).
Ristau, B.T., et al., "The Prostate-specific Membrane Antigen: Lessons and Current Clinical Implications From 20 Years of Research," Urologic Oncology: Seminars and Original Investigations 32(3):272-279, Elsevier Inc., United States (2014).
Rösch, F., "Past, Present and Future of $^{68}$Ge/$^{58}$Ga Generators," Applied Radiation and Isotopes 76:24-30, Elsevier Ltd., England (2013).
Sanchez-Crespo, A., "Comparison of Gallium-68 and Fluorine-18 Imaging Characteristics in Positron Emission Tomography," Applied Radiation and Isotopes 76:55-62, Elsevier Ltd., England (2013).
Sandstrom, M., et al., "Comparative Biodistribution and Radiation Dosimetry of $^{68}$Ga-DOTATOC and $^{68}$Ga-DOTATATE in Patients with Neuroendocrine Tumors," Journal of Nuclear Medicine 54(10):1755-1759, Society of Nuclear Medicine and Molecular Imaging, Inc., United States (2013).
Schafer, M., et al., "A Dimerized Urea-based Inhibitor of the Prostate-specific Membrane Antigen for $^{68}$Ga-PET Imaging of Prostate Cancer," EJNMMI Research 2(1):23, Springer Berlin, Germany, 11 pages (2012).
Seemann, J., et al., "Cation Exchange-based Post-processing of $^{68}$Ga-eluate: A Comparison of Three Solvent Systems for Labelling of DOTATOC, NO2AP$^{SP}$ and DATA$^{111}$," Applied Radiation and Isotopes 98:54-59, Elsevier Ltd., England (2015).
Simecek, J., et al, "A Cyclen-based Tetraphosphiate Chelator for the Preparation of Radiolabeled Tetrameric Bioconjugates," Chemistry A European Journal 19(24):7748-7757, Wiley-VCH, Germany (2013).
Simecek, J., et al., "Benefits of NOPO as Chelator in Gallium-68 Peptides, Exemplified by Preclinical Characterization of $^{68}$Ga-NOPO-c(RGDfK)," Molecular Pharmaceutics 11(5):1687-1695, American Chemical Society, United States (2014).
Simecek, J., et al., "How is $^{68}$Ga Labeling of Macrocyclic Chelators Influenced by Metal Ion Contaminants in $^{68}$Ge/$^{68}$Ga Generator Eluates?" ChemMedChem 8(1):95-103, Wiley-VCH, Germany (2013).
Simecek, J., et al., "Tailored Ballium(III) Chelator NOPO: Synthesis, Characterization, Bioconjugation, and Applications in Preclinical Ga—68-PET Imaging," Molecular Pharmaceutics 11(11):3893-3903, American Chemical Society, United States (2014).
Smith, D.L., et al., "The Untapped Potential of Gallium 68-PET: The Next Wave of $^{68}$Ga-agents," Applied Radiation and Isotopes 76:14-23, Elsevier Ltd., England (2013).

Stasiuk, G.J. and Long, N.J., "The Ubiquitous DOTA and its Derivatives: The Impact of 1,4,7,10-tetraazacyclododecane-1,4,7,10-tetraacetic Acid on Biomedical Imaging," Chemical Communications 49(27):2732-2746, Royal Society of Chemistry, England (2013).
Sun, Y., et al., "Indium(III) and Gallium(III) Complexes of Bis(aminoethanethiol) Ligands with Different Denticities: Stabilites, Molecular Modeling, and in Vivo Behavior," Journal of Medicinal Chemistry 39(2):458-470, American Chemical Society, United States (1996).
Suzuki, K., et al., "Synthesis and Evaluation of Novel $^{68}$Ga-chelate-conjugated Bisphosphonate as a Bone-seeking Agent for PET Imaging," Nuclear Medicine and Biology 38(7):1011-1018, Elsevier Inc., United States (2011).
Toegel, S., et al., "Preparation and pre-vivo evaluation of no-carrier-added, carrier-added and cross-complexed [$^{68}$Ga]-EDTMP formulations," European Journal of Pharmaceutics and Biopharmaceutics 68(2):406-412, Elsevier B.V., Netherlands (2008).
Velikyan, I., "Continued Rapid Growth in $^{68}$Ga Applications: Update 2013 to Jun. 2014," Journal of Labelled Compounds & Radiopharmaceuticals 58(3):99-121, John Wiley & Sons, Ltd., England (2015).
Velikyan, I., et al., "Convenient Preparation of $^{68}$Ga-based PET-radiopharmaceuticals at Room Temperature," Bioconjugate Chemistry 19(2):569-573, American Chemical Society, United States (2008).
Velikyan, I., "Prospective of $^{68}$Ga-Radiopharmaceutical Development," Theranostics 4(1):47-80, Ivyspring International, Australia (2014).
Velikyan, I., et al., "Quantitative and Qualitative Intrapatient Comparison of $^{68}$Ga-DOTATOC and $^{68}$Ga-DOTATATE: Net Uptake for Accurate Quantification," Journal of Nuclear Medicine 55(2):204-210, Society of Nuclear Medicine, United States (2014).
Velikyan, I., "The Diversity of $^{68}$Ga-based Imaging Agents," Recent Results in Cancer Research 194:101-131, Springer-Verlag, Germany (2013).
Uehara, T., et al., "Assessment of $^{188}$Re chelate-conjugated bisphosphonate for the development of new radiopharmaceuticals for bones," Nuclear Medicine and Biology 34(1):79-87, Elsevier Inc., United States (2007).
International Search Report and Written Opinion for International Application No. PCT/US16/41040, United States Patent Office, Virginia, dated Sep. 22, 2016, 7 pages.
International Preliminary Report on Patentability for International Application No. PCT/US16/41040, International Bureau of WIPO, dated Jan. 9, 2018, 5 pages.
Segall, G., et al., "SNM practice Guideline for Sodium 18F-Flouride PET/CT Bone Scans 1.0," The Journal of Nuclear Medicine 51(11):1813-1820, Society of Nuclear Medicine and Molecular Imaging, United States (2010).
Passah, A., et al., "Evaluation of Bone-seeking novel radiotracer 68Ga—NO2AP-Bisphosphonate for the detection of skeletal metastases in carcinoma breast," Eur J Nucl Med Mol Imaging 44:41-49, Springer, United States (2017).

\* cited by examiner

HBED-BISPHOSPHONATES, RADIOMETAL CONJUGATES AND THEIR USE AS THERANOSTIC AGENTS

BACKGROUND OF THE INVENTION

[$^{99m}$Tc]-methylene disphosphonate (MDP) planar or single-photon emission computerized tomography (SPECT) bone imaging is one of the most commonly performed nuclear medicine procedures to evaluate bone disorders, such as infection (osteomyelitis), noninfectious inflammation (arthritis), trauma, metabolic bone disease, benign and malignant neoplasms, and metastasis. Nevertheless, concerns are expressed about recurring shortages of $^{99m}$Tc, which may limit the availability of this imaging agent for routine clinical use. Recently, [$^{18}$F]NaF in conjunction with PET has been approved for the clinical evaluation of patients with known or suspected bone metastases. Iagaru A, et al., *Clin. Nucl. Med.* 38:e290-6 (2013); Jadvar H, et al., *Semin. Nucl. Med.* 45:58-65 (2015). There is currently an increasing number of regional commercial distribution centers for PET radiotracers, thus improving the availability of [$^{18}$F]NaF ($t_{1/2}$ 110 min, 97% $\beta^+$, 0.63 MeV max energy) for routine clinical practice.

$^{68}$Ge/$^{68}$Ga generators for PET imaging are becoming increasingly available in nuclear medicine clinics. Velikyan I., *J. Label. Compd. Radiopharm.* DOI: 10.1002/jlcr.3250 (published online Feb. 17, 2015). There are several advantages associated with using $^{68}$Ga: 1) A long-lived parent isotope, germanium-68 ($^{68}$Ge) ($t_{1/2}$ 271 d), allows for an easy and widespread generator distribution; 2) The physical properties of $^{68}$Ga ($t_{1/2}$ 68 min, 89% $\beta^+$, 1.90 MeV max energy) are highly suitable for PET imaging; 3) $^{68}$Ge/$^{68}$Ga generators provide a convenient mechanism for position emitting isotope production without the need for a nearby cyclotron. An important factor to consider is that the emitting $\beta^+$ energy for $^{18}$F and $^{68}$Ga is 0.63 MeV and 1.90 MeV, respectively. However, despite the difference in the $\beta^+$ energy, $^{18}$F and $^{68}$Ga radiopharmaceuticals exhibit similar spatial resolution, sensitivity, image contrast, and activity recovery coefficients in human tissue, and they produce comparable clinical images in humans.

Due to the relatively short physical half-life of $^{68}$Ga and its potential for binding to the blood component transferrin, several essential properties for $^{68}$Ga radiopharmaceuticals are needed: 1) The $^{68}$Ga complexes should display high in vitro stability; 2) The formation of $^{68}$Ga complexes should be kinetically fast; 3) $^{68}$Ga complexes should be able to form bifunctional molecules for targeting, pre-conjugation, to biologically active molecules; and 4) $^{68}$Ga complexes should display suitable in vivo stability in blood circulation with minimal transferrin exchange.

Currently, the most common $^{68}$Ga labeled radiopharmaceuticals evaluated are [$^{68}$Ga]DOTATOC, [$^{68}$Ga]DOTATATE, and [$^{68}$Ga]DOTANOC. These compounds are mainly used for detecting the over-expression of somatostatin receptors associated with neuroendocrine tumors. This has attracted significant attention for using PET imaging in the diagnosis of neuroendocrine tumor and various diseases. Morgat C. et al., Gallium-68: chemistry and radiolabeled peptides exploring different oncogenic pathways, *Cancer Biother. Radiopharm.* 28:85-97 (2013); Sandstrom M, et al. *J. Nucl. Med.* 54:1755-9 (2013); Velikyan I, et al., Quantitative and qualitative intrapatient comparison of 68Ga-DOTATOC and 68Ga-DOTATATE: net uptake rate for accurate quantification, *J. Nucl. Med.* 55:204-10 (2014).

A number of Ga complexes have been reported, and they are usually macrocyclic or acyclic polyaza carboxylic acids. These complexes often include metal-chelating ligands designed to form gadolinium (Gd) complexes for use as magnetic resonance imaging (MIRI) contrast agents, such as: diethylenetriaminepentaacetic acid (DTPA), 1,4,7,10-tetraazacyclododecane-1,4,7,10-tetraacetic acid (DOTA), 1,4,7-triazacyclononane-1,4,7-triacetic acid (NOTA), and related derivatives (Table 1). Many of these ligands are commonly employed to chelate radioactive metal ions. These include single photon emitting isotopes for SPECT imaging—$^{67}$Ga, $^{99m}$Tc, and $^{111}$In, as well as positron emitting isotopes for PET imaging—$^{64}$Cu, $^{86}$Y, $^{89}$Zr, $^{68}$Ga, and $^{89}$Sr. Literature reports on polyaza carboxylic acids such as DOTA and related ligands, suggest that they form highly thermodynamic stable complexes with Ga(III). Nevertheless, the complexation of no-carrier-added (n.c.a.) $^{68}$Ga with DOTA derivatives has been shown to be inefficient, often requiring heating of 80-100° C. The formation of DOTA ligands with Ga(III) is more sensitive to experimental conditions than that of NOTA analogs. It is likely that the smaller cavity created by the NOTA derivatives fits tighter to the ionic radius of Ga(III). NOTA derivatives, especially 1-(1,3-carboxypropyl)-4,7-carboxymethyl-1,4,7-triazacyclononane (NODAGA), were shown to be more suitable for chelating the Ga(III) ion than DOTA derivatives. Price E. W. and Orvig C., *Chem. Soc. Rev.* 43:260-90 (2014); Oxboel J., et al., *Nucl. Med. Biol.* 41:259-67 (2014). The Ga(III) NODAGA complexes exhibited much higher thermodynamic stability as well as rapid complex kinetics. As Ga(III) is a small ion and generally requires an octahedral coordination sphere, Ga(III)NODAGA analogs provide optimal in vitro and in vivo stability. There are several reports in which Ga(III)NODAGA was preferentially chosen as the chelating group in producing bifunctional imaging agents. By using DOTA and NOTA derivatives, many $^{68}$Ga labeled bisphosphonates were prepared and tested for bone imaging. It was reported that a bisphosphonate DOTA derivative, [$^{68}$Ga] 4-{[(bis-phosphonomethyl) carbomoyl]methyl}-7,10-bis-(carboxy-methyl)-1,4,7,10-tetraazacyclododec-1-yl)-acetic acid (BPAMD), displayed good bone uptake and retention in humans. Fellner M., et al., *Eur. J. Nucl. Med. Mol. Imaging* 37:834 (2010).

Table 1, depicts the structures of bisphosphonates that are reported to be capable of complexing $^{68}$Ga for bone imaging. These include ethylene-diamino-N,N,N',N'-tetrakis-methylene-phosphoric acid (EDTMP), (4-{[(bis-phosphonomethyl)carbomoyl]methyl}-7,10-bis-(carboxy-methyl)-1,4,7,10-tetraazacyclododec-1-yl)-acetic acid (BPAMD), (4-{[(bis-phosphonopropyl)carbomoyl]methyl}-7,10-bis-(carboxymethyl)-1,4,7,10-tetraazacyclododec-1-yl)-acetic acid (BPAPD), tetraethyl-10-{[(2,2-bis-phosphonoethyl)-hydroxyl phosphoryl]methyl}-1,4,7,10-tetraazacyclododecane-1,4,7-triacetic acid (BPPED or DO3ABP)), (4-{[(bis-phosphonopropyl)carbomoyl]hydroxylmethyl}-1,4,7,10-tetraazacyclododecane-1,4,7,10-tetraacetic acid (DOTA-BP), 2,2'-(7-(((2,2-diphosphonoethyl)(hydroxy)phosphoryl)methyl)-1,4,7-triazo-nane-1,4-diyl)diacetic acid (NO2APBP), 4-{[(bis-phosphonopropyl) carbomoyl]methyl}-1,4,7-triaza cyclonone-1,4-diacetic acid (NOTAMBP), 1,4,7-triazacyclononane-N,Nne-1,tris(bis-phosphonopropyl) carbomoyl]methyl-methylenephosphonic) acid (TRAP(NOTP)), and 1,4,7-triazacyclononane-1,4,7-tri[methylene phosphinic acid] (TRAP(MDP)$_3$). The DOTA and NOTA based bisphosphonates, $^{68}$Ga labeled BPAMD and NO2APBP, have been successfully tested in humans as bone-imaging agents.

TABLE 1
Bisphosphonates that Can Complex $^{68}$Ga for Bone Imaging
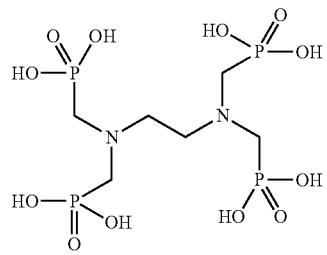
EDTMP
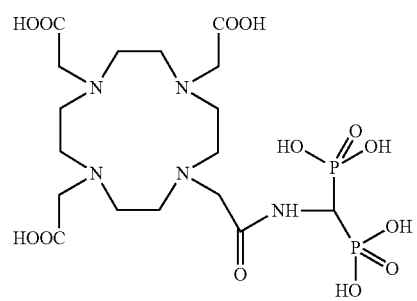
BPAMD
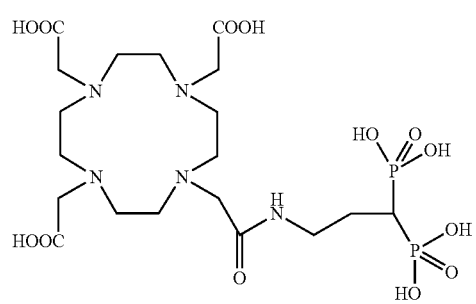
BPAPD
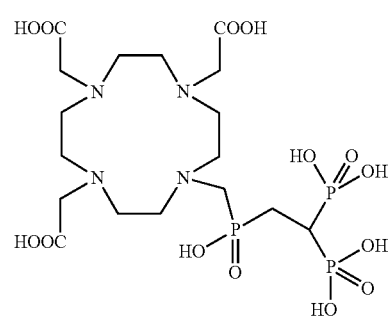
BPPED
DO3ABP TABLE 1-continued Bisphosphonates that Can Complex $^{68}$Ga for Bone Imaging

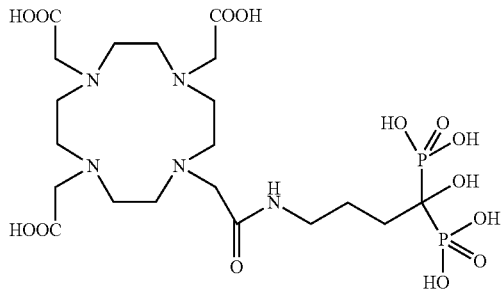
DOTA-BP

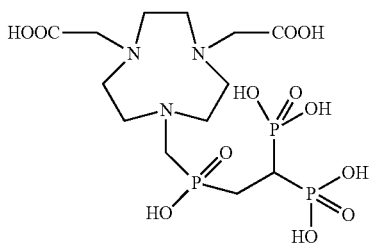
NO2AP$^{BP}$

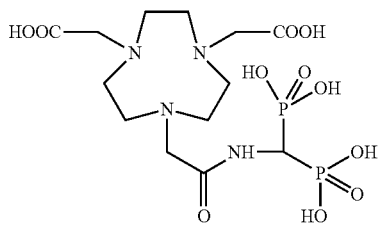
NOTAMBP

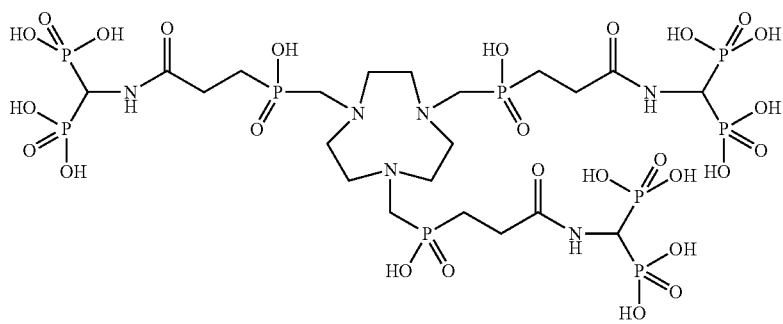
TRAP(MDP)$_3$

Several chelating groups reported for complexing Ga(III) are: DOTA, 1,4,7-triazacyclononane-1,4-bis[methylene(hydroxymethyl)phosphinic acid]-7-[methylene(2-carboxyethyl)phosphinic acid] (TRAP (NOPO)), cyclohexyl-1,2-[[6-carboxy-pyridin-2-yl]-methyl amino] ethane (H$_2$CHX DEDPA), and (5S,8S,22S,26S)-1-amino-5,8-dibenzyl-4,7,10,19,24-pentaoxo-3,6,9,18,23,25-hexaazaoctacosane-22,26,28-tri-carboxylic acid trifluoroacetate (CHX-A"-DTPA-DUPA-Pep). See Simecek J., et al., *Chem. Med. Chem.* 8:95-103 (2013); Ramogida C. F., et al., *Inorg. Chem.* 54:2017-31 (2015); Baur B., et al., *Pharmaceuticals (Basel)* 7:517-29 (2014).

Prostate-specific membrane antigen (PSMA) is a highly specific prostate epithelial cell membrane antigen. Many reports suggest that PSMA is highly expressed in various tumors, including prostate cancer. Often, PSMA expression increases in higher-grade cancers and metastatic diseases. In a majority of neovasculature in solid tumors, there is high expression of PSMA, but not in normal vasculature. This makes PSMA a suitable target for cancer detection and therapy. Certain Ga-prostate specific membrane antigen (PSMA) tagged complexes showed high-affinity binding and effective targeting of PSMA-expressing tumor models in vitro. Two studied agents for imaging PSMA binding sites in cancer patients are [$^{68}$Ga]Glu-NH—CO—NH-Lys(Ahx)-HBED-CC (monomer), and its related dimer, [$^{68}$Ga](Glu-NH—CO—NH-Lys(Ahx))$_2$-HBED-CC. Both complexes were prepared and were reported to show high PSMA binding as seen in Table 2. Baur B., et al., *Pharmaceuticals (Basel)* 7:517-29 (2014); Schafer M., et al., *EJNMMI Res* 2:23 (2012); Eder M., et al., *Pharmaceuticals (Basel)* 7:779-96 (2014); Eder M., et al., *Bioconjug. Chem.* 23:688-97 (2012). Although both [$^{68}$Ga]Glu-NH—CO—NH-Lys(Ahx)-HBED-CC (monomer) and [$^{68}$Ga](Glu-NH—CO—NH-Lys(Ahx))$_2$-HBED-CC (dimer) exhibited comparable preclinical data, the current PSMA/PET imaging agent of choice for human study is the monomer. It is generally accepted that Glu-NH—CO—NH-Lys(Ahx)-provides high binding affinity to the PSMA receptors on the cell membrane of tumors.

TABLE 2

Proposed structures of PSMA targeting imaging agents [$^{68}$Ga]Glu-NH—CO—NH-Lys(Ahx)-HBED-CC (monomer) and [$^{68}$Ga](Glu-NH—CO—NH-Lys(Ahx))$_2$-HBED-CC (dimer).

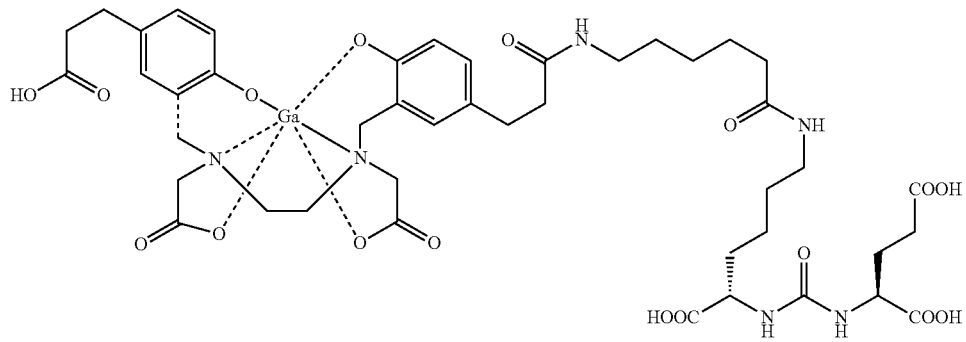

[$^{68}$Ga](Glu-NH—CO—NH—Lys(Ahx))-HBED-CC
Monomer

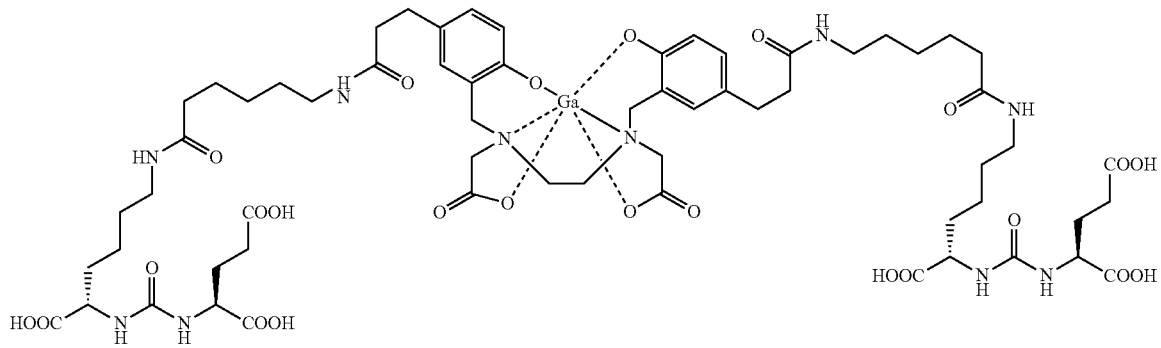

[$^{68}$Ga](Glu-NH—CO—NH—Lys(Ahx))$_2$-HBED-CC
Dimer

Most clinical studies to date have been performed with [$^{68}$Ga]Glu-NH—CO—NH-Lys(Ahx)-HBED-CC (monomer). Using HBED instead of commonly employed DOTA and NOTA, as a ligand for chelating Ga(III) has certain advantages. Stability constants (log Kd) for Ga(III)-DOTA and Ga(III)—NOTA complexes were previously reported (log Kd=21.3 and 31.0, respectively). Compared to DOTA and NOTA, the HBED chelating group forms a stronger, more stable Ga(III) complex: a log Kd value of 38.5 was reported for Ga(III)-HBED-CC.

A need continues to exist for bone imaging agents that employ available radionuclides, form complexes quickly, are stable in vitro and in vivo, and do not rapidly transfer radionuclide to transferrin in the bloodstream.

BRIEF SUMMARY OF THE INVENTION

One aspect of the invention is to novel bisphosphonate derivatives of HBEB CC and complexes thereof with metal radionuclides.

In one embodiment, the disclosure relates to a compound according to Formula I:

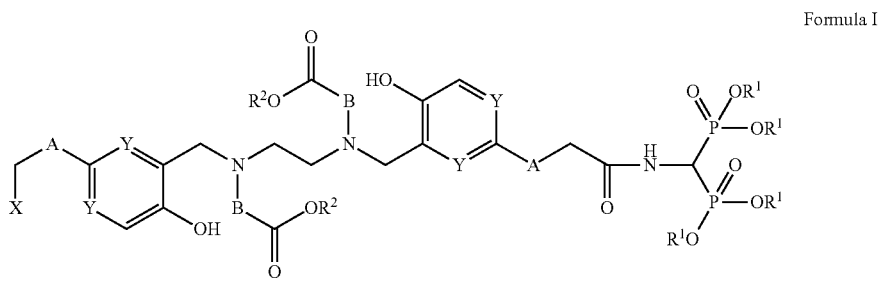

Formula I or a pharmaceutically acceptable salt thereof, wherein

A is a divalent linking moiety comprising 1 to 10 carbon atoms in a chain, a ring, or a combination thereof, wherein at least one carbon atom is optionally replaced with O, —$NR^9$—, or —C(O)—;

B is $CR^3R^4$;

X is selected from the group consisting of:

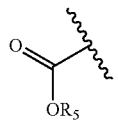

$X_1$

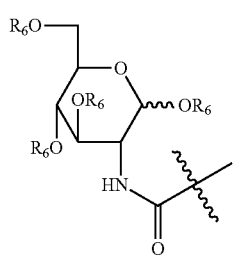

$X_2$

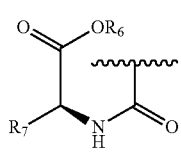

$X_3$

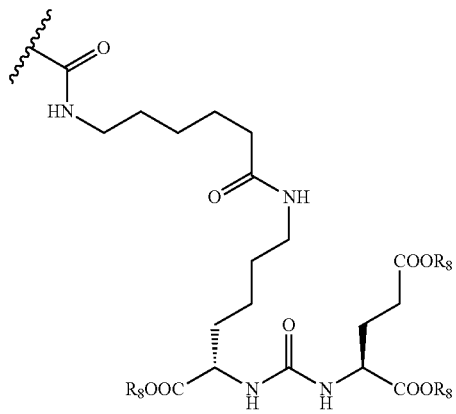

$X_4$

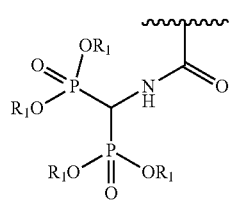

$X_5$

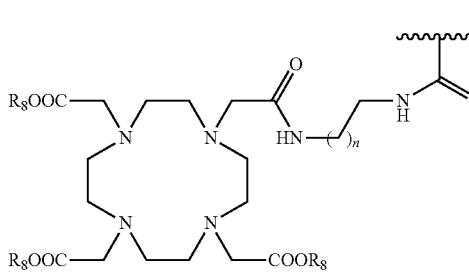

$X_6$ n is from 1 to 8;

Y is independently CH or N;

$R^1$ is hydrogen or a ($C_1$-$C_6$)alkyl group;

$R^2$, $R^5$, and $R^8$ are independently hydrogen or a carboxylic acid protecting group;

R³ and R⁴ are independently hydrogen, a $(C_1-C_{10})$alkyl group, an ethylene glycolyl group, or a propylene glycolyl group;

R⁶ is hydrogen or a $(C_1-C_6)$ acyl group; and

R⁷ is the α-position substituent of a naturally occurring or non-naturally occurring amino acid, and R⁹ is independently selected from the group consisting of H, alkyl, cycloalkyl, heterocycloalkyl, aryl, alkylaryl, arylalkyl and heteroaryl.

In another embodiment, the disclosure relates to a complex between a compound of Formula I and a metal M, wherein M is selected from the group consisting of ⁴⁴Sc, ⁴⁷Sc, ²⁰³Pb, ⁶⁷Ga, ⁶⁸Ga, ⁷²As, ¹¹¹In, ⁹⁰Y, ⁹⁷Ru, ⁶²Cu, ⁶⁴Cu, ⁵²Fe, ⁵²Mn, ¹⁴La, ¹⁷⁵Yb, ¹⁵³Sm, ¹⁶⁶Ho, ¹⁴⁹Pm, ¹⁷⁷Lu, ¹⁴²Pr, ¹⁵⁹Gd, ²¹³Bi, ⁶⁷Cu, ¹¹¹Ag, ¹⁹⁹Au, ¹⁶¹Tb, and ⁵¹Cr.

In another embodiment, the disclosure relates to a compound according to Formula II:

Formula II

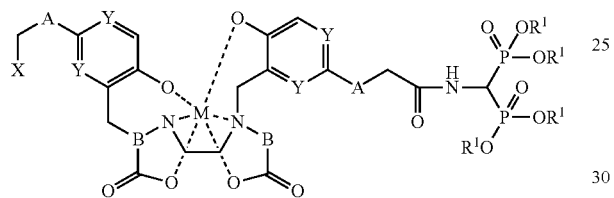

or a pharmaceutically acceptable salt thereof, wherein

A is a divalent linking moiety comprising 1 to 10 carbon atoms in a chain, a ring, or a combination thereof, wherein at least one carbon atom is optionally replaced with O, —NR⁹—, or —C(O)—;

B is CR³R⁴;

X is selected from the group consisting of:

X₁

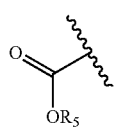

X₂

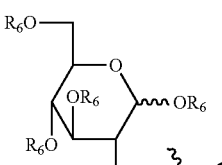

X₃

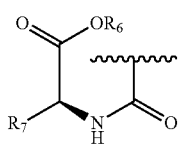

X₄

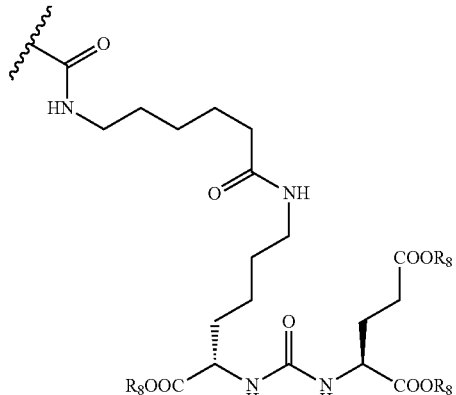

X₅

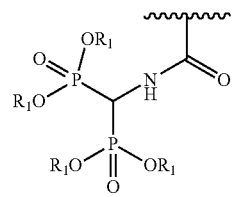

X₆

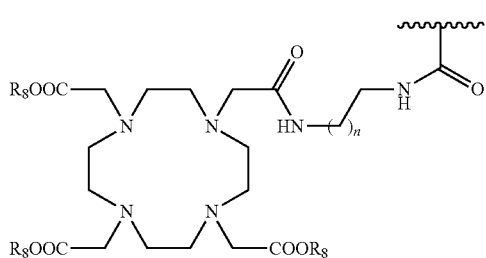

where n is from 1 to 8;

Y is independently CH or N;

R¹ is hydrogen or a $(C_1-C_6)$alkyl group;

R³ and R⁴ are independently hydrogen, a $(C_1-C_{10})$alkyl group, an ethylene glycolyl group, or a propylene glycolyl group;

R⁵, and R⁸ are independently hydrogen or a carboxylic acid protecting group;

R⁶ is a $(C_1-C_6)$ acyl group;

R⁷ is the α-position substituent of a naturally occurring or non-naturally occurring amino acid;

R⁹ is independently selected from the group consisting of H, alkyl, cycloalkyl, heterocycloalkyl, aryl, alkylaryl, arylalkyl and heteroaryl; and M is a metal selected from the group consisting of ⁴⁴Sc, ⁴⁷Sc, ²⁰³Pb, ⁶⁷Ga, ⁶⁸Ga, ⁷²As, ¹¹¹In, ⁹⁰Y, ⁹⁷Ru, ⁶²Cu, ⁶⁴Cu, ⁵²Fe, ⁵²ᵐMn, ¹⁴⁰La, ¹⁷⁵Yb, ¹⁵³Sm, ¹⁶⁶Ho, ¹⁴⁹Pm, ¹⁷⁷Lu, ¹⁴²Pr, ¹⁵⁹Gd, ²¹³Bi, ⁶⁷Cu, ¹¹¹Ag, ¹⁹⁹Au, ¹⁶¹Tb, and ⁵¹Cr.

In another embodiment, the disclosure relates to a complex between a compound of Formula I, wherein X is X6, and a metal M. In one embodiment, M is ⁴⁴Sc, ⁴⁷Sc, ⁹⁰Y, ⁹⁷Ru, and ¹⁷⁷Lu; the remaining groups are as defined for Formula I, wherein the radio metal is complexed at the X6 (DOTA) moiety.

Another embodiment of the present disclosure relates to methods of forming a radiolabeled complex of a compound of Formula I.

Another embodiment of the present disclosure relates to a method of detecting by administering to a subject a radiolabeled complex of a compound of Formula I or administering to a subject a complex of Formula II, and thereafter imaging said subject or a portion of said subject.

Another embodiment of the present disclosure relates to methods of treating bone tumors in a subject by administering a radiolabeled complex of a compound of Formula I to said subject, wherein M is $^{44}$Sc, $^{47}$Sc, $^{90}$Y, $^{97}$Ru, and $^{177}$Lu.

BRIEF DESCRIPTION OF THE FIGURES

FIG. 3A-FIG. 3C depict transaxial, coronal, and sagittal sections of microPET images of a normal mouse at 60 min post iv injection of [$^{68}$Ga]1a.

FIG. 6A-6C and FIG. 6D-6F use two different color scales at different anatomical locations to illustrate the dual targeting nature of [$^{68}$Ga]1g.

DETAILED DESCRIPTION OF THE INVENTION

Figure 1A:
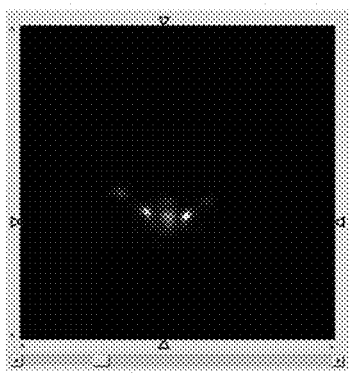
FIG. 1A-FIG. 1C depict transaxial, coronal, and sagittal sections of microPET images of a normal mouse at 60 min post iv injection of [$^{18}$F]NaF.
Figure 1B:
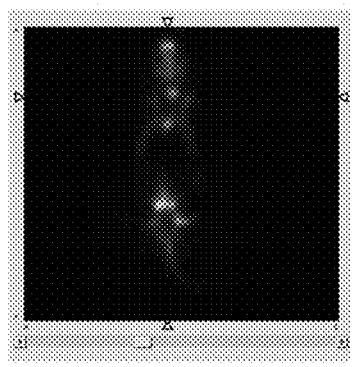
Figure 1C:
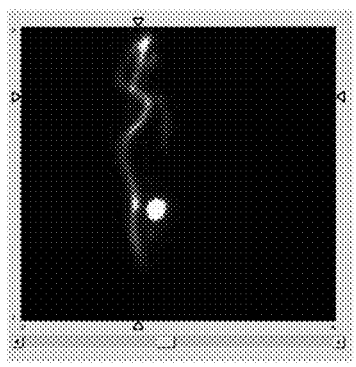
Figure 2A:
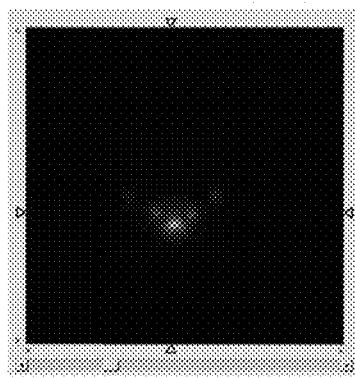
FIG. 2A-FIG. 2C depict transaxial, coronal, and sagittal sections of microPET images of a normal mouse at 60 min post iv injection of [$^{68}$Ga]BPAMD.
Figure 2B:
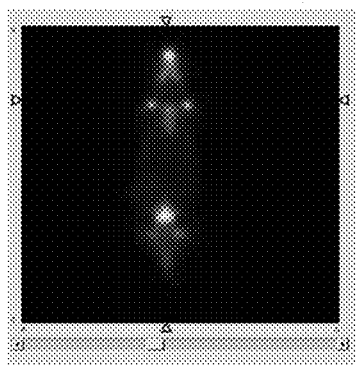
Figure 2C:
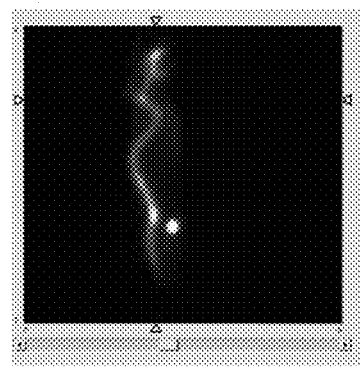
Figure 3A:
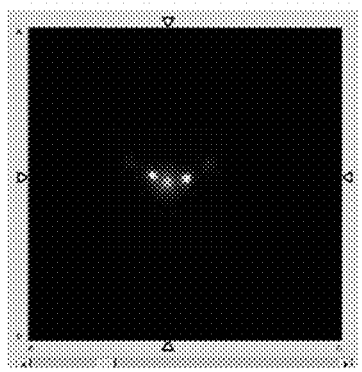
Figure 3B:
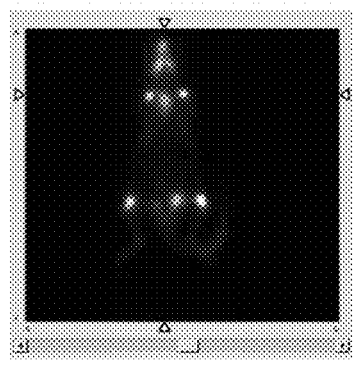
Figure 3C:
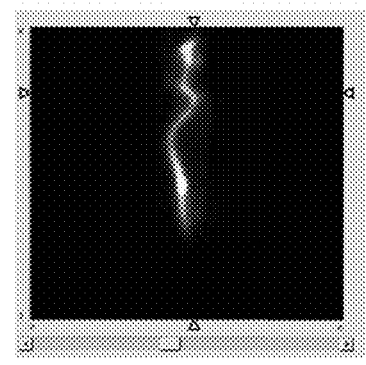

Positron emission tomography (PET) imaging using radio labeled bisphosphonates, for example 68Ga, to target bone metastasis can be a valuable tool for cancer diagnosis and for monitoring therapeutic treatment. A series of 68Ga labeled N,N'-bis[2-hydroxy-5-(carboxyethyl)benzyl]ethylenediamine-N,N'-diacetic acid (HBED-CC) compounds containing one bisphosphonate group (1a) or two bisphosphonate groups (2 and 3), were prepared (Table 3). Additional bisphosphonate-HBED-CC containing compounds including conjugated 2-glucosamine (1b), glycine (1c), alanine (1d), aspartic acid (1e), glutamic acid (1f), Glu-NH—CO—NH-Lys(Ahx) (1g) and DOTA (1h) were also prepared. The new HBED ligands, 1a-h, 2, and 3, reacted rapidly in a sodium acetate buffer with [$^{68}$Ga]GaCl$_3$ eluted from a commercially available $^{68}$Ge/$^{68}$Ga generator (pH 4, >95% labeling at room temperature in 5 min) to form [$^{68}$Ga]1a-h, [$^{68}$Ga]2, and [$^{68}$Ga]3, respectively. This labeling condition avoids the need for further purification. The biodistribution of [$^{68}$Ga]1a-h and [$^{68}$Ga]2 in normal mice after an i.v. injection showed excellent bone uptake and retention comparable to that of [$^{18}$F]NaF. However, [$^{68}$Ga]3 displayed high liver uptake and less bone localization, therefore it was not studied any further. The results suggest that [68Ga]1a-h and [$^{68}$Ga]2 are suitable as bone imaging agents in humans, serving as alternatives to the current bone imaging agent of choice, [$^{18}$F]NaF. Compounds of the invention provide practical in vivo bone imaging agents in conjunction with PET without the need of a near-by cyclotron.

Disclosed are a group of HBED-CC compounds containing bisphosphonates [68Ga]1a-h, [68Ga]2 and [68Ga]3 were prepared and tested. This series of new compounds, therefore, contains two independent components. First, the HBED chelating group forms a stable complex with 68Ga (III); second, the bisphosphonate group attached at the end of the chelating group is utilized for targeting and binding to hydroxyapatites on active bone surfaces, similar to the phosphonate group of [99mTc]MDP.

TABLE 3

Chemical structures of $^{68}$Ga labeled HBED-CC derivatives containing bisphosphonates, [$^{68}$Ga]1a-h, [$^{68}$Ga]2, and [$^{68}$Ga]3, and a known bone imaging agent, [$^{68}$Ga]BPAMD

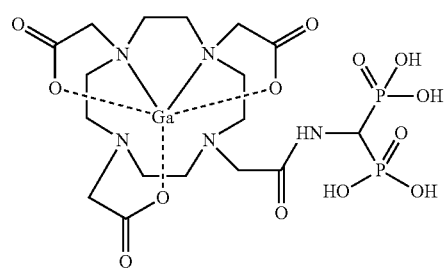

[$^{68}$Ga]BPAMD

TABLE 3-continued
Chemical structures of $^{68}$Ga labeled HBED-CC derivatives containing bisphosphonates,
[$^{68}$Ga]1a-h, [$^{68}$Ga]2, and [$^{68}$Ga]3, and a known bone imaging agent, [$^{68}$Ga]BPAMD
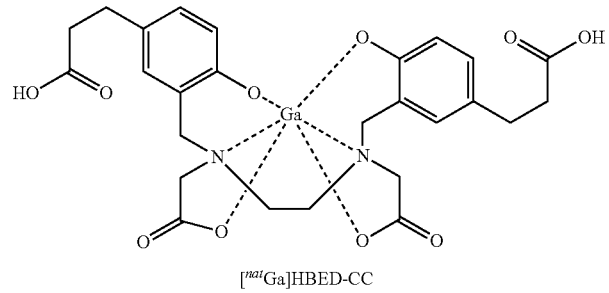
[[nat]Ga]HBED-CC
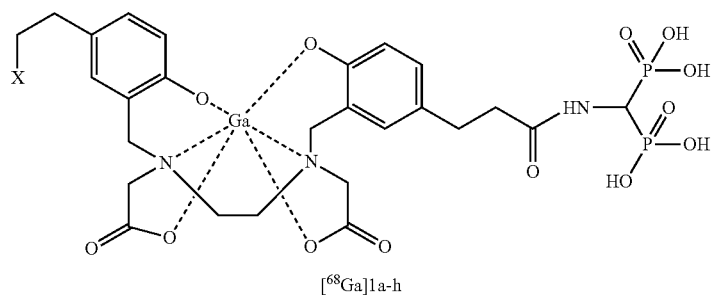
[$^{68}$Ga]1a-h
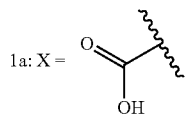
1a: X =
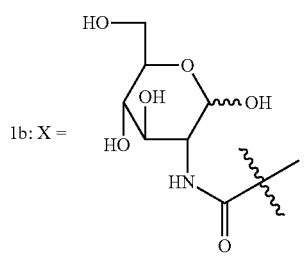
1b: X =
1c: R = H
1d: R = $CH_3$
1e: R = $CH_2COOH$
1f: R = $(CH_2)_2COOH$
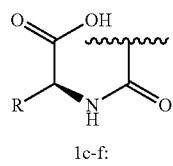
1c-f:

TABLE 3-continued
Chemical structures of $^{68}$Ga labeled HBED-CC derivatives containing bisphosphonates, [$^{68}$Ga]1a-h, [$^{68}$Ga]2, and [$^{68}$Ga]3, and a known bone imaging agent, [$^{68}$Ga]BPAMD
1g: X =
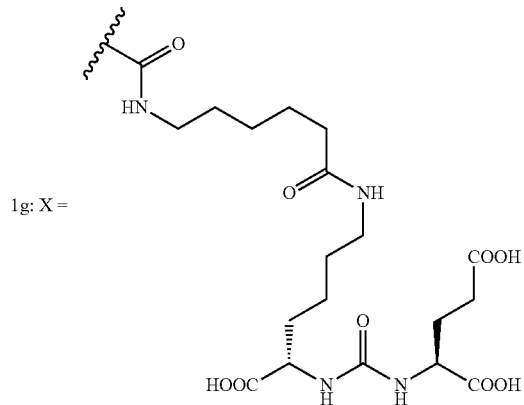 [SMILES: *C(=O)NCCCCCC(=O)NCCCC[C@H](NC(=O)N[C@@H](CCC(=O)O)C(=O)O)C(=O)O]
1h: X =
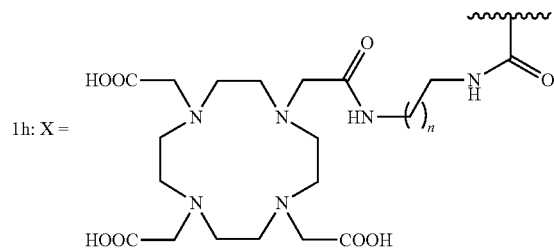
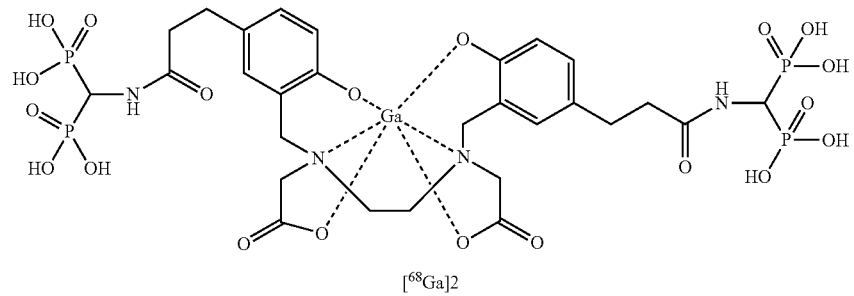
[$^{68}$Ga]2
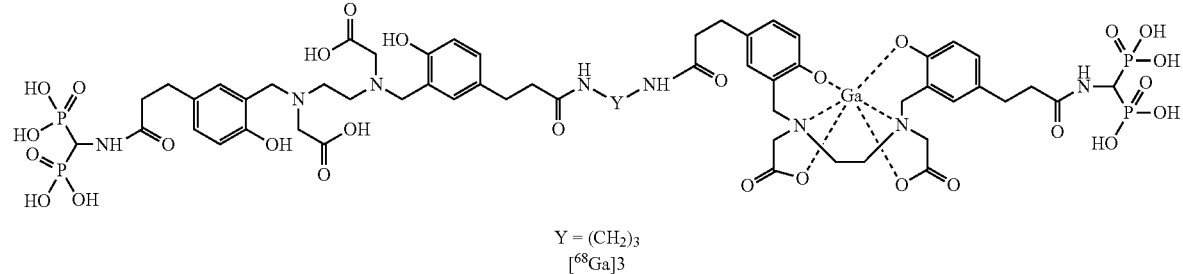
Y = (CH$_2$)$_3$
[$^{68}$Ga]3

In one embodiment, the disclosure relates to a compound according to Formula I:

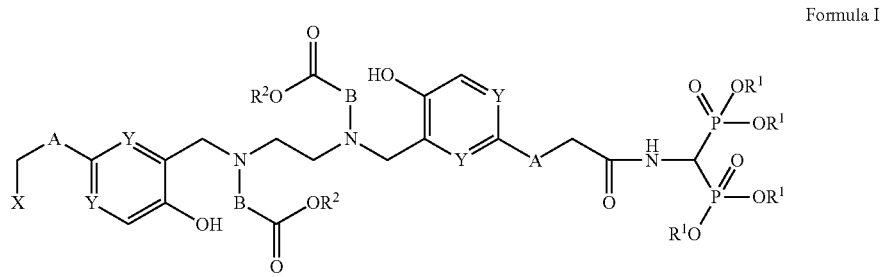

Formula I or a pharmaceutically acceptable salt thereof, wherein

A is a divalent linking moiety comprising 1 to 10 carbon atoms in a chain, a ring, or a combination thereof, wherein at least one carbon atom is optionally replaced with O, —$NR^9$—, or —C(O)—;

B is $CR^3R^4$;

X is selected from the group consisting of:

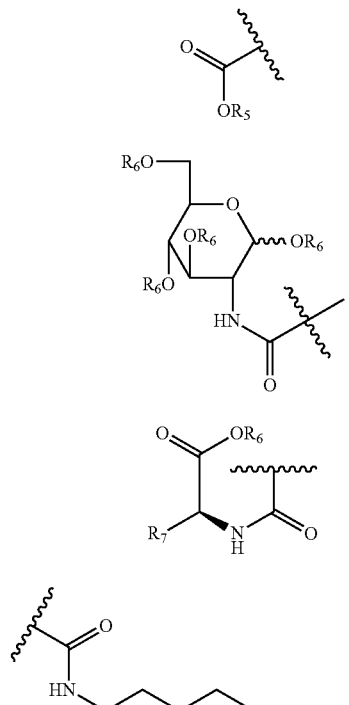

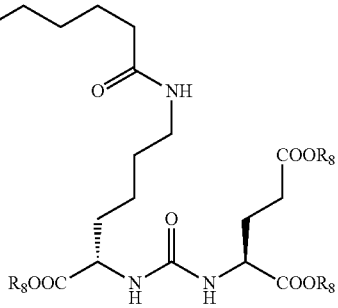

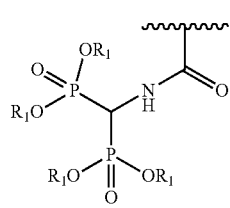

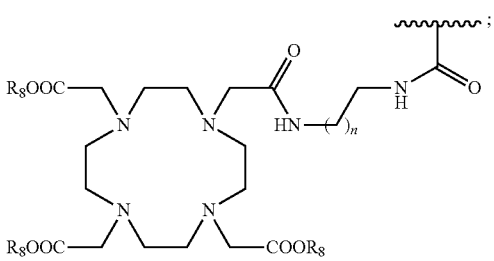

n is from 1 to 8;

Y is independently CH or N;

$R^1$ is hydrogen or a ($C_1$-$C_6$) alkyl group;

$R^2$, $R^5$, and $R^8$ are independently hydrogen or a carboxylic acid protecting group;

$R^3$ and $R^4$ are independently hydrogen, a ($C_1$-$C_{10}$) alkyl group, an ethylene glycolyl group, or a propylene glycolyl group;

$R^6$ is hydrogen or a ($C_1$-$C_6$) acyl group; and $R^7$ is the α-position substituent of a naturally occurring or non-naturally occurring amino acid, and $R^9$ is independently selected from the group consisting of H, alkyl, cycloalkyl, heterocycloalkyl, aryl, alkylaryl, arylalkyl and heteroaryl. In one embodiment $R^9$ is H, alkyl, cycloalkyl, heterocycloalkyl, aryl, alkyl aryl and heteroaryl. In another embodiment, $R^9$ is H, alkyl or arylalkyl.

In one aspect, X is one of $X_1$, $X_2$, $X_3$, $X_4$ or $X_5$.

In another aspect, X is $X_6$. In one aspect, n is 1.

In another embodiment, the disclosure relates to a complex between a compound of Formula I and a metal M, wherein M is selected from the group consisting of $^{44}$Sc, $^{47}$Sc, $^{203}$Pb, $^{67}$Ga, $^{68}$Ga, $^{72}$As, $^{111}$In, $^{90}$Y, $^{97}$Ru, $^{62}$Cu, $^{64}$Cu, $^{52}$Fe, $^{52m}$Mn, $^{140}$La, $^{175}$Yb, $^{153}$Sm, $^{166}$Ho, $^{149}$Pm, $^{177}$Lu, $^{142}$Pr, $^{159}$Gd, $^{213}$Bi, $^{67}$Cu, $^{111}$Ag, $^{199}$Au, $^{161}$Tb, and $^{51}$Cr.

In another embodiment, the disclosure relates to a compound according to Formula II:

Formula II

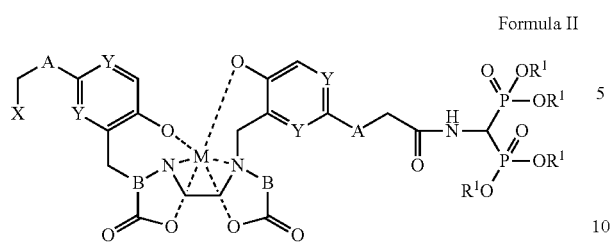

or a pharmaceutically acceptable salt thereof,
wherein
A is a divalent linking moiety comprising 1 to 10 carbon atoms in a chain, a ring, or a combination thereof, wherein at least one carbon atom is optionally replaced with O, —NR$^9$—, or —C(O)—;
B is CR$^3$R$^4$;
X is selected from the group consisting of:

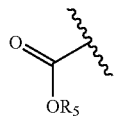 X$_1$

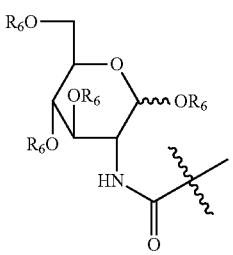 X$_2$

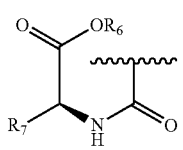 X$_3$

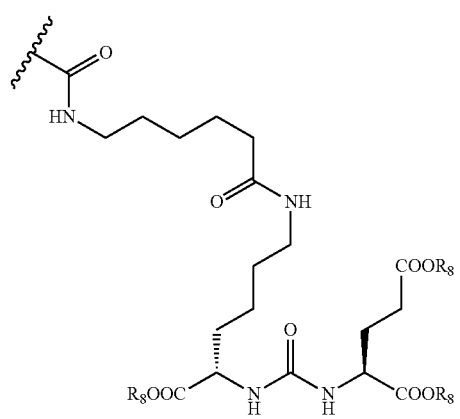 X$_4$

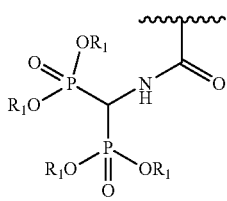 X$_5$

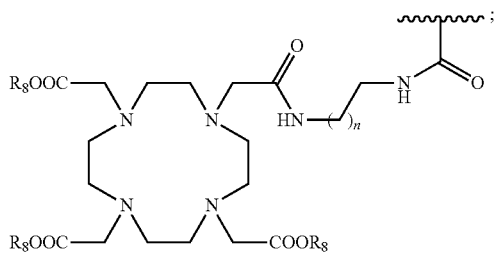 X$_6$;

Y is independently CH or N;

n is from 1 to 8;

R$^1$ is hydrogen or a (C$_1$-C$_6$) alkyl group;

R$^3$ and R$^4$ are independently hydrogen, a (C$_1$-C$_{10}$) alkyl group, an ethylene glycolyl group, or a propylene glycolyl group;

R$^5$, and R$^8$ are independently hydrogen or a carboxylic acid protecting group;

R$^6$ is a (C$_1$-C$_6$) acyl group;

R$^7$ is the α-position substituent of a naturally occurring or non-naturally occurring amino acid;

R$^9$ is independently selected from the group consisting of H, alkyl, cycloalkyl, heterocycloalkyl, aryl, alkylaryl, and heteroaryl; and M is a metal selected from the group consisting of $^{44}$Sc, $^{47}$Sc, $^{203}$Pb, $^{67}$Ga, $^{68}$Ga, $^{72}$As, $^{111}$In, $^{90}$Y, $^{97}$Ru, $^{62}$Cu, $^{64}$Cu, $^{52}$Fe, $^{52m}$Mn, $^{140}$La, $^{175}$Yb, $^{153}$Sm, $^{166}$Ho, $^{149}$Pm, $^{177}$Lu, $^{142}$Pr, $^{159}$Gd, $^{213}$Bi, $^{67}$Cu, $^{111}$Ag, $^{199}$Au, $^{161}$Tb, and $^{51}$Cr.

In one aspect, M is $^{67}$Ga or $^{68}$Ga.

In certain embodiments, the compounds of the present invention are represented by generalized Formula I and II and the attendant definitions, wherein A is a divalent linking moiety comprising 1 to 10 carbon atoms in a chain, a ring, or a combination thereof, wherein at least one carbon atom is optionally replaced with O, —NR$^9$—, or —C(O)—. In another embodiment, A is a divalent linking moiety comprising a C$_1$-C$_{10}$ alkylene group wherein at least one carbon atom is optionally replaced with O, —NR$^9$—, or —C(O)—. In another embodiment, A is (CH$_2$)$_m$, wherein m is an integer from 0 to 6. In another embodiment, A is CH$_2$. Useful examples of the divalent A moiety include —CH$_2$—, —CH$_2$CH$_2$—, —CH$_2$CH$_2$CH$_2$—, —OCH$_2$—, —OCH$_2$CH$_2$—, —OCH$_2$CH$_2$CH$_2$—, —NHCH$_2$—, —NHCH$_2$CH$_2$—, —NHCH$_2$CH$_2$CH$_2$—, —COCH$_2$—, —COCH$_2$CH$_2$—, and —COCH$_2$CH$_2$CH$_2$—.

In certain embodiments, the compounds of the present invention are represented by generalized Formula I and II and the attendant definitions, wherein X is selected from the group consisting of:

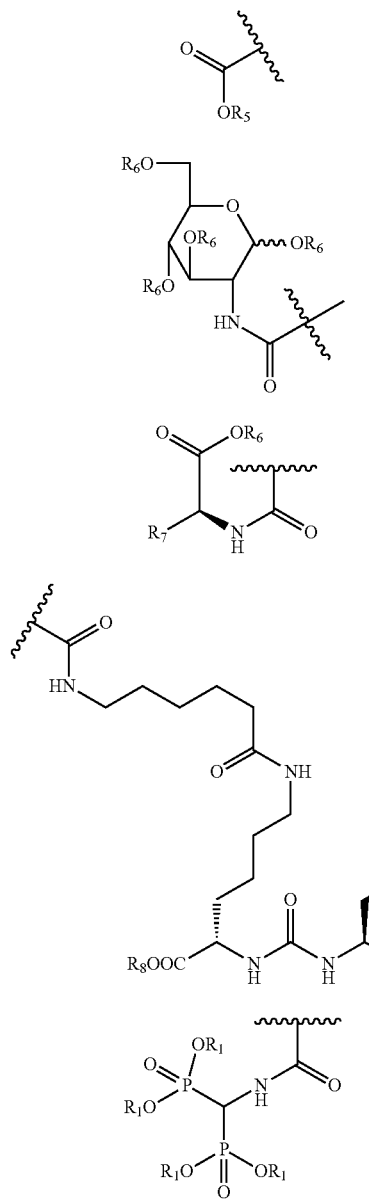

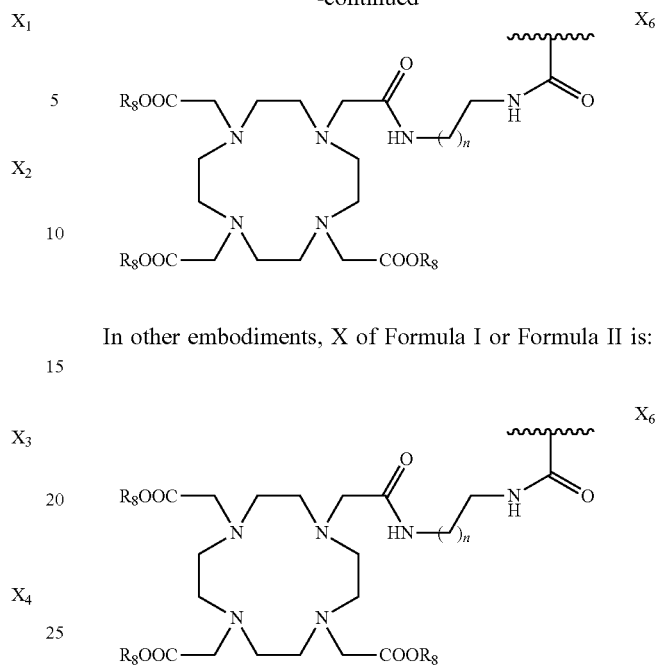

In other embodiments, X of Formula I or Formula II is:

In some embodiments, X of Formula I or Formula II is $X_6$ and n is 1.

In another embodiment, X is a carboxylic acid group or its derivative (X1). In another embodiment, X contains glucosamine group or its derivative (X2). In another embodiment, X contains an amino acid residue or its derivative (X3). In another embodiment, X contains Glu-NH—CO—NH-Lys(Ahx) (X4). In another embodiment, X contains a bisphosphonate group (X5).

Useful $R^7$ groups include glycine, aspartic acid, glutamic acid, and 2-glucosamine.

Useful $R^5$ and $R^8$ groups include a methyl ester, a t-butyl ester, a benzyl ester, and an allyl ester.

In one embodiment, X is one of $X_1$ to $X_5$ and the radionuclide metal (M) is $^{68}Ga$. In another embodiment, X is $X_6$ and the radio metal is $^{177}Lu$ or $^{90}Y$.

In one embodiment, the disclosure relates to a compound having the structure:

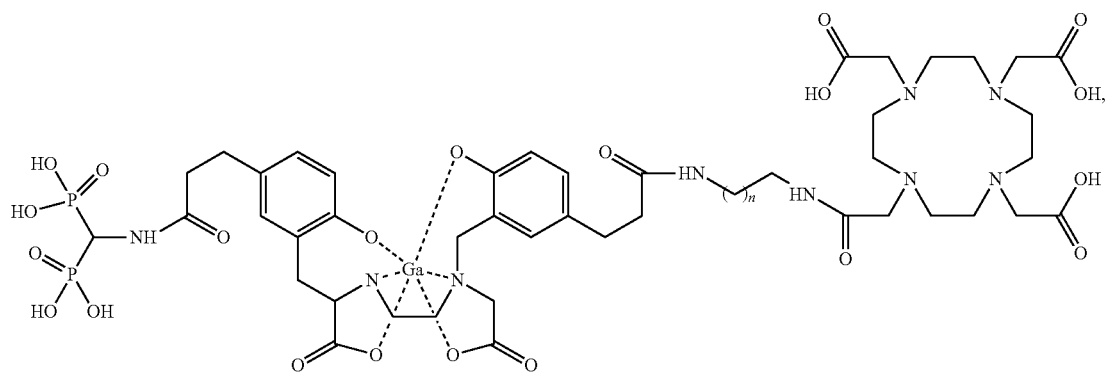

wherein n is from 1 to 8. In one embodiment, n is 1.

In one embodiment, the disclosure relates to a compound having the structure:

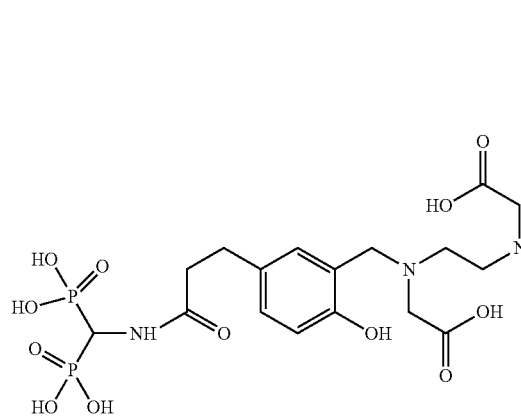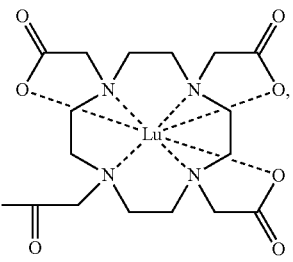

wherein n is from 1 to 8. In one embodiment, n is 1.

The present invention also provides pharmaceutical compositions comprising a pharmaceutical acceptable carrier and a compound or a pharmaceutically acceptable salt of Formula I or Formula II. In certain embodiments the pharmaceutical composition will comprise the reaction precursors necessary generate the compound or salt according to Formula I or subformula thereof upon combination with a radiolabeled precursor.

The present invention provides a kit formulation, comprising a sterile container containing a compound of Formula I or a pharmaceutically acceptable isotonic solution for iv injection thereof, and instructions for diagnostic imaging ($^{68}$Ga) and radiation therapy use ($^{177}$Lu and $^{90}$Y).

The present invention also provides for methods of in vivo imaging, comprising administering an effective amount of a radiometal complex of Formula II to a subject, and detecting the pattern of radioactivity of the complex in said subject.

Typical subjects to which compounds of the invention may be administered will be mammals, particularly primates, especially humans. For veterinary applications, a wide variety of subjects will be suitable, e.g. livestock such as cattle, sheep, goats, cows, swine and the like; poultry such as chickens, ducks, geese, turkeys, and the like; and domesticated animals particularly pets such as dogs and cats. For diagnostic or research applications, a wide variety of mammals will be suitable subjects including rodents (e.g. mice, rats, hamsters), rabbits, primates, and swine such as inbred pigs and the like. Additionally, for in vitro applications, such as in vitro diagnostic and research applications, body fluids and cell samples of the above subjects will be suitable for use such as mammalian, particularly primate such as human, blood, urine or tissue samples, or blood urine or tissue samples of the animals mentioned for veterinary applications.

One useful radiopharmaceutical in accordance with this invention are positron emitting gallium-68 complexes which, when used in conjunction with a $^{68}$Ge/$^{68}$Ga parent/daughter radionuclide generator system, will allow PET imaging studies, avoiding the expense associated with operation of an in-house cyclotron for radionuclide production.

The radiopharmaceutical complexes are used in accordance with the present method for bone imaging. The complexes are formulated into aqueous solutions suitable for intravenous administration using standard techniques for preparation of parenteral diagnostics. An aqueous solution of the present complexes can be sterilized, for example, by passage through a commercially available 0.2 micron filter. The complexes are typically administered intravenously in an amount effective to provide bone concentrations of the radionuclide complex sufficient to provide the requisite photon (gamma/positron) flux for imaging the tissue. The dosage level for any given complex of this invention to achieve acceptable tissue imaging depends on its particular biodistribution and the sensitivity of the tissue imaging equipment. Effective dosage levels can be ascertained by routine experimentation. They typically range from about 1 to about 30 millicuries. Where the complexes are gallium-68 complexes for PET imaging of bone, adequate photon fluxes can be obtained by intravenous administration of from about 1 to about 30 millicuries of the complex.

The term "amino acid" used herein include both naturally occurring amino acids and unnatural amino acids. Naturally occurring amino acid refers to amino acids that are known to be used for forming the basic constituents of proteins, including alanine, arginine, asparagine, aspartic acid, cysteine, cystine, glutamine, glutamic acid, glycine, histidine, hydroxyproline, isoleucine, leucine, lysine, methionine, ornithine, phenylalanine, proline, serine, threonine, tryptophan, tyrosine, valine, and combinations thereof. Examples of unnatural amino acids include: an unnatural analogue of a tyrosine amino acid; an unnatural analogue of a glutamine amino acid; an unnatural analogue of a phenylalanine amino acid; an unnatural analogue of a serine amino acid; an unnatural analogue of a threonine amino acid; an alkyl, aryl, acyl, azido, cyano, halo, hydrazine, hydrazide, hydroxyl, alkenyl, alkynl, ether, thiol, sulfonyl, seleno, ester, thioacid, borate, boronate, phospho, phosphono, phosphine, heterocyclic, enone, imine, aldehyde, hydroxylamine, keto, or amino substituted amino acid, or any combination thereof; an amino acid with a photoactivatable cross-linker; a spin-labeled amino acid; a fluorescent amino acid; an amino acid with a novel functional group; an amino acid that covalently or noncovalently interacts with another molecule; a metal binding amino acid; a metal-containing amino acid; a radioactive amino acid; a photocaged and/or photoisomerizable amino acid; a biotin or biotin-analogue containing amino acid; a glycosylated or carbohydrate modified amino acid; a keto containing amino acid; amino acids comprising polyethylene glycol or polyether; a heavy atom substituted amino acid; a chemically cleavable or photocleavable amino acid; an amino acid with an elongated side chain; an amino acid containing a toxic group; a sugar substituted amino acid, e.g., a sugar substituted serine or the like; a carbon-linked sugar-containing amino acid; a redox-active amino acid; an a-hydroxy containing acid; an amino thio acid containing amino acid; an α,α disubstituted amino acid; a β-amino acid; and a cyclic amino acid other than proline.

The term "acyl" used herein refers to the following structure:

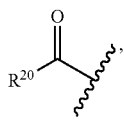

wherein R$^{20}$ is alkyl, cycloalkyl, aryl, (cycloalkyl)alkyl, or arylalkyl, any of which is optionally substituted. The acyl group can be, for example, C$_{1-6}$ alkylcarbonyl (such as, for example, acetyl), arylcarbonyl (such as, for example, benzoyl), levulinoyl, or pivaloyl. In another embodiment, the acyl group is benzoyl.

The term "alkyl" used herein includes both branched and straight-chain saturated aliphatic hydrocarbon groups, having the specified number of carbon atoms. Examples of alkyl include, but are not limited to, methyl, ethyl, n-propyl, i-propyl, n-butyl, s-butyl, t-butyl, n-pentyl, and s-pentyl. Preferred alkyl groups are C$_1$-C$_{10}$ alkyl groups. Typical C$_{1-10}$ alkyl groups include methyl, ethyl, n-propyl, n-butyl, n-pentyl, n-hexyl, n-heptyl, n-octyl, n-nonyl, and n-decyl, isopropyl, sec-butyl, tert-butyl, iso-butyl, iso-pentyl, neo-pentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-methylhexyl, 2-methylhexyl, 3-methylhexyl, 4-methylhexyl, 5-methylhexyl, 1,2-dimethylpentyl, 1,3-dimethylpentyl, 1,2-dimethylhexyl, 1,3-dimethylhexyl, 3,3-dimethylhexyl, 1,2-dimethylheptyl, 1,3-dimethylheptyl, and 3,3-dimethylheptyl, among others. In one embodiment, useful alkyl groups are selected from straight chain C$_{1-6}$ alkyl groups and branched chain C$_{3-6}$ alkyl groups. Typical C$_{1-6}$ alkyl groups include methyl, ethyl, propyl, isopropyl, butyl, sec-butyl, tert-butyl, iso-butyl, pentyl, 3-pentyl, hexyl, among others. In one embodiment, useful alkyl groups are selected from straight chain C$_{2-6}$ alkyl groups and branched chain C$_{3-6}$ alkyl groups. Typical C$_{2-6}$ alkyl groups include ethyl, propyl, isopropyl, butyl, sec-butyl, tert-butyl, iso-butyl, pentyl, 3-pentyl, hexyl among others. In one embodiment, useful alkyl groups are selected from straight chain C$_{1-4}$ alkyl groups and branched chain C$_{3-4}$ alkyl groups. Typical C$_{1-4}$ alkyl groups include methyl, ethyl, propyl, isopropyl, butyl, sec-butyl, tert-butyl, and iso-butyl.

The term "cycloalkyl" used herein includes saturated ring groups, having the specified number of carbon atoms, such as cyclopropyl, cyclobutyl, cyclopentyl, or cyclohexyl. Cycloalkyl groups typically will have 3 to about 12 ring members. In another embodiment, the cycloalkyl has one or two rings. In another embodiment, the cycloalkyl is a C$_3$-C$_8$ cycloalkyl. In another embodiment, the cycloalkyl is a C$_{3-7}$ cycloalkyl. In another embodiment, the cycloalkyl is a C$_{3-6}$ cycloalkyl. Exemplary cycloalkyl groups include cyclopropyl, cyclobutyl, cyclopentyl, cyclohexyl, cycloheptyl, cyclooctyl, norbornyl, decalin, and adamantyl.

The term "heterocycloalkyl" used herein refers to saturated heterocyclic alkyl groups.

The term "aryl" used herein includes C$_{6-14}$ aryl, especially C$_{6-10}$ aryl. Typical C$_{6-14}$ aryl groups include phenyl, naphthyl, phenanthryl, anthracyl, indenyl, azulenyl, biphenyl, biphenylenyl, and fluorenyl groups, more preferably phenyl, naphthyl, and biphenyl groups.

The term "heteroaryl" or "heteroaromatic" used herein refers to groups having 5 to 14 ring atoms, with 6, 10 or 14 π electrons shared in a cyclic array, and containing carbon atoms and 1, 2, or 3 oxygen, nitrogen or sulfur heteroatoms, or 4 nitrogen atoms. In one embodiment, the heteroaryl group is a 5- to 10-membered heteroaryl group. Examples of heteroaryl groups include thienyl, benzo[b]thienyl, naphtho[2,3-b]thienyl, thianthrenyl, furyl, benzofuryl, pyranyl, isobenzofuranyl, benzooxazonyl, chromenyl, xanthenyl, 2H-pyrrolyl, pyrrolyl, imidazolyl, pyrazolyl, pyridyl, pyrazinyl, pyrimidinyl, pyridazinyl, isoindolyl, 3H-indolyl, indolyl, indazolyl, purinyl, isoquinolyl, quinolyl, phthalazinyl, naphthyridinyl, cinnolinyl, quinazolinyl, pteridinyl, 4aH-carbazolyl, carbazolyl, β-carbolinyl, phenanthridinyl, acridinyl, pyrimidinyl, phenanthrolinyl, phenazinyl, thiazolyl, isothiazolyl, phenothiazolyl, isoxazolyl, furazanyl, and phenoxazinyl. Typical heteroaryl groups include thienyl (e.g., thien-2-yl and thien-3-yl), furyl (e.g., 2-furyl and 3-furyl), pyrrolyl (e.g., pyrrol-1-yl, 1H-pyrrol-2-yl and 1H-pyrrol-3-yl), imidazolyl (e.g., imidazol-1-yl, 1H-imidazol-2-yl and 1H-imidazol-4-yl), tetrazolyl (e.g., tetrazol-1-yl and tetrazol-5-yl), pyrazolyl (e.g., 1H-pyrazol-3-yl, 1H-pyrazol-4-yl, and 1H-pyrazol-5-yl), pyridyl (e.g., pyridin-2-yl, pyridin-3-yl, and pyridin-4-yl), pyrimidinyl (e.g., pyrimidin-2-yl, pyrimidin-4-yl, pyrimidin-5-yl, and pyrimidin-5-yl), thiazolyl (e.g., thiazol-2-yl, thiazol-4-yl, and thiazol-5-yl), isothiazolyl (e.g., isothiazol-3-yl, isothiazol-4-yl, and isothiazol-5-yl), oxazolyl (e.g., oxazol-2-yl, oxazol-4-yl, and oxazol-5-yl) and isoxazolyl (e.g., isoxazol-3-yl, isoxazol-4-yl, and isoxazol-5-yl). A 5-membered heteroaryl can contain up to 4 heteroatoms. A 6-membered heteroaryl can contain up to 3 heteroatoms. Each heteroatom is independently selected from nitrogen, oxygen and sulfur.

Suitable carboxylic acid protecting group are well known and include, for example, any suitable carboxylic acid protecting group disclosed in Wuts, P. G. M. & Greene, T. W., Greene's Protective Groups in Organic Synthesis, 4rd Ed., pp. 16-430 (J. Wiley & Sons, 2007), herein incorporated by reference in its entirety. Those skilled in the art will be familiar with the selection, attachment, and cleavage of protecting groups and will appreciate that many different protective groups are known in the art, the suitability of one protective group or another being dependent on the particular synthetic scheme planned. Suitable carboxylic acid protecting group include, for example, the methyl esters, t-butyl esters, benzyl esters, and allyl esters.

Materials and Methods

General

All reagents and solvents were purchased commercially (Aldrich, Acros, or Alfa Inc.) and were used without further purification, unless otherwise indicated. Solvents were dried through a molecular sieve system (Pure Solve Solvent Purification System; Innovative Technology, Inc.). $^1$H and $^{13}$C NMR spectra were recorded on a Bruker Avance spectrometer at 400 MHz and 100 MHz, respectively, and referenced to NMR solvents as indicated. Chemical shifts are reported in ppm (δ), with a coupling constant, J, in Hz. The multiplicity is defined by singlet (s), doublet (d), triplet (t), broad (br), and multiplet (m). High-resolution mass spectrometry (HRMS) data was obtained with an Agilent (Santa Clara, Calif.) G3250AA LC/MSD TOF system. Thin-layer chromatography (TLC) analyses were performed using Merck (Darmstadt, Germany) silica gel 60 $F_{254}$ plates. Generally, crude compounds were purified by flash column chromatography (FC) packed with silica gel (Aldrich). High performance liquid chromatography (HPLC) was performed on an Agilent 1100 series system. A gamma counter (Cobra II auto-gamma counter, Perkin-Elmer) measured $^{68}Ga$ radio-activity. An aqueous solution of [$^{68}Ga$]$GaCl_3$ was obtained from a $^{68}Ge/^{68}Ga$ generator (iTG, Germany). Solid-phase extraction cartridges (SEP Pak® Light QMA, Oasis® HLB 3cc) were obtained from Waters (Milford, Mass., USA). [$^{18}F$]NaF was purchased from IBA (Somerset, N.J.).

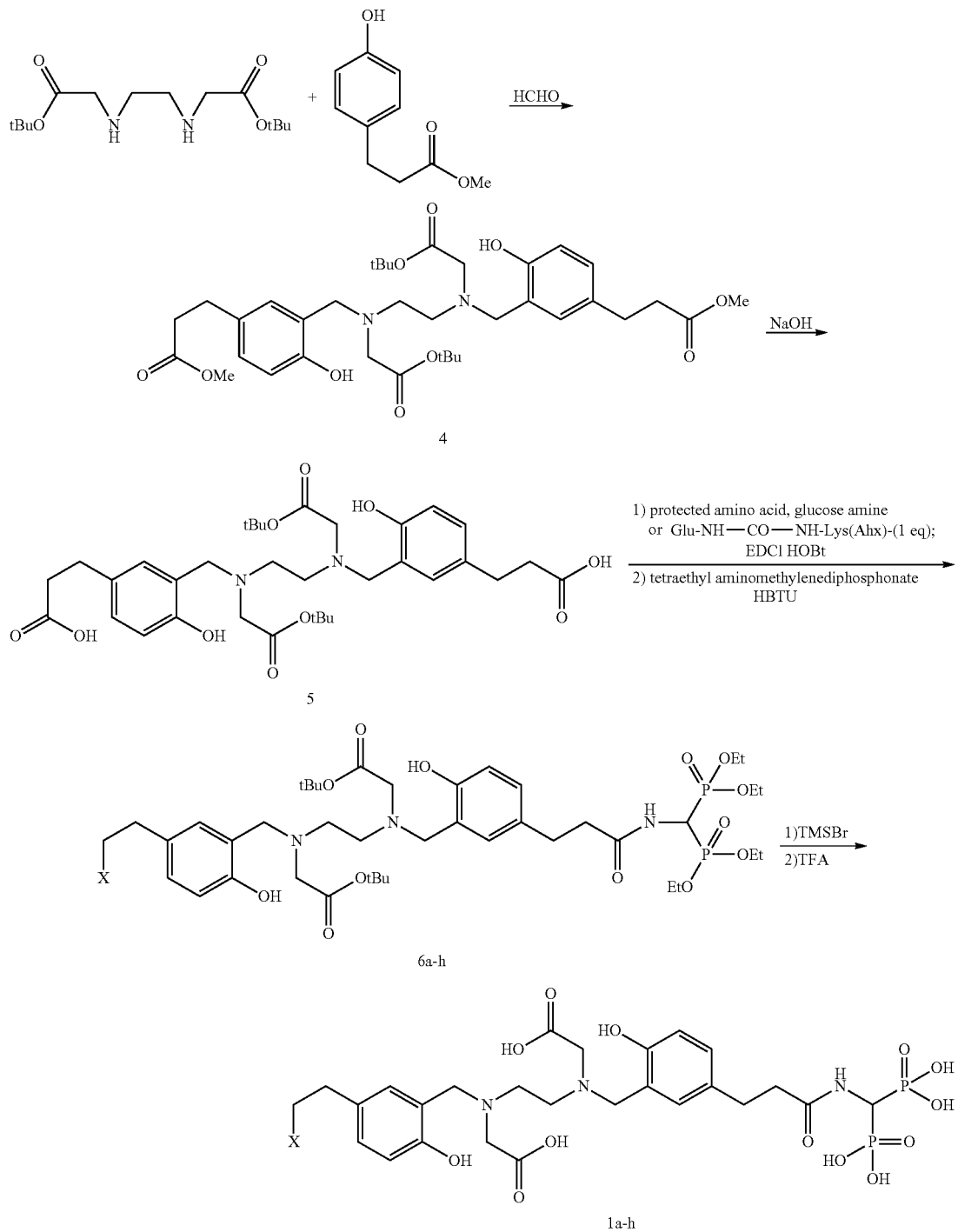

-continued
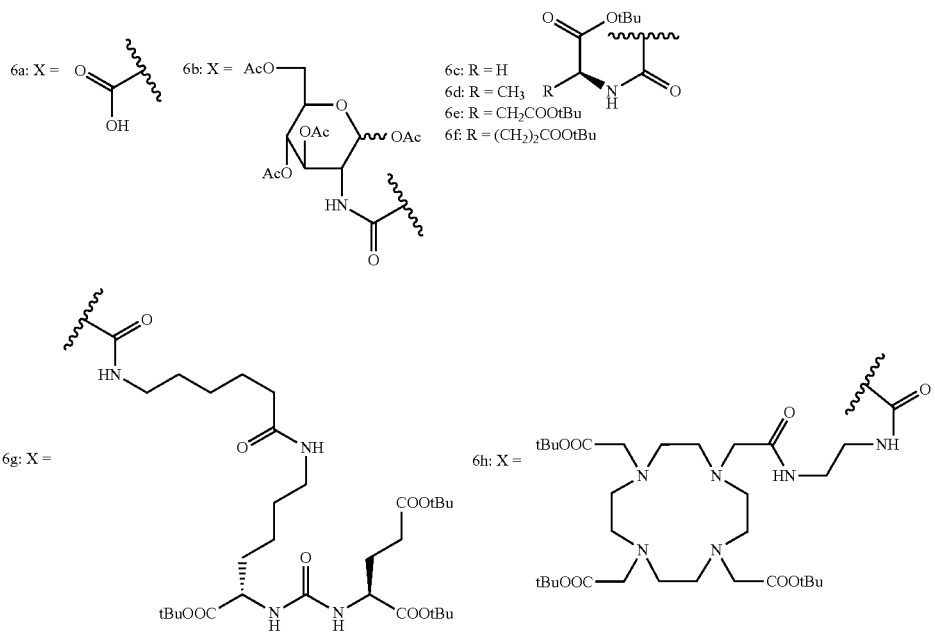
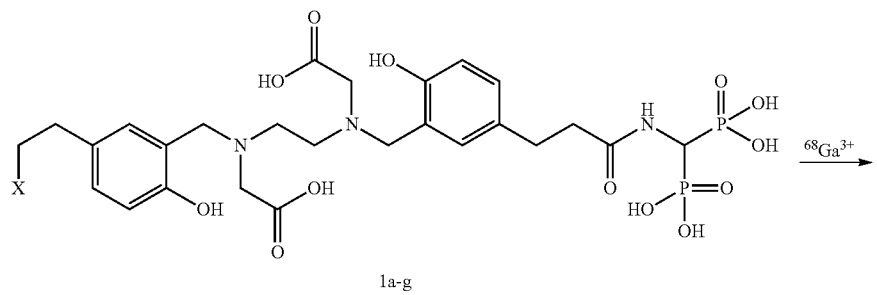
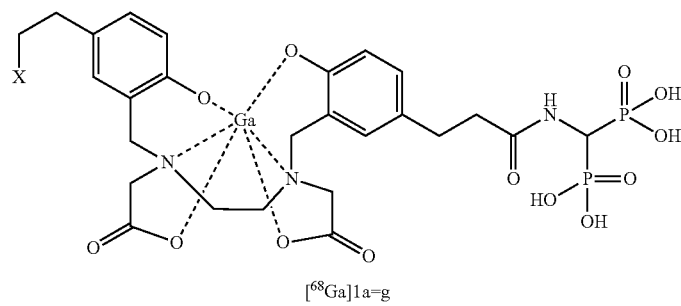
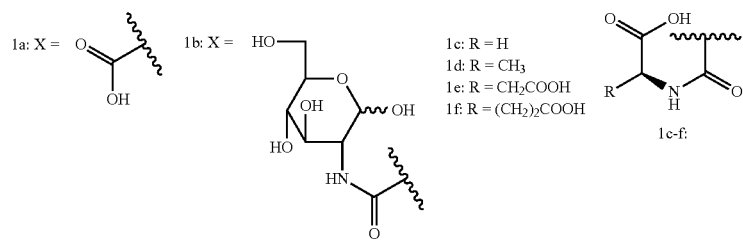

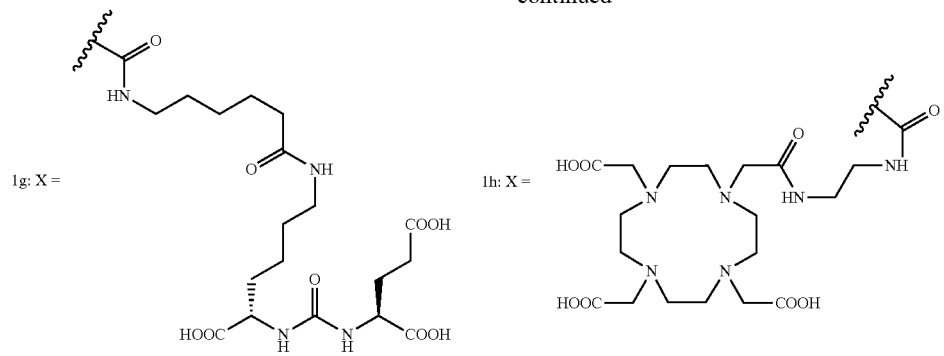

Example 1a-h

Preparation of Ligand

1. Dimethyl 3,3'-(((2,2,13,13-tetramethyl-4,11-dioxo-3,12-dioxa-6,9-diazatetradecane-6,9-diyl)bis(methylene))bis(4-hydroxy-3,1-phenylene))dipropanoate (4)

As summarized in Scheme 1, di-tert-butyl 2,2'-(ethane-1,2-diylbis(azanediyl))diacetate (2 g, 6.94 mmol) and methyl 3-(4-hydroxyphenyl)propanoate (2.63 g, 14.5 mmol) were dissolved in ethanol (50 mL) and toluene (50 mL) in a 100 mL round-bottomed flask. Paraformaldehyde (4.3 g, 145 mmol) was added portion-wise with stirring, and the suspension was heated to reflux overnight. The solvent was then removed. The crude product was washed with water, extracted with dichloromethane (DCM), dried, filtered, evaporated, and purified by FC, to yield 4 as a colorless oil product (3.94 g, 84.5%, (EtOAc/hexane=3/7). $^1$HNMR (400 MHz, CDCl$_3$) δ: 7.00 (dd, 2H, J=2.0 Hz, J=8.4 Hz), 6.77 (d, 2H, J=8.4 Hz), 6.74 (d, 2H, J=2.0 Hz), 3.70 (s, 4H), 3.67 (s, 6H), 3.17 (s, 4H), 2.83 (t, 4H, J=7.8 Hz), 2.69 (s, 4H), 2.57 (t, 4H, J=7.8 Hz), 1.46 (s, 18H). HRMS calcd for $C_{36}H_{53}N_2O_{10}$ 672.3700. found, 673.3680 [M+H]$^+$.

2. 3,3'-(((2,2,13,13-tetramethyl-4,11-dioxo-3,12-dioxa-6,9-diazatetradecane-6,9-diyl)bis(methylene))bis(4-hydroxy-3,1-phenylene))dipropanoic acid (5)

To a stirred solution of 4 (1 g, 1.48 mmol) in methanol (20 mL) and H$_2$O (20 mL), NaOH (5 mmol, 0.2 g) was added. The reaction continued to stir at room temperature overnight, and was neutralized by 1N HCl until pH=7. Most of the solvent was then removed under vacuum, extracted with ethyl acetate, and dried over MgSO$_4$. The crude product was purified by FC (dichloromethane/methanol/NH$_4$OH, 90/9/1, V/V/V) to yield 5 as a white foam (909 mg, 94.7%). $^1$H NMR (400 MHz, CD$_3$OD) δ: 7.05 (dd, J=2.4, 2.0 Hz, 2H), 6.93 (d, J=2.0 Hz, 2H), 6.72 (d, J=8.4 Hz, 2H), 3.80 (s, 4H), 3.34-3.32 (m, 7H), 2.85-2.80 (m, 8H), 2.54-2.50 (m, 4H), 1.489 (s, 18H). $^{13}$C NMR (100 MHz, CD$_3$OD) δ: 176.42, 170.14, 132.02, 130.05, 128.91, 121.21, 115.39, 81.80, 55.34, 54.67, 49.78, 36.49, 30.11, 26.98. HRMS calcd for $C_{34}H_{48}N_2O_{10}$ 644.3309. found, 645.3483 [M+H]$^+$.

General Synthetic Procedures for 6a-h

To a stirred solution of 5 (200 mg, 0.31 mmol) and one of the protected amino acids or protected glucose amines (0.31 mmol) in dimethylformamide (DMF) (20 mL), N,N-diisopropylethylamine (1 mL), N-hydroxybenzotriazole hydrate (HOBt) (84 mg, 0.62 mmol), and 1-ethyl-3-(3-dimethylaminopropyl)carbodiimide (EDCI) (118 mg, 0.62 mmol) were added sequentially. The mixture was stirred at room temperature for 3 h before tetraethyl aminomethylenediphosphonate (94 mg, 0.31 mmol) and HBTU (118 mg, 0.62 mmol) were added sequentially. The mixture was then stirred at room temperature overnight, diluted with EtOAc (50 mL), washed with brine (2×20 mL), dried over Na$_2$SO$_4$, concentrated, and purified by FC (DCMMeOH=10/1) to yield the desired product.

6a: To a stirred solution of 5 (100 mg, 0.15 mmol) and tetraethyl aminomethylenediphosphonate (52 mg, 0.17 mmol) in DMF (20 mL), triethyl amine (1 mL), HOBt (20 mg, 0.15 mmol), and EDCI (59 mg, 0.31 mmol) were added sequentially. The mixture was diluted with EtOAc (50 mL), washed with brine (2×25 mL), dried over Na$_2$SO$_4$, concentrated, and purified by FC (DCM/MeOH/NH$_4$OH=90/9/1) to yield 6a as a white foam (63 mg, 44.3%). $^1$HNMR (400 MHz, CDCl$_3$) δ: 7.11-7.06 (m, 1H), 7.03-7.00 (m, 1H), 6.80-6.72 (m, 4H), 4.26-4.20 (m, 8H), 3.52-3.50 (m, 4H), 3.34 (s, 1H), 2.91-2.78 (m, 6H), 2.68-2.66 (m, 4H), 2.63-2.56 (m, 6H), 1.46 (s, 18H), 1.36 (t, J=6.4 Hz, 12H). HRMS calcd for $C_{43}H_{69}N_3O_{15}P_2$ 929.4204. found 930.4209 [M+H]$^+$.

6b: Following the general procedure, treatment of 5 (200 mg, 0.31 mmol) with 1,3,4,6-tetra-O-acetyl-2-amino-2-deoxy-glucopyranose hydrochloride (118 mg, 0.31 mmol) afforded 6b (111 mg, 28.4%) as a colorless oil. $^1$H NMR (400 MHz, CDCl$_3$) δ: 9.50 (s, 1H), 7.01-6.97 (m, 2H), 6.79-6.66 (m, 5H), 5.34-5.24 (m, 1H), 5.14-4.98 (m, 1H), 4.14-4.09 (m, 8H), 3.69-3.59 (m, 6H), 3.20-3.18 (m, 4H), 2.87-2.47 (m, 8H), 2.67-2.53 (m, 6H), 2.41-2.37 (m, 2H), 1.45 (s, 18H), 1.35-1.30 (m, 12H), 1.27-1.23 (m, 12H). $^{13}$C NMR (100 MHz, CDCl$_3$) δ: 172.66, 171.09, 170.89, 170.68, 170.20, 169.46, 169.24, 155.72, 155.61, 131.20, 130.99, 129.15, 129.04, 128.79, 121.60, 116.27, 92.46, 82.14, 82.09, 72.67, 2.43, 68.11, 63.81, 63.46, 61.74, 60.34, 57.58, 56.08, 55.87, 55.43, 52.77, 50.02, 38.42, 37.82, 30.69, 30.06, 28.03, 20.81, 20.68, 20.54, 16.32, 16.28, 14.16. HRMS calcd for $C_{57}H_{88}N_4O_{23}P_2$ 1258.5315. found: 1259.5321 [M+H]$^+$.

6c: Following the general procedure, treatment of 5 (200 mg, 0.31 mmol) with tert-Butyl aminoacetate hydrochloride (52 mg, 0.31 mmol) afforded 6c (100 mg, 31.1%) as a colorless oil. $^1$H NMR (400 MHz, CDCl$_3$) δ: 9.53 (s, 2H), 7.05-7.00 (m, 2H), 6.77-6.74 (m, 4H), 4.24-4.10 (m, 8H), 3.70-3.67 (m, 3H), 3.19-3.16 (m, 6H), 2.95-2.88 (m, 6H), 2.69-2.64 (m, 4H), 2.57-2.47 (m, 4H), 1.46 (s, 27H), 1.35-1.20 (m, 12H). $^{13}$C NMR (100 MHz, CDCl$_3$) δ: 172.35, 170.05, 155.82, 155.71, 131.38, 130.97, 129.15, 128.88, 121.56, 117.04, 116.39, 82.09, 63.66, 57.81, 55.70, 50.22, 42.01, 40.58, 38.40, 38.02, 30.48, 28.05, 16.33. HRMS calcd for $C_{49}H_{80}N_4O_{16}P_2$ 1042.5045. found: 1043.6564 [M+H]$^+$.

6d: Following the general procedure, treatment of 5 (200 mg, 0.31 mmol) with L-alanine tert-butyl ester hydrochloride (56 mg, 0.31 mmol) afforded 6d (103 mg, 31.7%) as a colorless oil. $^1$H NMR (400 MHz, CDCl$_3$) δ: 7.03-6.97 (m, 2H), 6.84-6.76 (m 4H), 4.21-4.09 (m, 8H), 3.70 (s, 4H), 3.46 (s, 1H), 3.21 (s, 4H), 2.87-2.81 (m, 6H), 2.72-2.61 (m, 4H), 2.49-2.46 (m, 4H), 1.46 (s, 27H), 1.31-1.23 (m, 15H). $^{13}$C NMR (100 MHz, CDCl$_3$) δ:172.39, 171.85, 170.17, 155.57, 131.41, 131.07, 129.40, 128.98, 121.50, 116.31, 115.44, 82.14, 64.03, 63.82, 63.57, 57.78, 55.65, 50.29, 48.59, 38.55, 37.77, 30.48, 28.03, 27.95. HRMS calcd for $C_{50}H_{82}N_4O_{16}P_2$ 1056.5201. found: 1057.7004 [M+H]$^+$.

6e: Following the general procedure, treatment of 5 (200 mg, 0.31 mmol) with L-aspartic acid di-tert-butyl ester hydrochloride (87 mg, 0.31 mmol) afforded 6e (110 mg, 30.8%) as a colorless oil. $^1$H NMR (400 MHz, CDCl$_3$) δ: 7.03-6.98 (m, 2H), 6.80-6.73 (m, 4H), 5.11-4.98 (m, 1H), 4.20-4.08 (m, 8H), 3.71-3.66 (m, 6H), 3.46 (s, 1H), 3.16 (s, 4H), 2.96-2.83 (m, 6H), 2.70-2.65 (m, 6H), 2.58-2.55 (m, 1H), 2.48-2.43 (m, 1H), 1.46 (s, 36H), 1.35-1.25 (m, 12H). $^{13}$C NMR (100 MHz, CDCl$_3$) δ: 172.01, 170.43, 170.19, 170.14, 169.93, 155.71, 155.63, 131.30, 131.00, 129.34, 129.26, 128.92, 128.84, 121.62, 121.54, 116.34, 82.29, 82.07, 81.55, 64.04, 63.79, 57.90, 55.64, 50.37, 49.02, 43.23, 42.60, 38.49, 37.78, 37.50, 30.87, 30.64, 30.45, 28.03, 16.30, 16.26, 16.22. HRMS calcd for $C_{55}H_{90}N_4O_{18}P_2$ 1156.5725. found: 1157.7476 [M+H]$^+$.

6f: Following the general procedure, treatment of 5 (200 mg, 0.31 mmol) with L-glutamic acid di-tert-butyl ester hydrochloride (91 mg, 0.31 mmol) afforded 6f (118 mg, 32.8%) as a colorless oil. $^1$H NMR (400 MHz, CDCl$_3$) δ: 7.03-6.99 (m, 2H), 6.76-6.74 (m, 4H), 5.13-4.99 (m, 1H), 4.22-4.10 (m, 8H), 3.69 (s, 4H), 3.47 (s, 1H), 3.18 (s, 4H), 2.87-2.85 (m, 4H), 2.69 (s, 4H), 2.49-2.44 (s, 4H), 2.29-2.13 (m, 2H), 2.11-2.05 (m, 1H), 1.92-1.82 (m, 1H), 1.46 (s, 36H), 1.35-1.26 (m, 12H). $^{13}$C NMR (100 MHz, CDCl$_3$) δ: 172.25, 172.08, 171.41, 171.24, 170.00, 155.94, 155.74, 131.33, 130.92, 129.11, 128.88, 121.56, 116.39, 82.21, 82.06, 82.04, 63.67, 57.97, 55.56, 52.16, 50.32, 43.33, 38.55, 38.00, 3.52, 30.65, 30.46, 28.07, 28.05, 27.98, 27.71, 16.35, 16.32, 16.28. HRMS calcd for $C_{56}H_{92}N_4O_{18}P_2$ 1170.5882. found:1171.5891 [M+H]$^+$.

General Synthetic Procedures for 1a-f

To a stirred solution of 6a-f in acetonitrile (1 mL), bromotrimethylsilane was added, and the mixture continued stirring at room temperature overnight. The solvent was then removed under vacuum, trifluoroacetic acid (TFA) (2 mL) was added, and the reaction was again stirred at room temperature overnight. The mixture was then removed under vacuum, and the residue was recrystallized from ether/EtOH to yield 1a-f as a white solid.

1a: Following the general procedure, treatment of 6a (50 mg, 0.054 mmol) with bromotrimethylsilane (73 mg, 0.47 mmol) gave 1a (31 mg, 82.3%) as a white solid. $^1$HNMR (400 MHz, dimethyl sulfoxide, DMSO-d6) δ: 7.90-7.86 (m, 4H), 7.36-7.33 (m, 2H), 3.77-3.75 (m, 5H), 3.33-3.29 (m, 6H), 2.66-2.61 (m, 4H).

1b: Sodium methylate (25 mg, 0.47 mmol) was mixed and stirred with 6b (60 mg, 0.047 mmol) dissolved in methanol (5 mL) at room temperature for 2 h. Deprotection was monitored by LC-MS, and the reaction was neutralized by 1N HCl until pH=7. Most of the solvent was then removed under vacuum and extracted with ethyl acetate. The crude product was dried over MgSO$_4$ without further purification and dissolved in acetonitrile (1.0 mL) before bromotrimethylsilane (1.0 mL) was added. The mixture was then stirred at room temperature overnight before the solvent was removed under vacuum, ether was added, filtered, and the solid was collected. The solid was then dissolved in TFA (2 mL), and the reaction was stirred at room temperature overnight. The above mixture was removed under vacuum, and the residue was recrystallized from ether/EtOH to give 1b as a light yellow solid. $^1$HNMR (400 MHz, DMSO-d6) δ: 7.91 (s, 1H), 7.34-7.06 (m, 5H), 6.80-6.77 (m, 2H), 4.02-3.89 (m, 10H), 3.62-3.56 (m, 5H), 3.23-3.16 (m, 5H), 2.72-2.70 (m, 4H), 2.45-2.34 (m, 2H), 2.05-1.98 (m, 2H). $^{13}$C NMR (100 MHz, DMSO-d6) δ: 173.17, 171.41, 171.11, 170.72, 158.72, 158.40, 155.08, 154.77, 132.38, 131.91, 131.43, 130.28, 119.49, 118.97, 115.89, 115.72, 65.36, 55.34, 52.80, 51.69, 50.13, 35.64, 30.64, 21.60, 21.11, 15.61.

1c: Following the general procedure, treatment of 6c (50 mg, 0.047 mmol) with bromotrimethylsilane (73 mg, 0.47 mmol) afforded 1c (29 mg, 80.1%) as a white solid. $^1$HNMR (400 MHz, DMSO-d6) δ: 7.11-7.09 (m, 4H), 6.73-6.70 (m, 2H), 3.71 (s, 4H), 3.46 (s, 1H), 2.98-2.68 (m, 8H), 2.51-2.41 (m, 10H). $^{13}$CNMR (100 MHz, DMSO-d6) 174.95, 173.86, 172.99, 161.24, 154.93, 132.73, 118.37, 116.20, 115.11, 4.18, 49.61, 40.91, 30.03, 21.32.

1d: Following the general procedure, treatment of 6d (50 mg, 0.047 mmol) with bromotrimethylsilane (73 mg, 0.47 mmol) afforded 1d (30 mg, 81.5%) as a white solid. $^1$HNMR (400 MHz, DMSO-d6) δ: 7.09-7.05 (m, 4H), 6.78-6.75 (m, 2H), 3.70 (s, 4H), 3.42 (s, 1H), 2.73-2.68 (m, 6H), 2.54-2.45 (m, 10H), 1.36-1.32 (m, 3H). $^{13}$CNMR (100 MHz, DMSO-d6) δ: 174.71, 172.28, 171.96, 170.82, 159.13, 155.07, 132.38, 132.26, 130.40, 118.66, 15.89, 115.79, 65.36, 56.62, 47.88, 22.87, 18.93.

1e: Following the general procedure, treatment of 6e (50 mg, 0.043 mmol) with bromotrimethylsilane (65 mg, 0.43 mmol) afforded 1e (30 mg, 81.3%) as a white solid. $^1$HNMR (400 MHz, DMSO-d6) δ: 8.18 (s, 1H), 7.13-7.01 (m, 4H), 6.81-6.78 (m, 2H), 3.36-3.31 (s, 2H), 3.20 (s, 6H), 2.73-2.66 (m, 6H), 2.56-2.54 (m, 2H), 2.45 (s, 4H), 2.37-2.34 (m, 4H). $^{13}$C NMR (100 MHz, DMSO-d6) δ: 172.96, 172.13, 171.94, 170.59, 158.86, 158.50, 158.14, 155.02, 154.89, 65.36, 56.49, 49.03, 37.44, 36.55, 30.58, 19.00, 15.61.

1f: Following the general procedure, treatment of 6f (50 mg, 0.042 mmol) with bromotrimethylsilane (65 mg, 0.42 mmol) gave 1f (29 mg, 80.9%) as a white solid. $^1$HNMR (400 MHz, DMSO-d6) δ: 7.11-7.08 (m, 4H), 6.72-6.69 (m, 2H), 3.72 (s, 4H), 3.45 (s, 1H), 3.31 (s, 1H), 2.72-2.68 (m, 6H), 2.51-2.45 (m, 6H), 2.39-2.34 (m, 4H). $^{13}$CNMR (100 MHz, DMSO-d6) δ: 174.71, 172.28, 171.96, 170.82, 159.13, 158.81, 158.49, 154.95, 154.79, 132.38, 132.26, 130.40, 118.66, 115.89, 115.79, 65.36, 56.52, 47.88, 22.87, 18.93, 17.61.

Synthesis of 1g

To a stirred solution of 5 (50 mg, 0.054 mmol) and (S)-di-tert-butyl 2-(3-((S)-6-(6-aminohexanamido)-1-tert-butoxy-1-oxohexan-2-yl)ureido)pentanedioate (20 mg, 0.11 mmol) in 20 mL DMF, 1 ml N,N-diisopropylethylamine, HOBt (15 mg, 0.11 mmol) and EDCI (118 mg, 0.62 mmol) were added sequentially. The mixture was stirred at room temperature overnight. The mixture was diluted with EtOAc (50 mL), washed with brine (2×20 mL), dried over Na$_2$SO$_4$, concentrated, and purified by FC (DCM/MeOH=10/1) to yield a crude product 6g (46 mg, 61.2%). To a stirred solution of 6g (30 mg, 0.021 mmol) in 1 mL acetonitrile, bromotrimethylsilane (16 mg, 0.1 mmol) was added. The mixture was stirred at room temperature overnight, the solvent was removed under vacuum, TFA (4 mL) was added, and the reaction was stirred at room temperature overnight. The above mixture was then removed under vacuum, and the residue was recrystallized from ether/EtOH to yield 1g as a white solid product (21 mg, 86.4%). $^1$HNMR (400 MHz, DMSO-$_{d6}$) δ: 7.85-7.69 (m, 2H), 7.18-7.08 (m, 4H), 6.89-6.67 (m, 2H), 6.89-6.67 (m, 1H), 6.34 (s, 1H), 3.49-3.21 (m, 10H), 2.89-2.65 (m, 10H), 2.49-2.18 (m, 7H), 2.19-1.88 (m, 6H), 1.77-1.55 (m, 4H), 1.48-1.09 (m, 8H). $^{13}$CNMR (100 MHz, DMSO.$_{d6}$)$^{13}$C NMR (100 MHz, CDCl$_3$) δ: 177.48, 174.95, 174.58, 174.17, 172.49, 171.85, 171.50, 170.40, 170.12, 159.31, 158.95, 158.58, 157.79, 154.99, 132.55, 132.39, 130.63, 120.39, 118.51, 117.50, 115.91, 114.61, 111.71, 65.35, 60.21, 56.50, 52.75, 52.15, 35.82, 30.36, 29.28, 27.99, 25.49, 23.08, 18.97, 15.59.

49.94, 43.25, 42.25, 39.14, 38.99, 38.10, 37.51, 30.87, 30.32, 27.83, 27.78, 27.72, 16.16, 16.13, 16.10, 16.07. HRMS calcd for C$_{73}$H$_{125}$N$_9$O$_{21}$P$_2$ 1525.8465. found, 1526.8258[M+H]$^+$. To a stirred solution of 6h (0.4 g, 0.26 mmol) in 10 mL acetonitrile, 1.5 mL bromotrimethylsilane was added. The mixture continued stirring at room temperature overnight. The solvent was then removed under vacuum, TFA (4 ml) was added, and the reaction was, again, stirred at room temperature overnight. The mixture was then removed under vacuum, and the residue was purified EZ combflash 1h (0.27 g, 93.1%). $^1$HNMR (400 MHz, CDCl$_3$) δ: $^{13}$C NMR (100 MHz, CDCl$_3$) δ 172.44, 172.10, 169.95, 159.37, 159.01, 158.63, 155.14, 132.84, 132.45, 130.98, 120.08, 117.19, 116.01, 114.31, 111.44, 69.35, 65.36, 60.21, 56.48, 55.20, 54.34, 53.00, 51.68, 51.05, 49.63, 48.93, 48.43, 30.60, 22.90, 21.21, 20.92, 18.99, 15.61, 14.54, 13.92 HRMS calcd for C$_{45}$H$_{69}$N$_9$O$_{21}$P$_2$ 1133.4083. found, 1134.4131[M+H]$^+$.

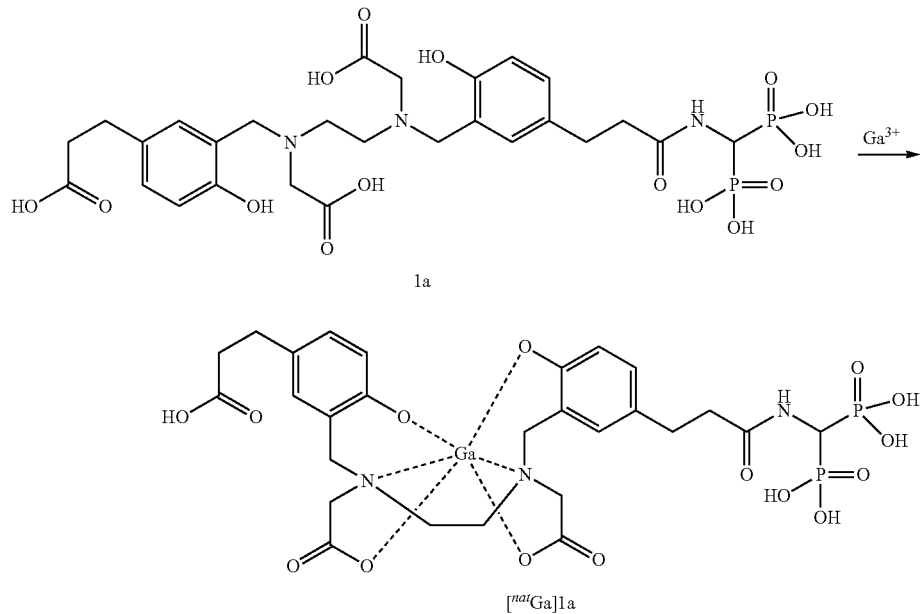

Scheme 2
Preparation of [$^{nat}$Ga$^{3+}$]1a

1a

[$^{nat}$Ga]1a

Synthesis of 1h

To a stirred solution of compound 6a (0.4 g, 0.43 mmol) and compound 2-Aminoethyl-mono-amide-DOTA-tris(t-Bu ester) (0.29 g, 0.43 mmol) in 20 mL DMF, 2 mL DIEPA, HOBt (6 mg, 0.043 mmol) and EDCI (0.16 g, 0.86 mmol) were added sequentially. The reaction was stirred at room temperature for overnight. The mixture was diluted with 100 mLEtOAc, washed with brine (25×2 mL), dried over Na$_2$SO$_4$, concentrated and purified by combiflash (DCM/MeOH/NH$_4$OH=90/9/1) to give 6h as white foam (0.39 g, 60%). $^1$HNMR (400 MHz, CDCl$_3$) δ: 8.04 (s, 1H), 7.90 (s, 1H), 6.80-6.82 (m, 2H), 6.65 (s, 1H), 6.62 (s, 1H), 6.53 (t, J=8.2 Hz, 2H), 4.96-4.84 (m, 1H), 4.00-3.92 (m, 8H), 3.50 (s, 4H), 3.23-3.15 (m, 16H), 3.03 (s, 6H), 2.68-2.62 (m, 8H), 2.49 (s, 6H), 2.41-2.31 (m, 8H), 1.28 (s, 45H), 1.16-1.09 (m, 3H). $^{13}$C NMR (100 MHz, CDCl$_3$) δ: 173.64, 172.33, 172.04, 171.67, 170.06, 155.44, 155.13, 131.83, 131.00, 129.25, 129.10, 128.83, 128.67, 121.26, 116.03, 115.84, 81.80, 81.77, 81.73, 81.67, 77.33, 77.01, 63.56, 63.54, 57.68, 57.55, 55.89, 55.52, 55.45, 55.29, 53.96, 52.58, Example 2

Synthesis of compound [$^{nat}$Ga$^{3+}$]1a

As shown in Scheme 2, GaCl$_3$ (1.7 mg, 0.01 mmol) in 0.1 mL H$_2$O was added to a solution of 1a (7 mg, 0.01 mmol) in DMSO (0.5 mL). The reaction solution was adjusted to pH 4 and stirred at room temperature overnight. The solution was then evaporated under vacuum, and the crude product was recrystalled from ethanol and H$_2$O to yield [$^{nat}$Ga$^{3+}$]1a as a white solid (6.8 mg, 90.2%). $^1$HNMR (400 MHz, DMSO-d6) δ: 7.38 (s, 1H), 7.25-7.20 (m, 4H), 6.88 (s, 1H), 3.61-3.52 (m, 4H), 3.49 (s, 2H), 3.33-3.15 (m, 6H), 2.71 (s, 4H), 2.55 (s, 2H), 2.45 (s, 2H). $^{13}$C NMR (400 MHz, DMSO-d6) δ: 174.39, 173.04, 171.69, 168.39, 168.23, 155.46, 155.36, 133.53, 132.49, 132.12, 131.80, 117.00, 116.19, 115.51, 70.19, 53.10, 49.04, 37.26, 35.90, 29.83, 22.64.

Scheme 3
Synthesis of 2,2'-(ethane-1,2-diylbis((5-(3-((diphosphonomethyl)amino)-3-oxopropyl)-2-hydroxybenzyl)azanediyl)diacetic acid (2)

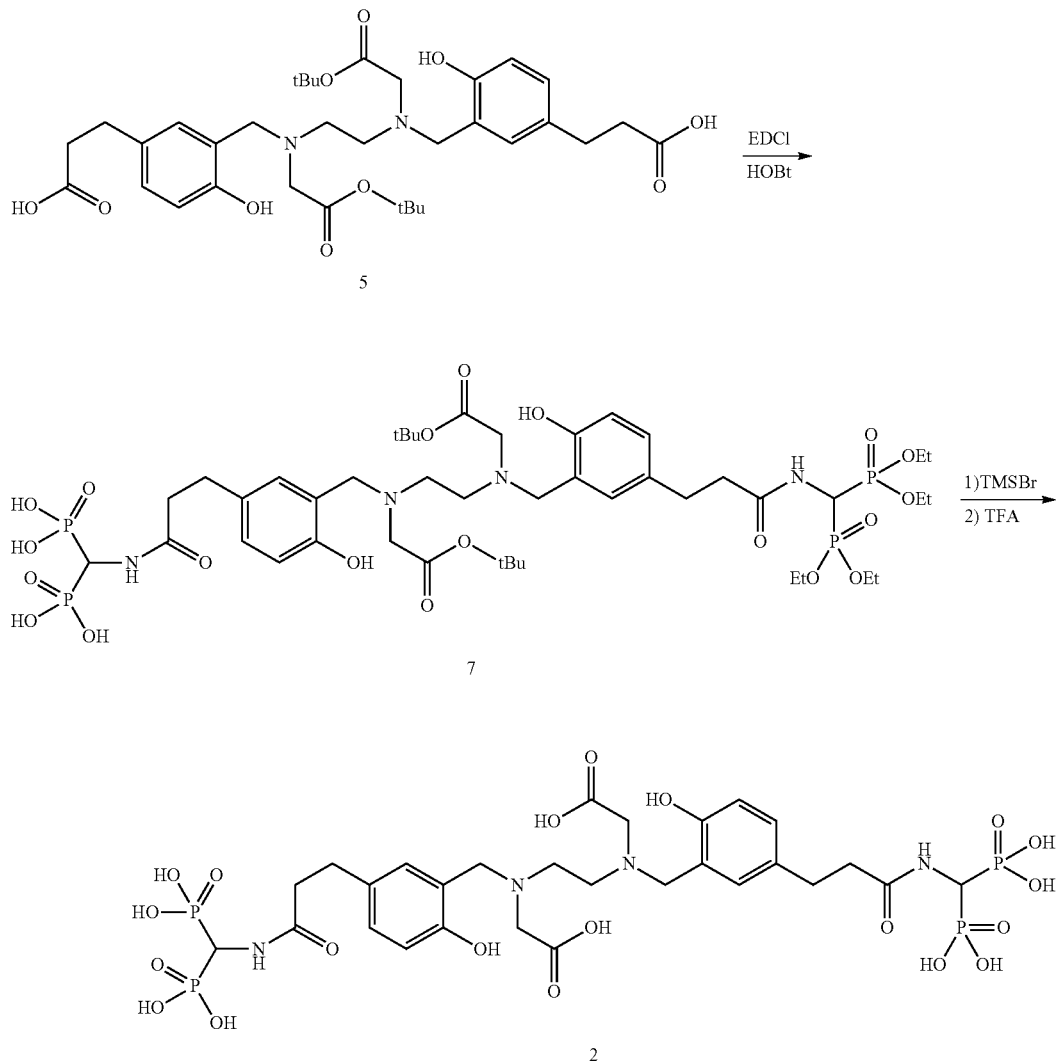

Example 3

Synthesis of compound 2

1. ((3-(3-(((2-((5-(3-((bis(diethoxyphosphoryl) methyl)amino)-3-oxopropyl)-2-hydroxybenzyl)(2-(tert-butoxy)-2-oxoethyl)amino)ethyl)(2-(tert-butoxy)-2-oxoethyl) amino)methyl)-4-hydroxyphenyl) propanamido) methylene)diphosphonic acid (7)

As summarized in Scheme 3, triethyl amine (2 mL), HOBt (44 mg, 0.33 mmol), and HBTU (129 mg, 0.34 mmol) were added sequentially to a stirred solution of 5 (100 mg, 0.15 mmol) and tetraethyl aminomethylenediphosphonate (52 mg, 0.33 mmol) in 20 mL DMF. The mixture was stirred at room temperature overnight, diluted with EtOAc (50 mL), washed with brine (20×2 mL), dried over $Na_2SO_4$, concentrated, and purified by FC (DCM/MeOH/$NH_4OH$=90/9/1) to yield 7 as a white foam (116 mg, 41.2%). $^1$HNMR (400 MHz, $CDCl_3$) δ: 7.01 (t, J=3.6 Hz, 12H), 6.78-6.75 (m, 4H), 4.22-4.14 (m, 16H), 3.71 (s, 4H), 3.18 (s, 4H), 2.89-2.85 (m, 6H), 2.70 (s, 4H), 2.56-2.52 (t, J=3.6 Hz, 4H), 1.46 (s, 18H), 1.36-1.30 (m, 24H). HRMS calcd for $C_{52}H_{90}N_4O_{20}P_4$ 1214.5099. found 1215.5061 $[M+H]^+$.

2. 2,2'-(ethane-1,2-diylbis((5-(3-((diphosphonomethyl)amino)-3-oxopropyl)-2-hydroxybenzyl) azanediyl))diacetic acid (2)

To a stirred solution of 7 (60 mg, 0.049 mmol) in acetonitrile (1 mL), bromotrimethylsilane (75 mg, 0.49 mmol) was added. The mixture was stirred at room temperature overnight, the solvent was removed under vacuum, and TFA (2 mL) was added before the reaction was, again, stirred at room temperature overnight. The mixture was then removed under vacuum, and the residue was recrystallized from ether/EtOH to yield 2 as a white solid (34 mg, 82.1%). $^1$HNMR (400 MHz, DMSO-d6) δ: 7.24-7.20 (m, 4H), 6.88 (d, J=4.32 Hz, 2H), 4.41-4.37 (m, 4H), 3.87 (s, 2H), 2.88-2.81 (m, 6H), 2.61-2.68 (m, 4H), 2.35-2.33 (m, 4H).

Scheme 4
2,2'-(((((propane-1,3-diylbis(azanediyl))bis(3-oxopropane-3,1-diyl))bis(2-hydroxy-5,1-phenylene))bis(methylene))bis((2-((carboxymethyl)(5-(3-((diphosphonomethyl) amino)-3-oxopropyl)-2-hydroxybenzyl)amino)ethyl)azanediyl)diacetic acid (3)

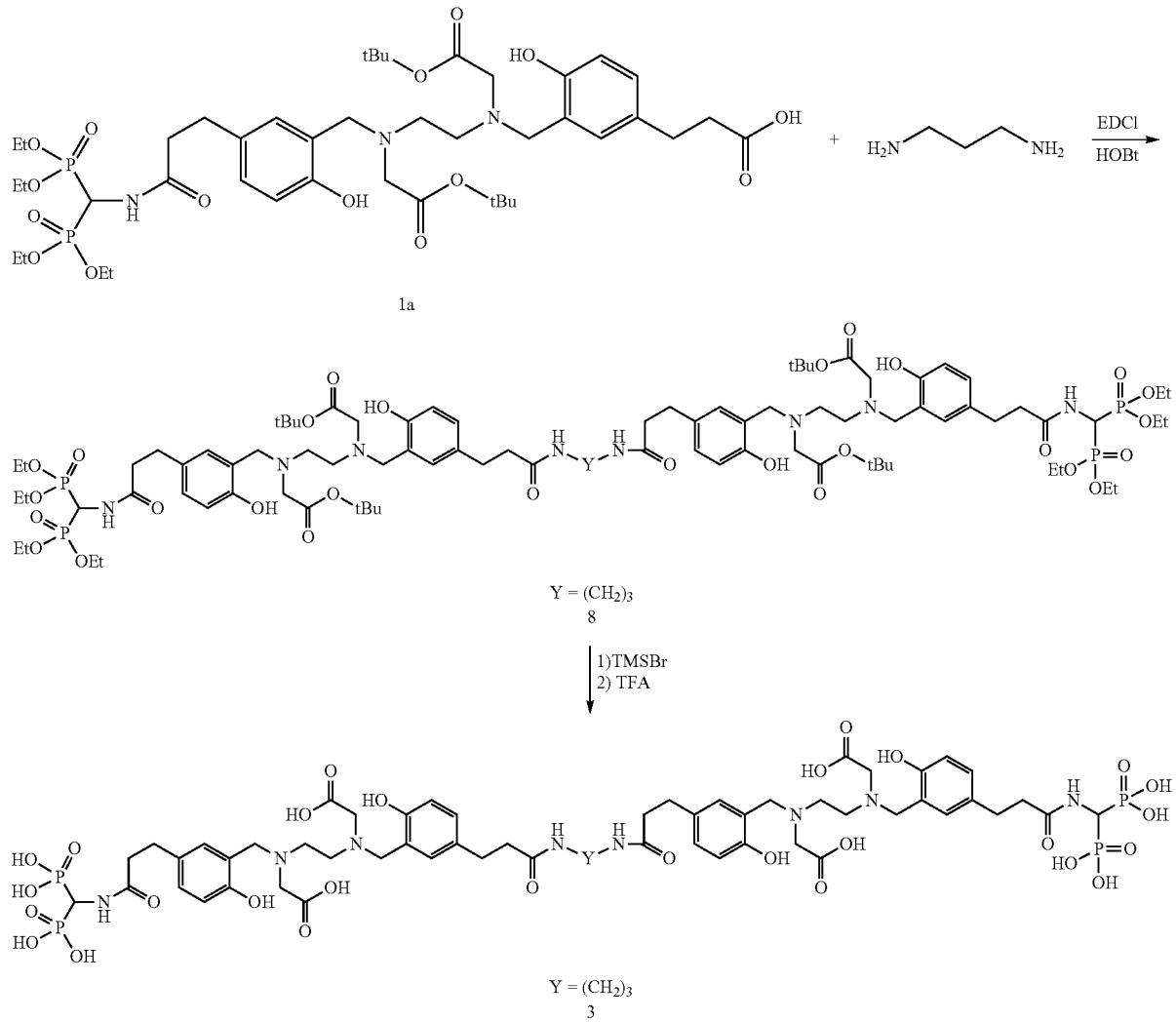

Example 4

Synthesis of Compound 3

1. Di-tert-butyl 2,2'-(((((propane-1,3-diylbis(azanediyl))bis(3-oxopropane-3,1-diyl))bis(2-hydroxy-5,1-phenylene))bis(methylene))bis((2-((5-(3-((bis(diethoxy phosphoryl)methyl)amino)-3-oxopropyl)-2-hydroxybenzyl)(2-(tert-butoxy)-2-oxoethyl)amino)ethyl)azanediyl)) diacetate (8)

To a stirred solution of 1a (50 mg, 0.054 mmol) and 1,3-diaminopropane (2 mg, 0.027 mmol) in 10 mL DMF, triethyl amine (2 mL), HOBt (14 mg, 0.11 mmol), and EDCI (40 mg, 0.22 mmol) were added sequentially, as shown in Scheme 4. The mixture was stirred at room temperature overnight, diluted with EtOAc (50 mL), washed with brine (2×20 mL), dried over $Na_2SO_4$, concentrated, and purified by FC (DCM/MeOH/$NH_4$OH=90/9/1) to yield 8 as a white foam (27 mg, 53.2%). HRMS calcd for $C_{90}H_{146}N_8O_{28}P_4$ [M]+2H$^+$949.9577. found 949.9581 [M]+2H$^+$.

2. 2,2'-(((((propane-1,3-diylbis(azanediyl))bis(3-oxopropane-3,1-diyl))bis(2-hydroxy-5,1-phenylene))bis(methylene))bis((2-((carboxymethyl)(5-(3-((diphosphonomethyl) amino)-3-oxopropyl)-2-hydroxybenzyl)amino)ethyl)azanediyl))diacetic acid (3)

To a stirred solution of 8 (20 mg, 0.01 mmol) in acetonitrile (1 mL), bromotrimethylsilane (16 mg, 0.1 mmol) was added, and the mixture was stirred at room temperature overnight. The solvent was removed under vacuum, TFA (2 mL) was added, and the reaction was, again, stirred at room temperature overnight. The mixture was then removed under vacuum, and the residue was recrystallized from ether/EtOH to yield 3 as a white solid product (12 mg, 81.5%). $^1$HNMR (400 MHz, DMSO-d6) δ: 7.11-7.07 (m, 8H), 6.74-6.68 (m, 4H), 3.73 (s, 8H), 3.43 (s, 2H), 3.08-2.92 (m, 8H), 2.82-2.72 (m, 12H), 2.67-2.56 (m, 10 OH), 2.49-2.31 (m, 8H).

Example 5
Radiolabeling with $^{68}$Ga
Gallium-68 eluted in a 0.05 N HCl solution was obtained from a $^{68}$Ge/$^{68}$Ga generator (iTG, Germany). Preparation of $^{68}$Ga labeled BPAMD was accomplished using the labeling procedures previously reported.
Scheme 5: $^{68}$Ga labeling of compounds 1a-h
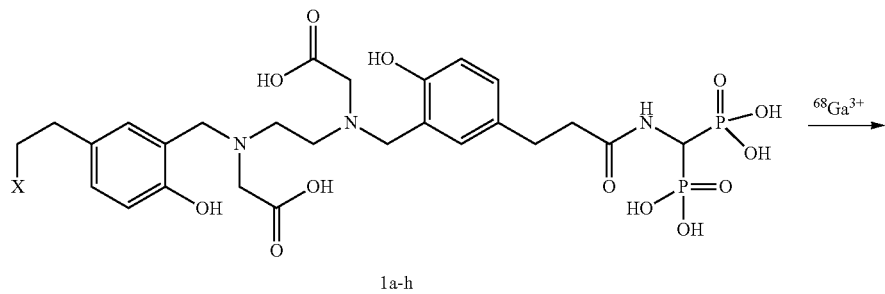
1a-h
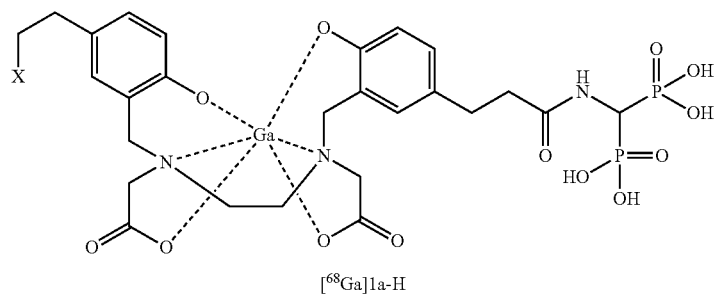
[$^{68}$Ga]1a-H
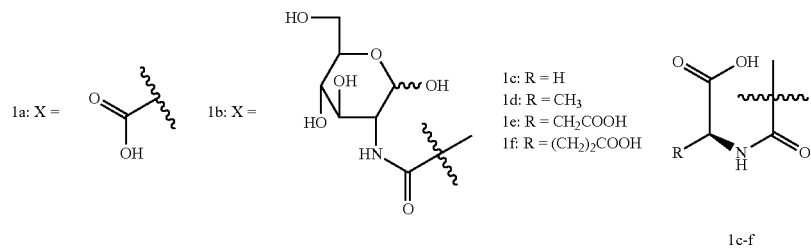
1a: X =    1b: X =    1c: R = H
           1d: R = CH$_3$
           1e: R = CH$_2$COOH
           1f: R = (CH$_2$)$_2$COOH
1c-f
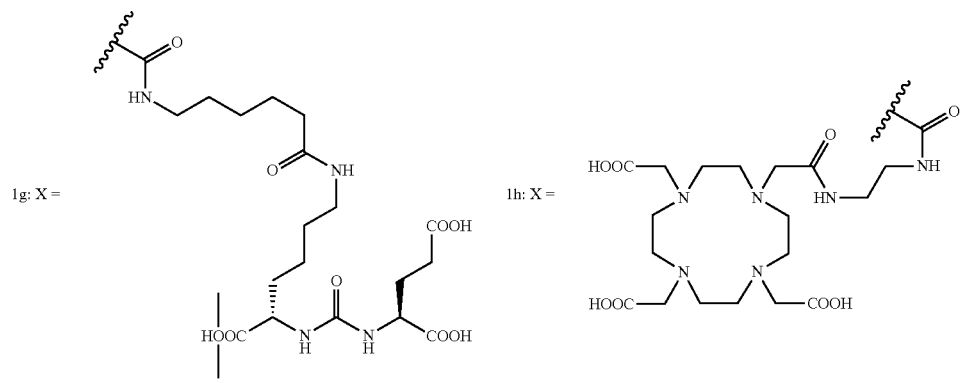
1g: X =    1h: X =

Scheme 6: ⁶⁸Ga labeling of compounds 2

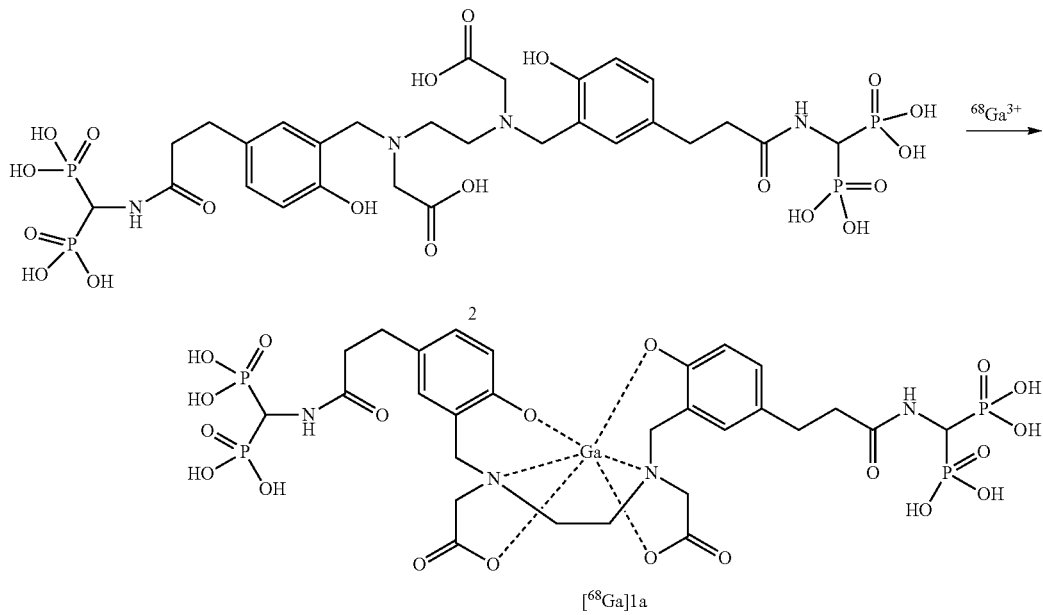

Scheme 7: ⁶⁸Ga labeling of compound 3

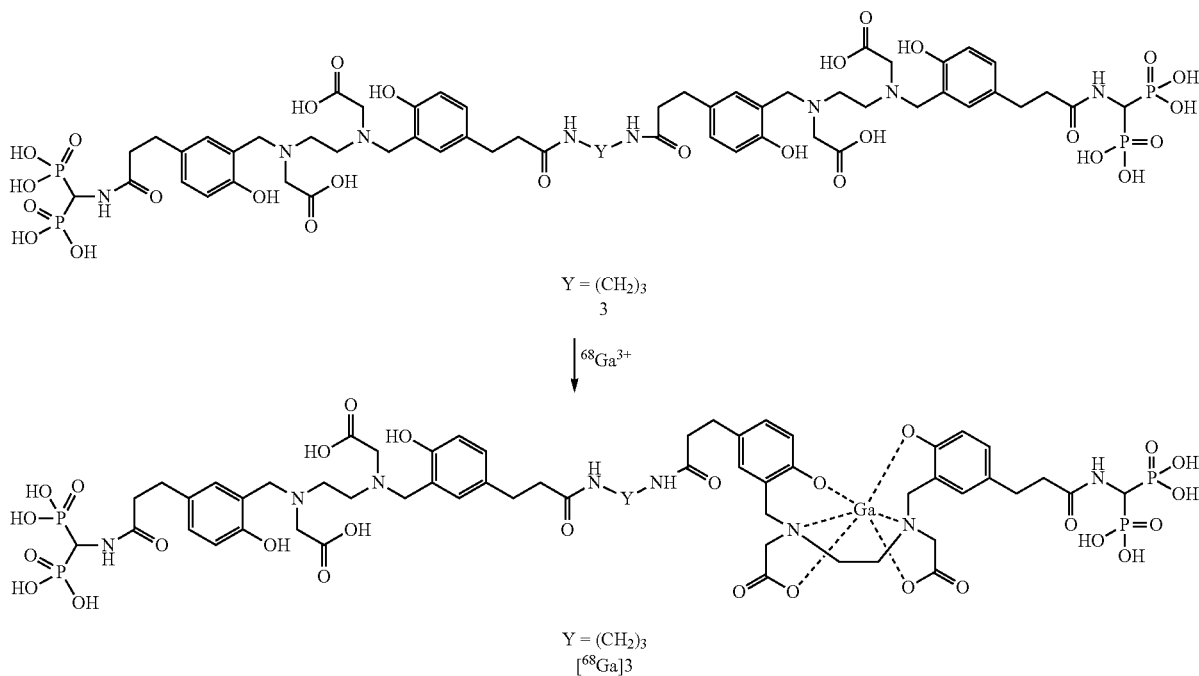

To prepare the new HBED-CC bisphosphonate derivatives for ⁶⁸Ga labeling, a stock solution of ligands 1a-1h (200 μM in 0.1 N NaOAc), 2 (200 μM in 0.1 N NaOAc), and 3 (200 μM in 0.1 N NaOAc) were prepared and used for each study. ⁶⁸Ga labeling was performed by adding the ⁶⁸Ga solution to different solutions of ligands 1a-h, 2, and 3 as seen in Schemes 5-7. Labeling conditions for 1a-h, 2, and 3 were, 200 μL of ⁶⁸GaCl₃ in 0.05 N HCl and a 200 M ligand solution of 1a-h, 2, or 3 (250 μL) in 0.1 N NaOAc maintained at room temperature for 10 min (final concentration: 111 μM, pH 5.0). Radiolabeling yields were determined after holding the reaction mixture at room temperature for 5-10 min. Radiochemical yields for [⁶⁸Ga]1a-h, [⁶⁸Ga]2, and [⁶⁸Ga]3 were determined by Macherey Nagel cellulose TLC plates (Polygram Cel 300) developed with a solvent mixture consisting of 2 parts, 0.1 N NaOAc (10 mL, pH 4.10, 88 mL acetone), and 1 part, 2,4-pentadione. The activity distribution on each TLC plate was measured by autoradiography using a Typhoon FLA 7000 laser scanner. The HPLC analysis was performed using a C18 column (Supelco Ascentis C18 150×4.6 mm 5, MeOH: 0.1% TFA in H$_2$O (gradient: 0 min, 100% 0.1% TFA in H$_2$O; 6 min, 0% 0.1% TFA in H$_2$O, flow rate, 2 mL/min).

For in vivo imaging studies, a larger amount of $^{68}$Ga labeled agents was needed. The labeling was performed in an aqueous NaOAc buffer (200 μL, 2.0 M) by adding a ligand solution (200 μL, 200 M in 0.1 N NaOAc) to a 68Ga solution (400 μL in 0.6 N HCl) in H$_2$O (200 μL). The final pH of the solution was 4.10.

Example 6

In Vivo Biodistribution in Mice

Biodistribution experiments were performed by intravenously administering $^{68}$Ga labeled 1a-h, 2, 3, BPAMD, and [$^{18}$F]NaF into normal, healthy male CD-1 mice (25-30 g). The injection activity was 20-30 μCi/animal. Animals were sacrificed at 2, 30, 60, and 120 min post injection. Organs of interest were harvested, weighed, and counts of radioactivity were measured by a gamma counter. The biodistribution of each sample was calculated as a percentage of the injected dose per gram of wet tissue weight (% ID/g). Tibia and femur bones were harvested and counted as bone samples.

Example 7

In Vitro Binding to Hydroxyapatite

Hydroxyapatite (20 mg, Sigma-Aldrich, reagent grade powder) was incubated in isotonic saline (1 mL) for 24 h. Subsequently, either $^{68}$Ga labeled 1a-h, 2, 3, BPAMD, or [$^{18}$F]NaF (1 μCi) was added to the hydroxyapatite suspension. After vortexing for 10 seconds, the suspension was incubated for 10 min at room temperature. The samples were then centrifuged at 10,000 rpm for 3 min and the supernatant was removed. The hydroxyapatite fraction was washed twice with saline (1 mL). Radioactivity in the combined supernatants and the hydroxyapatite fraction was measured using a gamma counter. The proportion of the $^{68}$Ga complex binding to hydroxyapatite was determined as percent of $^{68}$Ga absorbed to hydroxyapatite.

Example 8

Micro-PET Imaging Studies in Mice

[$^{68}$Ga]1a, [$^{68}$Ga]BPAMD and [$^{18}$F]NaF were tested in normal CD-1 male mice. [$^{68}$Ga]1g was tested in PSMA expressing LNCaP tumor bearing nude mice. Mice received 300-500 uCi radiotracer through a tail vein injection. PET imaging was performed under isoflurane anaesthesia (2% isoflurane, 1.5 L/min oxygen). The microPET imaging was performed with a small animal PET (Mosaic by Phillips, USA). During PET measurements, the animals were placed in the prone position. At 60 min post injection of the radiotracer, data acquisition was performed for 15 min.

Results

Synthesis

Synthesis of target compounds 1a-h, 2, and 3 were prepared by the reactions described in Schemes 1, 3, and 4. In order to prepare a protected compound 5, compound 4 was synthesized by a Mannich reaction with di-tert-butyl 2,2'-(ethane-1,2-diylbis(azanediyl))di acetate and methyl 3-(4-hydroxyphenyl)propanoate in excellent yield (84.5%). The carboxylic functional groups of 4 were separately protected by either an OtBu or OMe ester group, The methyl ester of compound 4 was selectively removed by NaOH hydrolysis to give compound 5 (94.7% yield). To make bisphosphonate derivatives, compound 5 was activated with EDCI and HOBt in DMF. The addition of tetraethyl aminomethylenediphosphonate gave the desired protected bisphosponate, 6a, in 44.3% yield. After treatment of 6a with trimethylbromosilane at room temperature overnight, removal of the solvent, and stirring in TFA for another night, the phosphonate ethyl ester groups and the t-butyl esters were removed simultaneously to give 1a (82.3% yield).

In order to produce 6c which bears a different group, an amino acid group was added to the protected HBED-CC 5 core first in order to produce an intermediate, because tetraethyl aminomethylenediphosphonate has a greater steric hindrance compared to the protected amino acid. A further intermediate reaction was conducted with tetraethyl aminomethylenediphosphonate to yield 6c. After treatment of 6c with trimethylbromosilane and TFA using a similar method to 1a, 6c was obtained in 80.1% yield. This approach was simple and versatile. Using a similar reaction sequence and a different derivatives, 1b-h were prepared. The synthesis of the desired bisphosphonates was successfully accomplished and easily controlled.

Radiolabeling of 1a-h, 2 and 3 Using $^{68}$GaCl$_3$

The preparation of radioactive [$^{68}$Ga]1a-h, [68Ga]2, and [$^{68}$Ga]3 was accomplished by mixing $^{68}$GaCl$_3$ in 0.05 M HCl with a suitable amount of precursor 1a-h, 2, or 3 in a 0.1 N NaOAc solution and maintaining the reaction at room temperature for 10 minutes. The radiochemical purity was measured by both TLC and HPLC methods. TLC results showed that the $^{68}$Ga complex exhibited Rf=0-0.1 and the free $^{68}$Ga$^{3+}$ product displayed Rf=0.8-0.9. As expected, HPLC analysis revealed multiple peaks for the Ga-HBED-CC-BP complexes. [$^{68}$Ga]1a-h, [$^{68}$Ga]2, and [$^{68}$Ga]3 showed a retention time of 4-5.5 min, while free $^{68}$GaCl$_3$ showed a retention time of 1 min.

The [$^{nat}$Ga]1a ligand was synthesized by reacting 1a with GaCl$_3$ in DMSO at room temperature overnight. The compound was then characterized spectroscopically.

Importantly, the preparation of [$^{68}$Ga]1a-h and [$^{68}$Ga]2 can be readily achieved at room temperature in 5 to 10 minutes at a ligand concentration of 111 μM, whereas the preparation of the known agent, [$^{68}$Ga]BPAMD, required heating at 80-90° C. for 5-10 min. The new bone imaging agents, [$^{68}$Ga]1a-h and [$^{68}$Ga]2, may provide a kit formulation, which can be conveniently adopted in nuclear medicine clinics without the need for heating, cooling, and a nearby cyclotron for production of [$^{18}$F]NaF.

A proper metal ion, such as Lu(III) chloride, can be identified for selective radiolabeling of the DOTA moiety of compound 1h based on difference in the metal's complexing capability and stability constants for metal complexes with DOTA and HBED. The conditions for the selective radiolabeling can be routinely optimized under a similar reaction condition as described above for $^{68}$Ga(III), except that the reception may require heating the reaction mixture of $^{177}$Lu (III) and the ligand, 1h.

In Vivo Biodistribution in Normal Mice

To evaluate bone uptake, $^{68}$Ga labeled complexes and known bone imaging agent, [$^{18}$F]NaF, were injected intravenously into normal mice. The results of a biodistribution study displayed in Table 4 show that the bone uptake for [$^{18}$F]NaF, [$^{68}$Ga]1a, and [$^{68}$Ga]2 at 60 min post iv injection in normal mice was 24.6±3.2, 23.5±1.4 and 19.7±4.2 (% dose/g), respectively. The bone/muscle indicating signal/background ratio in normal mice for [$^{18}$F]NaF, [$^{68}$Ga]1a, and [$^{68}$Ga]2 at 60 min post iv injection was 291, 94.5 and 82.7, respectively. It is demonstrated that [$^{68}$Ga]BPAMD exhibited less bone uptake and retention as compared to the new agents, [$^{68}$Ga]1a-h and [$^{68}$Ga]2. In particular, [$^{68}$Ga]1a, [$^{68}$Ga]1g, [$^{68}$Ga]1h and [$^{68}$Ga]2 demonstrated excellent bone uptake and fast kidney excretion compared to that observed for [18F]NaF. The results suggest that [$^{68}$Ga]1a, [$^{68}$Ga]1g, [$^{68}$Ga]1h and [$^{68}$Ga]2, will likely be comparable in imaging human bone uptake and perhaps bone metastasis, similar to the current agent of choice [$^{18}$F]NaF.

TABLE 4a-g

Biodistribution of bone imaging agents : [$^{18}$F]NaF, [$^{68}$Ga]BPAMD, [$^{68}$Ga]1a-h, [$^{177}$Lu]1h, [$^{68}$Ga]2, [$^{68}$Ga]3, and [$^{68}$Ga]HBED-CC in normal CD-1 male mice (% dose/g, Avg ± SD of n = 3)

a. Radiotracer: [$^{18}$F]NaF

| | 2 min | 30 min | 60 min | 120 min |
|---|---|---|---|---|
| Blood | 5.56 ± 0.37 | 0.64 ± 0.08 | 0.15 ± 0.01 | 0.03 ± 0.00 |
| Heart | 2.80 ± 0.24 | 0.96 ± 0.23 | 0.18 ± 0.02 | 0.04 ± 0.00 |
| Muscle | 1.50 ± 0.06 | 0.33 ± 0.11 | 0.09 ± 0.02 | 0.04 ± 0.04 |
| Lung | 3.37 ± 0.17 | 0.55 ± 0.11 | 0.14 ± 0.01 | 0.04 ± 0.01 |
| Kidney | 10.4 ± 1.22 | 1.70 ± 0.62 | 0.68 ± 0.36 | 0.57 ± 0.43 |
| Spleen | 2.33 ± 0.14 | 0.93 ± 0.56 | 0.12 ± 0.02 | 0.03 ± 0.01 |
| Pancreas | 1.76 ± 0.07 | 0.42 ± 0.27 | 0.07 ± 0.00 | 0.02 ± 0.00 |
| Liver | 2.56 ± 0.24 | 0.65 ± 0.17 | 0.13 ± 0.01 | 0.03 ± 0.01 |
| Skin | 2.35 ± 0.45 | 0.51 ± 0.11 | 0.11 ± 0.02 | 0.03 ± 0.00 |
| Brain | 0.22 ± 0.07 | 0.10 ± 0.02 | 0.06 ± 0.01 | 0.04 ± 0.00 |
| Bone | 10.8 ± 0.51 | 24.2 ± 2.71 | 24.6 ± 3.18 | 25.2 ± 3.89 | b. Radiotracer: [$^{68}$Ga]BPAMD

| | 2 min | 30 min | 60 min | 120 min |
|---|---|---|---|---|
| Blood | 9.45 ± 0.55 | 1.02 ± 0.19 | 0.93 ± 0.06 | 0.90 ± 0.41 |
| Heart | 2.74 ± 0.23 | 0.29 ± 0.02 | 0.37 ± 0.06 | 0.26 ± 0.07 |
| Muscle | 1.63 ± 0.35 | 0.55 ± 0.11 | 0.31 ± 0.04 | 0.29 ± 0.06 |
| Lung | 4.58 ± 0.36 | 0.50 ± 0.16 | 0.51 ± 0.09 | 0.45 ± 0.10 |
| Kidney | 22.1 ± 8.80 | 1.46 ± 0.19 | 2.88 ± 1.51 | 1.09 ± 0.26 |
| Spleen | 1.90 ± 0.14 | 0.22 ± 0.14 | 0.21 ± 0.02 | 0.25 ± 0.08 |
| Pancreas | 1.73 ± 0.11 | 0.27 ± 0.14 | 0.30 ± 0.02 | 0.33 ± 0.07 |
| Liver | 1.92 ± 0.31 | 0.22 ± 0.02 | 0.25 ± 0.03 | 0.31 ± 0.11 |
| Skin | 2.57 ± 0.53 | 0.39 ± 0.15 | 0.60 ± 0.08 | 0.55 ± 0.04 |
| Brain | 0.26 ± 0.01 | 0.06 ± 0.02 | 0.04 ± 0.00 | 0.03 ± 0.01 |
| Bone | 7.07 ± 0.94 | 10.5 ± 0.6 | 9.21 ± 0.90 | 9.62 ± 0.71 | c. Radiotracers: [$^{68}$Ga]1a

| | 2 min | 30 min | 60 min | 120 min |
|---|---|---|---|---|
| Blood | 9.39 ± 0.93 | 0.45 ± 0.10 | 0.20 ± 0.06 | 0.07 ± 0.03 |
| Heart | 3.28 ± 0.13 | 0.22 ± 0.02 | 0.12 ± 0.02 | 0.07 ± 0.01 |
| Muscle | 1.80 ± 0.16 | 0.17 ± 0.03 | 0.08 ± 0.01 | 0.05 ± 0.01 |
| Lung | 4.28 ± 0.21 | 0.38 ± 0.03 | 0.21 ± 0.03 | 0.12 ± 0.03 |
| Kidney | 31.2 ± 1.92 | 1.54 ± 0.29 | 1.63 ± 0.71 | 0.92 ± 0.10 |
| Spleen | 1.89 ± 0.20 | 0.17 ± 0.01 | 0.10 ± 0.02 | 0.09 ± 0.03 |
| Pancreas | 1.58 ± 0.10 | 0.30 ± 0.27 | 0.09 ± 0.02 | 0.05 ± 0.01 |
| Liver | 1.95 ± 0.15 | 0.32 ± 0.20 | 0.17 ± 0.01 | 0.14 ± 0.02 |
| Skin | 2.18 ± 0.28 | 0.42 ± 0.12 | 0.19 ± 0.05 | 0.13 ± 0.03 |
| Brain | 0.31 ± 0.10 | 0.02 ± 0.01 | 0.02 ± 0.01 | 0.01 ± 0.00 |
| Bone | 8.60 ± 0.85 | 16.0 ± 1.22 | 23.5 ± 1.42 | 23.9 ± 1.99 | d. Radiotracers: [$^{68}$Ga]1b

| | 2 min | 30 min | 60 min | 120 min |
|---|---|---|---|---|
| Blood | 9.22 ± 0.83 | 0.83 ± 0.04 | 0.39 ± 0.06 | 0.21 ± 0.06 |
| Heart | 3.01 ± 0.23 | 0.62 ± 0.04 | 0.37 ± 0.02 | 0.28 ± 0.04 |
| Muscle | 1.79 ± 0.28 | 0.24 ± 0.03 | 0.13 ± 0.01 | 0.09 ± 0.01 |
| Lung | 5.11 ± 0.28 | 1.31 ± 0.29 | 0.96 ± 0.05 | 0.86 ± 0.03 |
| Kidney | 18.5 ± 2.45 | 3.21 ± 1.59 | 2.65 ± 0.44 | 2.71 ± 0.17 |
| Spleen | 2.03 ± 0.13 | 0.75 ± 0.22 | 0.66 ± 0.15 | 0.53 ± 0.04 |
| Pancreas | 1.51 ± 0.06 | 0.24 ± 0.02 | 0.11 ± 0.01 | 0.08 ± 0.01 |
| Liver | 2.58 ± 0.22 | 1.20 ± 0.10 | 1.15 ± 0.13 | 1.22 ± 0.07 |
| Skin | 2.55 ± 0.58 | 0.60 ± 0.02 | 0.26 ± 0.04 | 0.18 ± 0.01 |
| Brain | 0.20 ± 0.04 | 0.03 ± 0.01 | 0.02 ± 0.01 | 0.02 ± 0.01 |
| Bone | 8.34 ± 0.88 | 16.6 ± 1.37 | 19.4 ± 2.05 | 17.1 ± 3.70 | e. Radiotracers: [$^{68}$Ga]1c

| | 2 min | 30 min | 60 min | 120 min |
|---|---|---|---|---|
| Blood | 11.7 ± 0.55 | 1.34 ± 0.32 | 0.64 ± 0.17 | 0.41 ± 0.07 |
| Heart | 4.57 ± 0.45 | 0.49 ± 0.07 | 0.24 ± 0.08 | 0.19 ± 0.03 |
| Muscle | 1.68 ± 0.11 | 0.23 ± 0.05 | 0.14 ± 0.01 | 0.16 ± 0.01 |
| Lung | 5.66 ± 0.24 | 0.84 ± 0.11 | 0.42 ± 0.08 | 0.31 ± 0.06 |
| Kidney | 27.7 ± 5.46 | 2.58 ± 0.05 | 1.88 ± 0.10 | 2.05 ± 0.27 |
| Spleen | 3.41 ± 0.08 | 0.97 ± 0.01 | 0.74 ± 0.10 | 0.71 ± 0.29 |
| Pancreas | 1.99 ± 0.23 | 0.39 ± 0.05 | 0.23 ± 0.02 | 0.20 ± 0.03 |
| Liver | 4.78 ± 0.18 | 2.21 ± 0.27 | 1.85 ± 0.11 | 1.99 ± 0.09 |
| Skin | 2.05 ± 0.16 | 0.53 ± 0.18 | 0.33 ± 0.03 | 0.31 ± 0.04 |
| Brain | 0.27 ± 0.06 | 0.05 ± 0.02 | 0.03 ± 0.01 | 0.02 ± 0.01 |
| Bone | 8.40 ± 1.32 | 11.3 ± 0.26 | 14.7 ± 0.66 | 16.1 ± 2.71 | f. Radiotracers: [$^{68}$Ga]1d

| | 2 min | 30 min | 60 min | 120 min |
|---|---|---|---|---|
| Blood | 9.08 ± 0.58 | 0.53 ± 0.13 | 0.10 ± 0.01 | 0.06 ± 0.02 |
| Heart | 2.99 ± 0.26 | 0.26 ± 0.06 | 0.08 ± 0.01 | 0.06 ± 0.01 |
| Muscle | 1.72 ± 0.15 | 0.24 ± 0.06 | 0.06 ± 0.00 | 0.04 ± 0.01 |
| Lung | 4.83 ± 0.25 | 0.45 ± 0.10 | 0.17 ± 0.01 | 0.09 ± 0.02 |
| Kidney | 25.3 ± 3.89 | 2.14 ± 0.60 | 1.05 ± 0.17 | 0.91 ± 0.15 |
| Spleen | 1.72 ± 0.24 | 0.21 ± 0.07 | 0.06 ± 0.00 | 0.05 ± 0.01 |
| Pancreas | 1.53 ± 0.14 | 0.21 ± 0.12 | 0.06 ± 0.01 | 0.04 ± 0.01 |
| Liver | 1.89 ± 0.16 | 0.26 ± 0.09 | 0.12 ± 0.01 | 0.10 ± 0.01 |
| Skin | 2.39 ± 0.13 | 0.42 ± 0.10 | 0.13 ± 0.01 | 0.09 ± 0.01 |
| Brain | 0.29 ± 0.05 | 0.03 ± 0.00 | 0.01 ± 0.00 | 0.00 ± 0.00 |
| Bone | 10.1 ± 2.05 | 15.3 ± 1.26 | 14.7 ± 0.50 | 17.0 ± 1.10 | g. Radiotracers: [$^{68}$Ga]1e

| | 2 min | 30 min | 60 min | 120 min |
|---|---|---|---|---|
| Blood | 8.31 ± 0.57 | 0.57 ± 0.12 | 0.11 ± 0.02 | 0.08 ± 0.02 |
| Heart | 2.55 ± 0.06 | 0.26 ± 0.04 | 0.08 ± 0.01 | 0.06 ± 0.01 |
| Muscle | 1.71 ± 0.19 | 0.25 ± 0.03 | 0.06 ± 0.00 | 0.04 ± 0.01 |
| Lung | 4.00 ± 0.20 | 0.42 ± 0.08 | 0.15 ± 0.01 | 0.12 ± 0.02 |
| Kidney | 24.8 ± 3.02 | 2.26 ± 0.27 | 2.12 ± 0.55 | 1.41 ± 0.28 |
| Spleen | 1.72 ± 0.19 | 0.19 ± 0.02 | 0.09 ± 0.01 | 0.06 ± 0.01 |
| Pancreas | 1.27 ± 0.07 | 0.17 ± 0.05 | 0.06 ± 0.01 | 0.04 ± 0.01 |
| Liver | 1.90 ± 0.13 | 0.27 ± 0.01 | 0.14 ± 0.01 | 0.14 ± 0.02 |
| Skin | 2.54 ± 0.26 | 0.86 ± 0.22 | 0.12 ± 0.01 | 0.12 ± 0.03 |
| Brain | 0.20 ± 0.04 | 0.02 ± 0.01 | 0.01 ± 0.00 | 0.01 ± 0.01 |
| Bone | 8.82 ± 0.77 | 16.5 ± 0.56 | 14.9 ± 1.45 | 17.6 ± 2.61 | h. Radiotracers: [$^{68}$Ga]1f

| | 2 min | 30 min | 60 min | 120 min |
|---|---|---|---|---|
| Blood | 8.98 ± 0.68 | 0.52 ± 0.05 | 0.18 ± 0.04 | 0.09 ± 0.01 |
| Heart | 3.53 ± 0.57 | 0.23 ± 0.01 | 0.11 ± 0.01 | 0.07 ± 0.01 |
| Muscle | 2.10 ± 0.12 | 0.23 ± 0.01 | 0.06 ± 0.00 | 0.04 ± 0.01 |
| Lung | 5.01 ± 0.81 | 0.42 ± 0.03 | 0.21 ± 0.01 | 0.13 ± 0.01 |
| Kidney | 24.7 ± 3.13 | 2.05 ± 0.52 | 1.59 ± 0.72 | 1.08 ± 0.20 |
| Spleen | 2.20 ± 0.26 | 0.22 ± 0.03 | 0.12 ± 0.04 | 0.08 ± 0.01 |
| Pancreas | 1.96 ± 0.15 | 0.15 ± 0.01 | 0.08 ± 0.02 | 0.04 ± 0.00 |
| Liver | 2.43 ± 0.27 | 0.28 ± 0.02 | 0.20 ± 0.02 | 0.19 ± 0.01 |
| Skin | 2.62 ± 0.11 | 0.49 ± 0.04 | 0.15 ± 0.01 | 0.09 ± 0.01 |
| Brain | 0.22 ± 0.00 | 0.02 ± 0.00 | 0.01 ± 0.00 | 0.01 ± 0.01 |
| Bone | 8.62 ± 0.23 | 16.8 ± 1.66 | 14.4 ± 3.01 | 16.7 ± 1.12 |

TABLE 4a-g-continued

Biodistribution of bone imaging agents : [$^{18}$F]NaF, [$^{68}$Ga]BPAMD, [$^{68}$Ga]1a-h, [$^{177}$Lu]1h, [$^{68}$Ga]2, [$^{68}$Ga]3, and [$^{68}$Ga]HBED-CC in normal CD-1 male mice (% dose/g, Avg ± SD of n = 3)

i. Radiotracers: [$^{68}$Ga]1g

|  | 2 min | 30 min | 60 min | 120 min |
|---|---|---|---|---|
| Blood | 8.34 ± 0.51 | 0.56 ± 0.10 | 0.28 ± 0.05 | 0.17 ± 0.03 |
| Heart | 3.13 ± 0.15 | 0.45 ± 0.07 | 0.32 ± 0.03 | 0.20 ± 0.03 |
| Muscle | 2.19 ± 0.11 | 0.35 ± 0.02 | 0.21 ± 0.02 | 0.17 ± 0.04 |
| Lung | 4.19 ± 0.50 | 1.02 ± 0.13 | 0.58 ± 0.02 | 0.47 ± 0.04 |
| Kidney | 35.3 ± 3.75 | 77.1 ± 8.24 | 78.4 ± 7.11 | 70.3 ± 8.29 |
| Spleen | 2.50 ± 0.41 | 2.09 ± 0.75 | 0.91 ± 0.13 | 0.87 ± 0.20 |
| Pancreas | 1.69 ± 0.13 | 0.69 ± 0.02 | 0.37 ± 0.07 | 0.34 ± 0.03 |
| Liver | 1.73 ± 0.09 | 0.27 ± 0.02 | 0.18 ± 0.01 | 0.18 ± 0.02 |
| Skin | 2.97 ± 0.14 | 0.65 ± 0.05 | 0.42 ± 0.06 | 0.29 ± 0.06 |
| Brain | 0.21 ± 0.03 | 0.03 ± 0.00 | 0.03 ± 0.01 | 0.02 ± 0.00 |
| Bone | 8.13 ± 1.87 | 16.3 ± 0.68 | 15.1 ± 1.04 | 17.0 ± 0.05 | j. Radiotracers: [$^{68}$Ga]1h

|  | 2 min | 30 min | 60 min | 120 min |
|---|---|---|---|---|
| Blood | 9.69 ± 1.49 | 0.45 ± 0.07 | 0.11 ± 0.05 | 0.04 ± 0.01 |
| Heart | 3.10 ± 0.35 | 0.24 ± 0.12 | 0.08 ± 0.01 | 0.05 ± 0.01 |
| Muscle | 1.92 ± 0.14 | 0.14 ± 0.04 | 0.05 ± 0.01 | 0.03 ± 0.00 |
| Lung | 4.35 ± 0.52 | 0.31 ± 0.05 | 0.14 ± 0.03 | 0.10 ± 0.01 |
| Kidney | 18.2 ± 1.65 | 2.07 ± 0.62 | 1.13 ± 0.08 | 1.67 ± 0.54 |
| Spleen | 1.91 ± 0.48 | 0.13 ± 0.03 | 0.07 ± 0.01 | 0.07 ± 0.01 |
| Pancreas | 1.48 ± 0.27 | 0.09 ± 0.03 | 0.05 ± 0.02 | 0.04 ± 0.01 |
| Liver | 1.99 ± 0.29 | 0.15 ± 0.05 | 0.07 ± 0.01 | 0.09 ± 0.04 |
| Skin | 2.31 ± 0.25 | 0.39 ± 0.13 | 0.11 ± 0.02 | 0.07 ± 0.01 |
| Brain | 0.24 ± 0.03 | 0.02 ± 0.01 | 0.01 ± 0.00 | 0.01 ± 0.01 |
| Bone | 8.31 ± 0.84 | 12.1 ± 0.84 | 11.9 ± 1.31 | 12.0 ± 0.82 | k. Radiotracers: [$^{177}$Lu]1h

|  | 0.5 hr | 1 hr | 6 hr | 24 hr |
|---|---|---|---|---|
| Blood | 0.54 ± 0.11 | 0.12 ± 0.02 | 0.016 ± 0.007 | 0.003 ± 0.001 |
| Heart | 0.23 ± 0.05 | 0.08 ± 0.02 | 0.024 ± 0.005 | 0.014 ± 0.003 |
| Muscle | 0.39 ± 0.24 | 0.06 ± 0.01 | 0.031 ± 0.011 | 0.021 ± 0.005 |
| Lung | 1.35 ± 1.52 | 0.20 ± 0.05 | 0.062 ± 0.006 | 0.040 ± 0.003 |
| Kidney | 1.21 ± 0.94 | 1.48 ± 0.60 | 0.686 ± 0.191 | 0.411 ± 0.125 |
| Spleen | 0.15 ± 0.04 | 0.07 ± 0.01 | 0.038 ± 0.005 | 0.034 ± 0.005 |
| Pancreas | 0.15 ± 0.03 | 0.07 ± 0.02 | 0.021 ± 0.001 | 0.013 ± 0.005 |
| Liver | 0.20 ± 0.03 | 0.13 ± 0.03 | 0.088 ± 0.021 | 0.068 ± 0.013 |
| Skin | 0.41 ± 0.12 | 0.11 ± 0.03 | 0.052 ± 0.006 | 0.042 ± 0.008 |
| Brain | 0.03 ± 0.01 | 0.01 ± 0.00 | 0.003 ± 0.003 | 0.014 ± 0.016 |
| Bone | 12.4 ± 1.19 | 11.4 ± 0.31 | 12.7 ± 0.90 | 11.6 ± 1.14 | l. Radiotracers: [$^{68}$Ga]2

|  | 2 min | 30 min | 60 min | 120 min |
|---|---|---|---|---|
| Blood | 9.97 ± 1.40 | 0.73 ± 0.28 | 0.47 ± 0.08 | 0.31 ± 0.09 |
| Heart | 4.13 ± 0.30 | 0.99 ± 0.13 | 0.57 ± 0.13 | 0.42 ± 0.08 |
| Muscle | 2.26 ± 0.34 | 0.32 ± 0.05 | 0.24 ± 0.04 | 0.23 ± 0.05 |
| Lung | 5.47 ± 0.57 | 0.96 ± 0.23 | 0.58 ± 0.09 | 0.40 ± 0.05 |
| Kidney | 19.4 ± 1.38 | 2.98 ± 1.13 | 2.61 ± 0.95 | 2.86 ± 1.16 |
| Spleen | 2.08 ± 0.22 | 0.48 ± 0.09 | 0.43 ± 0.05 | 0.43 ± 0.24 |
| Pancreas | 2.05 ± 0.23 | 0.36 ± 0.17 | 0.27 ± 0.01 | 0.31 ± 0.11 |
| Liver | 2.67 ± 0.12 | 0.44 ± 0.09 | 0.43 ± 0.03 | 0.40 ± 0.03 |
| Skin | 3.19 ± 0.45 | 0.71 ± 0.13 | 0.38 ± 0.05 | 0.33 ± 0.06 |
| Brain | 0.30 ± 0.02 | 0.03 ± 0.00 | 0.02 ± 0.00 | 0.02 ± 0.00 |
| Bone | 11.0 ± 1.95 | 18.8 ± 2.82 | 19.7 ± 4.17 | 23.9 ± 5.54 | m. Radiotracers: [$^{68}$Ga]3

|  | 2 min | 30 min | 60 min | 120 min |
|---|---|---|---|---|
| Blood | 8.33 ± 0.23 | 1.92 ± 0.15 | 0.70 ± 0.13 | 0.37 ± 0.07 |
| Heart | 3.45 ± 0.25 | 2.02 ± 0.97 | 1.16 ± 0.73 | 1.05 ± 0.11 |
| Muscle | 1.62 ± 0.47 | 0.68 ± 0.09 | 0.57 ± 0.14 | 0.28 ± 0.04 |
| Lung | 71.6 ± 6.33 | 15.6 ± 1.39 | 41.3 ± 5.15 | 34.8 ± 1.90 |
| Kidney | 12.2 ± 1.51 | 17.1 ± 0.70 | 7.99 ± 1.08 | 8.99 ± 0.20 |
| Spleen | 12.8 ± 4.35 | 8.33 ± 2.22 | 10.3 ± 2.65 | 15.7 ± 1.59 |
| Pancreas | 1.73 ± 0.08 | 1.07 ± 1.04 | 0.26 ± 0.02 | 0.25 ± 0.03 |
| Liver | 19.7 ± 1.05 | 9.86 ± 0.66 | 23.5 ± 3.13 | 25.4 ± 2.80 |
| Skin | 1.24 ± 0.01 | 1.10 ± 0.18 | 0.41 ± 0.02 | 0.33 ± 0.06 |
| Brain | 0.28 ± 0.03 | 0.06 ± 0.01 | 0.06 ± 0.01 | 0.05 ± 0.01 |
| Bone | 4.17 ± 0.35 | 9.26 ± 1.45 | 9.26 ± 1.13 | 10.6 ± 0.85 | n. Radiotracers: [$^{68}$Ga]HBED-CC

|  | 2 min | 30 min | 60 min | 120 min |
|---|---|---|---|---|
| Blood | 7.66 ± 0.75 | 0.83 ± 0.09 | 0.14 ± 0.04 | 0.01 ± 0.00 |
| Heart | 2.74 ± 0.34 | 0.34 ± 0.06 | 0.17 ± 0.11 | 0.09 ± 0.00 |
| Muscle | 2.30 ± 0.13 | 0.32 ± 0.06 | 0.11 ± 0.04 | 0.05 ± 0.02 |
| Lung | 4.27 ± 0.34 | 0.58 ± 0.07 | 0.19 ± 0.04 | 0.07 ± 0.02 |
| Kidney | 27.2 ± 0.64 | 3.22 ± 0.41 | 0.91 ± 0.32 | 0.08 ± 0.05 |
| Spleen | 1.69 ± 0.18 | 0.26 ± 0.04 | 0.12 ± 0.02 | 0.13 ± 0.03 |
| Pancreas | 1.60 ± 0.12 | 0.26 ± 0.01 | 0.13 ± 0.05 | 0.07 ± 0.01 |
| Liver | 1.75 ± 0.08 | 0.38 ± 0.08 | 0.11 ± 0.02 | 0.04 ± 0.02 |
| Skin | 3.18 ± 0.43 | 0.64 ± 0.08 | 0.09 ± 0.07 | 0.03 ± 0.01 |
| Brain | 0.29 ± 0.08 | 0.04 ± 0.01 | 0.02 ± 0.01 | 0.02 ± 0.00 |
| Bone | 1.85 ± 0.05 | 0.28 ± 0.06 | 0.25 ± 0.16 | 0.18 ± 0.06 |

TABLE 5

Comparison of a) bone to blood ratio and b) bone to muscle ratio in normal CD-1 male mice after an iv injection

|  | 2 min | 30 min | 60 min | 120 min |
|---|---|---|---|---|
| a) bone to blood ratio | | | | |
| [$^{18}$F]NaF | 1.9 | 38 | 161 | 760 |
| [$^{68}$Ga]BPAMD | 0.8 | 10 | 10 | 11 |
| [$^{68}$Ga]1a | 0.9 | 36 | 118 | 320 |
| [$^{68}$Ga]1b | 0.9 | 20 | 50 | 82 |
| [$^{68}$Ga]1c | 0.7 | 8 | 23 | 39 |
| [$^{68}$Ga]1d | 1.1 | 29 | 144 | 278 |
| [$^{68}$Ga]1e | 1 | 29 | 138 | 230 |
| [$^{68}$Ga]1f | 1 | 33 | 78 | 180 |
| [$^{68}$Ga]1g | 0.97 | 29 | 53 | 98 |
| [$^{68}$Ga]1h | 0.9 | 27 | 112 | 305 |
| [$^{177}$Lu]1h |  | 24 | 97 | 909[a] |
|  |  |  |  | 4312[b] |
| [$^{68}$Ga]2 | 1.1 | 26 | 42 | 77 |
| [$^{68}$Ga]3 | 0.5 | 4.8 | 13 | 29 |
| [$^{68}$Ga]HBED-CC | 0.2 | 0.3 | 1.7 | 12 |
| b) bone to muscle ratio | | | | |
| [$^{18}$F]NaF | 7.2 | 73 | 281 | 593 |
| [$^{68}$Ga]BPAMD | 4.3 | 19 | 30 | 33 |
| [$^{68}$Ga]1a | 4.8 | 96 | 291 | 447 |
| [$^{68}$Ga]1b | 4.7 | 68 | 147 | 197 |
| [$^{68}$Ga]1c | 5 | 49 | 102 | 103 |
| [$^{68}$Ga]1d | 5.9 | 64 | 235 | 417 |
| [$^{68}$Ga]1e | 5 | 67 | 258 | 411 |
| [$^{68}$Ga]1f | 4 | 74 | 222 | 374 |
| [$^{68}$Ga]1g | 3.71 | 46 | 74 | 98 |
| [$^{68}$Ga]1h | 4.3 | 85 | 233 | 383 |
| [$^{177}$Lu]1h |  | 41 | 200 | 454[a] |
|  |  |  |  | 572[b] |
| [$^{68}$Ga]2 | 4.9 | 58 | 83 | 103 |
| [$^{68}$Ga]3 | 2.6 | 14 | 16 | 39 |
| [$^{68}$Ga]HBED-CC | 0.8 | 0.9 | 2.3 | 3.3 |

[a] 6 hr post-injection,
[b] 24 hr post-injection

Theranostic Agent, 1h: [$^{68}$Ga]1h and [$^{177}$Lu]1h 1h, a derivative containing DOTA chelating group for other therapeutic metals, such as $^{177}$Lu and $^{90}$Y, was also prepared as radionuclide therapeutic agents for bone metastasis. The results of a biodistribution study displayed in Table 4j-k showed that the bone uptake for [$^{68}$Ga]1h and [$^{177}$Lu]1h at 60 min post iv injection in normal mice was 11.9±1.3 and 11.4±0.3 (% dose/g), respectively. The bone to muscle ratio in normal mice for [$^{68}$Ga]1h and [$^{177}$Lu]1h at 60 min post iv injection was 233 and 200, respectively. The bone to blood ratio in normal mice for [$^{68}$Ga]1h and [$^{177}$Lu]1h at 60 min post iv injection was 112 and 97, respectively. Both radiotracers also displayed high hydroxyapatite binding (>90%). It is demonstrated that [$^{177}$Lu]1h exhibited excellent bone uptake, retention in bone and fast kidney excretion. No differences were observed between [$^{68}$Ga]1h and [$^{177}$Lu]1h. The DOTA containing agent, 1h can be employed as a theranostic agent for bone imaging with $^{68}$Ga labeling and for the palliation of metastatic bone pain when it is labeled with $^{177}$Lu or $^{90}$Y.

In Vitro Binding Studies Using Hydroxyapatite

To confirm the binding of [$^{68}$Ga]BPAMD, [$^{68}$Ga]1a-h, 2, and 3, as well as [$^{18}$F]NaF (a positive control), associated with active bone surfaces, these compounds were tested in a modeling system using hydroxyapatite aggregates. An in vitro binding study using the preformed hydroxyapatite aggregates showed that the bisphosphonates, [$^{68}$Ga]BPAMD, [$^{68}$Ga]1a-h, 2, and 3, as well as [$^{18}$F]NaF, displayed excellent binding in vitro (70-90% binding) as seen in Table 6. As expected, [$^{68}$Ga]HBED-CC, a chelator without bisphosphonate groups, showed very low hydroxyapatite aggregate binding in vitro (0.4±0.1% binding).

TABLE 6

In vitro hydroxyapatite binding

| Radioligand | Hydroxyapatite Binding (%) |
| --- | --- |
| [$^{18}$F]NaF | 78.4 ± 3.9 |
| [$^{68}$Ga]BPAMD | 90.6 ± 6.0 |
| [$^{68}$Ga]1a | 92.3 ± 1.1 |
| [$^{68}$Ga]1b | 91.7 ± 5.6 |
| [$^{68}$Ga]1c | 89.1 ± 1.0 |
| [$^{68}$Ga]1d | 95.1 ± 0.5 |
| [$^{68}$Ga]1e | 95.8 ± 0.9 |
| [$^{68}$Ga]1f | 96.4 ± 1.2 |
| [$^{68}$Ga]1g | 88.0 ± 10.5 |
| [$^{68}$Ga]1h | 96.7 ± 0.9 |
| [$^{177}$Lu]1h | 90.9 ± 1.1 |
| [$^{68}$Ga]2 | 90.8 ± 1.5 |
| [$^{68}$Ga]3 | 95.8 ± 0.1 |
| [$^{68}$Ga]HBED-CC | 0.4 ± 0.1 |

Each value represents the mean ± SD for n = 2-4 in triplicates.

Micro-PET Imaging of Mice for Bone

Micro-PET imaging studies in mice were successfully performed using [8F]NaF (0.3 mCi), [$^{68}$Ga]BPAMD (0.5 mCi), and [$^{68}$Ga]1a (0.5 mCi). Images acquisition was performed for 15 min at 60 min post-injection. The results clearly indicate that all agents localized in the spines of mice as seen in FIGS. 1A-1C, 2A-2C, and 3A-3C. Although it is likely that due to the size of mice, the individual sections of vertebrate were not visually separable, the bone uptake of the $^{68}$Ga labeled bisphosphonates and [$^{18}$F]NaF provided equally high bone uptake. The new bone imaging agent, [$^{68}$Ga]1a, will likely be suitable as a bone imaging agent, producing comparable images to those previously reported from [18F]NaF (FIGS. 1A-1C, 2A-2C, and 3A-3C).

Both HBED-CC-BP agents, [$^{68}$Ga]1a and [$^{68}$Ga]2 showed excellent bone uptake and retention comparable to that of [1F]NaF. Similar to that of [18F]NaF, mechanisms of uptake and retention of these new $^{68}$Ga labeled bisphosphonates are likely associated with the deposition of bisphosphonates via ion exchange reaction on the active bone surfaces (hydroxyapatite). Clearance rates of bone imaging agents from the kidney via glomerular filtration will determine the background clearance, thus strongly influence the signal to noise ratio. It is reported earlier that the fluoride ion showed a high rate of clearance and less reuptake in the kidney, therefore [$^{18}$F]NaF displayed the best bone vs. background ratio in vivo. The new [$^{68}$Ga]HBED bisphosphonate, [68Ga]1a-h and [$^{68}$Ga]2, probably share the same in vivo kinetics of mechanisms for bone uptake and retention. Adding additional amino acid, 2-glucoamine, Glu-NH—CO—NH-Lys(Ahx) or DOTA functional group, 1b-h, did not significantly changed in vivo kinetics of mechanisms for bone uptake and retention in normal mice.

Figure 4:
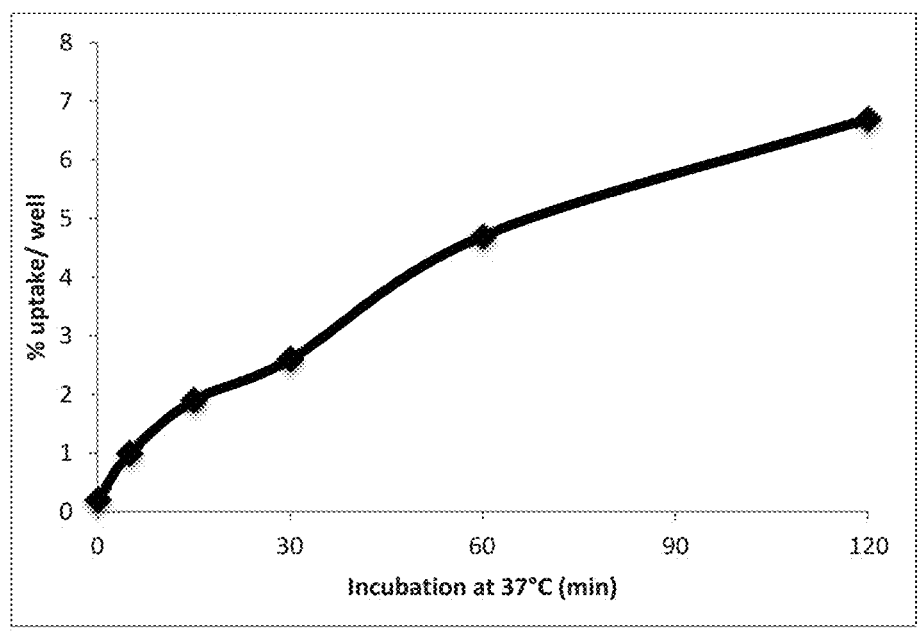
FIG. 4 depicts a graph that plots the time course of [$^{68}$Ga] 1g uptakes into PSMA expressing LNCaP cells (% uptake/well).
Figure 5:
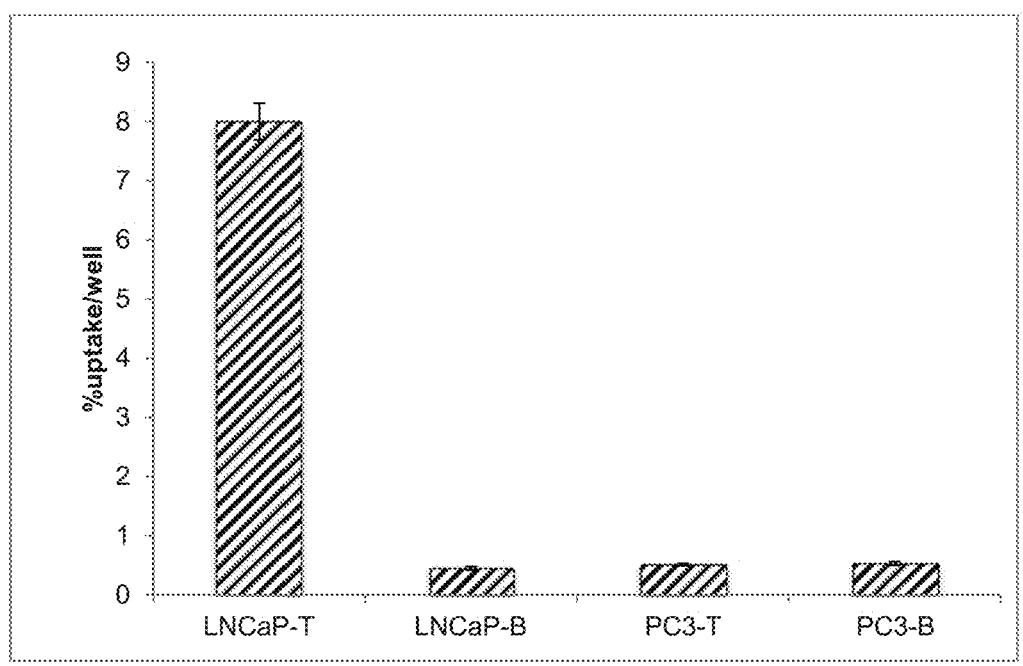
FIG. 5 depicts cell uptakes of [$^{68}$Ga]1g after 1 hr incubation at 37° C. (% uptake/well). The PSMA positive LNCaP cells displayed excellent uptake while the PSMA negative PC3 cells exhibited no uptake. Specific PSMA inhibitor, 2-PMPA (2-(phosphonomethyl)pentane-1,5-dioic acid), blocked the cell uptake to PSMA positive LNCaP cells. (T: Total uptake, B: Blocking by 2-PMPA).
Figures 6A, 6B, 6C:
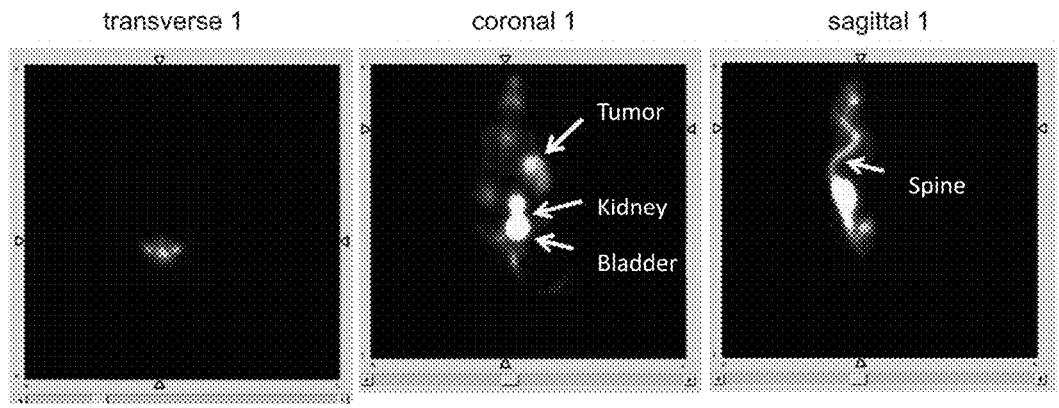
FIG. 6A-FIG. 6F depict transaxial, coronal, and sagittal sections of MicroPET images of a mouse after injection of [$^{68}$Ga]1g (500 μCi, 60 min post injection, 15 min scan).
Figures 6D, 6E, 6F:
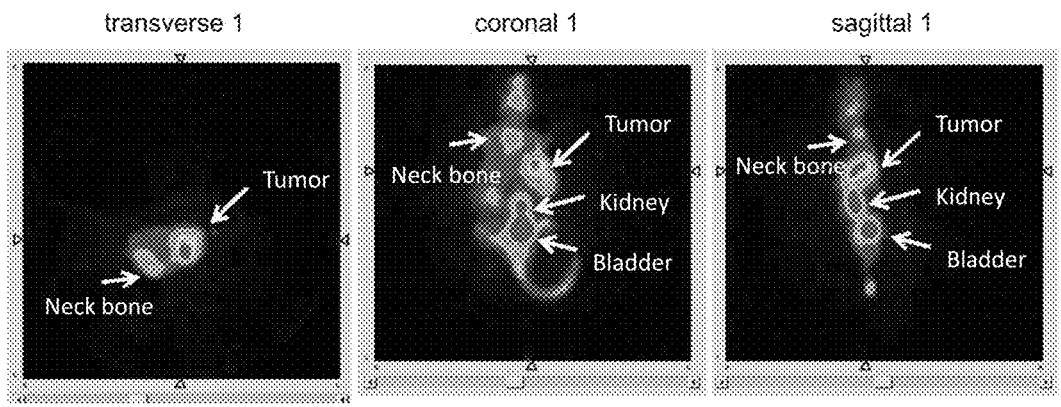

To test the selective binding of [$^{68}$Ga]1g to bone (by bisphosphonate group) and PSMA (by Glu-NH—CO—NH-Lys(Ahx) group) receptor, in vivo biodistribution in mice showed high bone uptakes similar to that of [$^{68}$Ga]1a and [$^{68}$Ga]2 (Table 4). In addition, [$^{68}$Ga]1g exhibited high kidney uptake and retention, as kidney is also an organ express high levels of PSMA receptors (Table 4-i). The biodistribution data in mice support the notion that [$^{68}$Ga]1g targets both bone and PSMA binding sites. In vitro binding studies were also performed using PSMA positive LNCaP cells and the PSMA negative PC3 cells. It was observed that [$^{68}$Ga]1g exhibited high cell uptake and retention only in LNCaP cells over expressing PSMA binding sites, suggesting that [$^{68}$Ga]1g binding to these cells was selective to the PSMA receptors on the membrane of cells (FIGS. 4 and 5).

Micro-PET Imaging of [$^{68}$Ga]1g in PSMA Expressing Tumor Bearing Mouse

The novel probe, [$^{68}$Ga]1g, was invented to target both bone metastasis and actively growing tumor which overexpress PSMA. The microPET image in mouse support the notion that [$^{68}$Ga]1g targets both bone and PSMA binding sites as shown in FIGS. 6A-6F.

While certain embodiments have been illustrated and described, it should be understood that changes and modifications can be made therein in accordance with ordinary skill in the art without departing from the technology in its broader aspects as defined in the following claims.

The present disclosure is not to be limited in terms of the particular embodiments described in this application. Modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

REFERENCES

[1] Iagaru A, Young P, Mittra E, Dick D W, Herfkens R, and Gambhir S S. Pilot prospective evaluation of 99mTc-

[1] MDP scintigraphy, 18F NaF PET/CT, 18F FDG PET/CT and whole-body MRI for detection of skeletal metastases. Clin. Nucl. Med. 2013; 38:e290-6.

[2] Jadvar H, Desai B, and Conti P S. Sodium 18F-fluoride PET/CT of bone, joint, and other disorders. Semin. Nucl. Med. 2015; 45:58-65.

[3] Velikyan I. Continued rapid growth in 68Ga applications: update 2013 to June 2014. J. Label. Compd. Radiopharm. 2015:In Press.

[4] Rosch F. Past, present and future of 68Ge/68Ga generators. Appl. Radiat. Isot. 2013; 76:24-30.

[5] Sanchez-Crespo A. Comparison of Gallium-68 and Fluorine-18 imaging characteristics in positron emission tomography. Appl. Radiat. Isot. 2013; 76:55-62.

[6] Velikyan I. Prospective of (68)Ga-radiopharmaceutical development. Theranostics 2013; 4:47-80.

[7] Velikyan I. The diversity of (68)Ga-based imaging agents. Recent Results Cancer Res. 2013; 194:101-31.

[8] Price E W and Orvig C. Matching chelators to radiometals for radiopharmaceuticals. Chem. Soc. Rev. 2014; 43:260-90.

[9] Smith D L, Breeman W A, and Sims-Mourtada J. The untapped potential of Gallium 68-PET: the next wave of (6)(8)Ga-agents. Appl. Radiat. Isot. 2013; 76:14-23.

[10] Nedrow J R, White A G, Modi J, Nguyen K, Chang A J, and Anderson C J. Positron emission tomographic imaging of copper 64- and gallium 68-labeled chelator conjugates of the somatostatin agonist tyr3-octreotate. Mol. Imaging 2014; 13:1-13.

[11] Banerjee S R and Pomper M G. Clinical applications of Gallium-68. Appl. Radiat. Isot. 2013; 76:2-13.

[12] Manzoni L, Belvisi L, Arosio D, Bartolomeo M P, Bianchi A, Brioschi C, et al. Synthesis of Gd and (68)Ga complexes in conjugation with a conformationally optimized RGD sequence as potential MRI and PET tumor-imaging probes. ChemMedChem 2012; 7:1084-93.

[13] Morgat C, Hindie E, Mishra A K, Allard M, and Fernandez P. Gallium-68: chemistry and radiolabeled peptides exploring different oncogenic pathways. Cancer Biother. Radiopharm. 2013; 28:85-97.

[14] Sandstrom M, Velikyan I, Garske-Roman U, Sorensen J, Eriksson B, Granberg D, et al. Comparative biodistribution and radiation dosimetry of 68Ga-DOTATOC and 68Ga-DOTATATE in patients with neuroendocrine tumors. J. Nucl. Med. 2013; 54:1755-9.

[15] Velikyan I, Sundin A, Sorensen J, Lubberink M, Sandstrom M, Garske-Roman U, et al. Quantitative and qualitative intrapatient comparison of 68Ga-DOTATOC and 68Ga-DOTATATE: net uptake rate for accurate quantification. J. Nucl. Med. 2014; 55:204-10.

[16] Stasiuk G J and Long N J. The ubiquitous DOTA and its derivatives: the impact of 1,4,7,10-tetraazacyclododecane-1,4,7,10-tetraacetic acid on biomedical imaging. Chem. Commun. (Camb.) 2013; 49:2732-46.

[17] De Leon-Rodriguez L M and Kovacs Z. The synthesis and chelation chemistry of DOTA-peptide conjugates. Bioconjug. Chem. 2008; 19:391-402.

[18] Chappell L L, Ma D, Milenic D E, Garmestani K, Venditto V, Beitzel M P, et al. Synthesis and evaluation of novel bifunctional chelating agents based on 1,4,7,10-tetraazacyclododecane-N,N',N'',N'''-tetraacetic acid for radiolabeling proteins. Nucl. Med. Biol. 2003; 30:581-95.

[19] Mjos K D and Orvig C. Metallodrugs in medicinal inorganic chemistry. Chem. Rev. 2014; 114:4540-63.

[20] Holub J, Meckel M, Kubicek V, Rosch F, and Hermann P. Gallium(III) complexes of NOTA-bis (phosphonate) conjugates as PET radiotracers for bone imaging. Contrast Media Mol. Imaging 2015; 10:122-34.

[21] Meckel M, Fellner M, Thieme N, Bergmann R, Kubicek V, and Rosch F. In vivo comparison of DOTA based 68Ga-labelled bisphosphonates for bone imaging in non-tumour models. Nucl. Med. Biol. 2013; 40:823-30.

[22] Velikyan I, Maecke H, and Langstrom B. Convenient Preparation of (68)Ga-Based PET-Radiopharmaceuticals at Room Temperature. Bioconjugate Chem. 2008; 19:569-73.

[23] Eisenwiener K P, Prata M I, Buschmann I, Zhang H W, Santos A C, Wenger S, et al. NODAGATOC, a new chelator-coupled somatostatin analogue labeled with [67/68Ga] and [111In] for SPECT, PET, and targeted therapeutic applications of somatostatin receptor (hsst2) expressing tumors. Bioconjug. Chem. 2002; 13:530-41.

[24] Pohle K, Notni J, Bussemer J, Kessler H, Schwaiger M, and Beer A J. 68Ga-NODAGA-RGD is a suitable substitute for (18)F-Galacto-RGD and can be produced with high specific activity in a cGMP/GRP compliant automated process. Nucl. Med. Biol. 2012; 39:777-84.

[25] Oxboel J, Brandt-Larsen M, Schjoeth-Eskesen C, Myschetzky R, El-Ali H H, Madsen J, et al. Comparison of two new angiogenesis PET tracers 68Ga-NODAGA-E[c(RGDyK)]2 and (64)Cu-NODAGA-E[c(RGDyK)]2; in vivo imaging studies in human xenograft tumors. Nucl. Med. Biol. 2014; 41:259-67.

[26] Fani M, Tamma M L, Nicolas G P, Lasri E, Medina C, Raynal I, et al. In vivo imaging of folate receptor positive tumor xenografts using novel 68Ga-NODAGA-folate conjugates. Mol. Pharm. 2012; 9:1136-45.

[27] Velikyan I, Maecke H, and Langstrom B. Convenient preparation of 68Ga-based PET-radiopharmaceuticals at room temperature. Bioconjug. Chem. 2008; 19:569-73.

[28] Knetsch P A, Petrik M, Griessinger C M, Rangger C, Fani M, Kesenheimer C, et al. [68Ga]NODAGA-RGD for imaging alphavbeta3 integrin expression. Eur. J. Nucl. Med. Mol. Imaging 2011; 38:1303-12.

[29] Ogawa K, Takai K, Kanbara H, Kiwada T, Kitamura Y, Shiba K, et al. Preparation and evaluation of a radiogallium complex-conjugated bisphosphonate as a bone scintigraphy agent. Nucl. Med. Biol. 2011; 38:631-6.

[30] Fellner M, Baum R P, Kubicek V, Hermann P, Lukes I, Prasad V, et al. PET/CT imaging of osteoblastic bone metastases with (68)Ga-bisphosphonates: first human study. Eur. J. Nucl. Med. Mol. Imaging 2010; 37:834.

[31] Suzuki K, Satake M, Suwada J, Oshikiri S, Ashino H, Dozono H, et al. Synthesis and evaluation of a novel 68Ga-chelate-conjugated bisphosphonate as a bone-seeking agent for PET imaging. Nucl. Med. Biol. 2011; 38:1011-8.

[32] Fellner M, Biesalski B, Bausbacher N, Kubicek V, Hermann P, Rosch F, et al. (68)Ga-BPAMD: PET-imaging of bone metastases with a generator based positron emitter. Nucl. Med. Biol. 2012; 39:993-9.

[33] Toegel S, Wadsak W, Mien L K, Viernstein H, Kluger R, Eidherr H, et al. Preparation and pre-vivo evaluation of no-carrier-added, carrier-added and cross-complexed [(68)Ga]-EDTMP formulations. Eur. J. Pharm. Biopharm. 2008; 68:406-12.

[34] Seemann J, Eppard E, Waldron B P, Ross T L, and Roesch F. Cation exchange-based post-processing of (68) Ga-eluate: a comparison of three solvent systems for labelling of DOTATOC, NO2AP(BP) and DATA(m.). Appl. Radiat. Isot. 2015; 98:54-9.

[35] Notni J, Simecek J, and Wester H J. Phosphinic acid functionalized polyazacycloalkane chelators for radiodiagnostics and radiotherapeutics: unique characteristics and applications. ChemMedChem 2014; 9:1107-15.

[36] Simecek J, Notni J, Kapp T G, Kessler H, and Wester H J. Benefits of NOPO as chelator in gallium-68 peptides, exemplified by preclinical characterization of (68)Ga-NOPO-c(RGDfK). Mol. Pharm. 2014; 11:1687-95.

[37] Simecek J, Zemek O, Hermann P, Notni J, and Wester H J. Tailored Gallium(III) Chelator NOPO: Synthesis, Characterization, Bioconjugation, and Application in Preclinical Ga-68-PET Imaging. Mol. Pharm. 2013.

[38] Huang S S, Wang X, Zhang Y, Doke A, DiFilippo F P, and Heston W D. Improving the biodistribution of PSMA-targeting tracers with a highly negatively charged linker. Prostate 2014; 74:702-13.

[39] Banerjee S R, Pullambhatla M, Byun Y, Nimmagadda S, Green G, Fox J J, et al. 68Ga-labeled inhibitors of prostate-specific membrane antigen (PSMA) for imaging prostate cancer. J. Med. Chem. 2010; 53:5333-41.

[40] Simecek J, Hermann P, Havlickova J, Herdtweck E, Kapp T G, Engelbogen N, et al. A cyclen-based tetraphosphinate chelator for the preparation of radiolabeled tetrameric bioconjugates. Chemistry 2013; 19:7748-57.

[41] Simecek J, Hermann P, Wester H J, and Notni J. How is (68)Ga labeling of macrocyclic chelators influenced by metal ion contaminants in (68)Ge/(68)Ga generator eluates? ChemMedChem 2013; 8:95-103.

[42] Ramogida C F, Cawthray J F, Boros E, Ferreira C L, Patrick B O, Adam M J, et al. H2CHXdedpa and H4CHXoctapa-Chiral Acyclic Chelating Ligands for (67/68)Ga and (111)In Radiopharmaceuticals. Inorg. Chem. 2015; 54:2017-31.

[43] Baur B, Solbach C, Andreolli E, Winter G, Machulla H J, and Reske S N. Synthesis, Radiolabelling and In Vitro Characterization of the Gallium-68-, Yttrium-90- and Lutetium-177-Labelled PSMA Ligand, CHX-A"-DTPA-DUPA-Pep. Pharmaceuticals (Basel) 2014; 7:517-29.

[44] Davis M I, Bennett M J, Thomas L M, and Bjorkman P J. Crystal structure of prostate-specific membrane antigen, a tumor marker and peptidase. Proc. Natl. Acad. Sci. U.S.A 2005; 102:5981-6.

[45] Jadvar H. Molecular imaging of prostate cancer with PET. J. Nucl. Med. 2013; 54:1685-8.

[46] Akhtar N H, Pail O, Saran A, Tyrell L, and Tagawa S T. Prostate-Specific Membrane Antigen-Based Therapeutics. Advances in Urology 2012; 2012:9.

[47] Ristau B T, O'Keefe D S, and Bacich D J. The prostate-specific membrane antigen: lessons and current clinical implications from 20 years of research. Urol Oncol 2014; 32:272-9.

[48] Osborne J R, Akhtar N H, Vallabhajosula S, Anand A, Deh K, and Tagawa S T. Prostate-specific membrane antigen-based imaging. Urol Oncol 2013; 31:144-54.

[49] Schafer M, Bauder-Wust U, Leotta K, Zoller F, Mier W, Haberkorn U, et al. A dimerized urea-based inhibitor of the prostate-specific membrane antigen for 68Ga-PET imaging of prostate cancer. EJNMMI Res 2012; 2:23.

[50] Eder M, Neels O, Muller M, Bauder-Wust U, Remde Y, Schafer M, et al. Novel Preclinical and Radiopharmaceutical Aspects of [68Ga]Ga-PSMA-HBED-CC: A New PET Tracer for Imaging of Prostate Cancer. Pharmaceuticals (Basel) 2014; 7:779-96.

[51] Eder M, Schafer M, Bauder-Wust U, Hull W E, Wangler C, Mier W, et al. 68Ga-complex lipophilicity and the targeting property of a urea-based PSMA inhibitor for PET imaging. Bioconjug. Chem. 2012; 23:688-97.

[52] Afshar-Oromieh A, Avtzi E, Giesel F L, Holland-Letz T, Linhart H G, Eder M, et al. The diagnostic value of PET/CT imaging with the 68Ga-labelled PSMA ligand HBED-CC in the diagnosis of recurrent prostate cancer. Eur. J. Nucl. Med. Mol. Imaging 2014:Ahead of Print.

[53] Afshar-Oromieh A, Haberkorn U, Schlemmer H P, Fenchel M, Eder M, Eisenhut M, et al. Comparison of PET/CT and PET/MRI hybrid systems using a 68Ga-labelled PSMA ligand for the diagnosis of recurrent prostate cancer: initial experience. Eur. J. Nucl. Med. Mol. Imaging 2014; 41:887-97.

[54] Maurer T, Beer A J, Wester H J, Kubler H, Schwaiger M, and Eiber M. Positron emission tomography/magnetic resonance imaging with 68Gallium-labeled ligand of prostate-specific membrane antigen: promising novel option in prostate cancer imaging? Int. J. Urol. 2014; 21:1286-8.

[55] Chakraborty P S, Tripathi M, Agarwal K K, Kumar R, Vijay M K, and Bal C. Metastatic Poorly Differentiated Prostatic Carcinoma With Neuroendocrine Differentiation: Negative on 68Ga-PSMA PET/CT. Clin. Nucl. Med. 2015; 40:e163-6.

[56] Eiber M, Nekolla S G, Maurer T, Weirich G, Wester H J, and Schwaiger M. Ga-PSMA PET/MR with multimodality image analysis for primary prostate cancer. Abdom. Imaging 2014.

[57] Afshar-Oromieh A, Avtzi E, Giesel F L, Holland-Letz T, Linhart H G, Eder M, et al. The diagnostic value of PET/CT imaging with the (68)Ga-labelled PSMA ligand HBED-CC in the diagnosis of recurrent prostate cancer. Eur. J. Nucl. Med. Mol. Imaging 2015; 42:197-209.

[58] Maurer T, Weirich G, Schottelius M, Weineisen M, Frisch B, Okur A, et al. Prostate-specific Membrane Antigen-radioguided Surgery for Metastatic Lymph Nodes in Prostate Cancer. Eur. Urol. 2015.

[59] Malik N, Baur B, Winter G, Reske S N, Beer A J, and Solbach C. Radiofluorination of PSMA-HBED via AlF Chelation and Biological Evaluations In Vitro. Mol. Imaging Biol. 2015.

[60] Eiber M, Maurer T, Souvatzoglou M, Beer A J, Ruffani A, Haller B, et al. Evaluation of Hybrid 68Ga-PSMA Ligand PET/CT in 248 Patients with Biochemical Recurrence After Radical Prostatectomy. J. Nucl. Med. 2015; 56:668-74.

[61] Clarke E T and Martell A E. 19. Stabilities of trivalent metal ion complexes of the tetraacetate derivatives of 12-, 13- and 14-membered tetraazamacrocycles. Inorg. Chim. Acta 1991; 190:37-46.

[62] Broan C J, Cox J P L, Craig A S, Kataky R, Parker D, Harrison A, et al. Structure and solution stability of indium and gallium complexes of 1,4,7,-triazacyclononanetriacetate and yttrium complexes of 1,4,7,10-tetraazacyclododecanetetraacetate and related ligands: kinetically stable complexes for use in imaging and radioimmunotherapy. X-ray molecular structure of the indium and gallium complexes of 1,4,7,-triazacyclononane-1,4,7-triacetic acid J. Chem. Soc., Perkin Trans. 1991; 21:87-99.

[63] Motekaitis R J, Rogers B E, Reichert D E, Martell A E, and Welch M J. Stability and Structure of Activated Macrocycles. Ligands with Biological Applications. Inorg. Chem. 1996; 35:3821-7.

[64] Sun Y, Anderson C J, Pajeau T S, Reichert D E, Hancock R D, Motekaitis R, et al. Indium (III) and gallium (III) complexes of bis(aminoethanethiol) ligands with different denticities: stabilities, molecular modeling, and in vivo behavior. J. Med. Chem. 1996; 39:458-70.

[65] Huigen Y M, Tji T G, Gelsema W J, and de Ligny C L. The binding of $^{99m}$Tc(Sn)-MDP complexes to human serum albumin and other blood proteins determined with gel chromatography and ultrafiltration. Int. J. Rad. Appl. Instrum. [A] 1989; 40:629-35.

What is claimed is:

1. A compound according to Formula I:

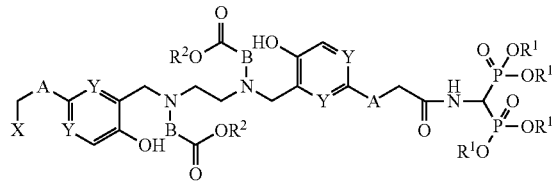

Formula I or a pharmaceutically acceptable salt thereof,
wherein

A is a divalent linking moiety comprising 1 to 10 carbon atoms in a chain, a ring, or a combination thereof, wherein at least one carbon atom is optionally replaced with O, —$NR^9$—, or —C(O)—;

B is $CR^3R^4$;

X is selected from the group consisting of:

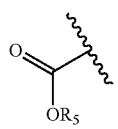

$X_1$

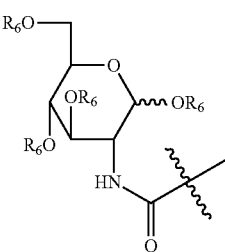

$X_2$

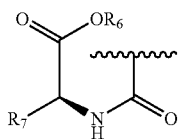

$X_3$

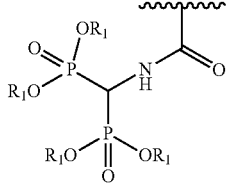

$X_4$

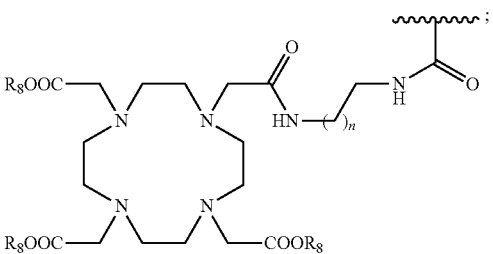

$X_5$ $X_6$ n is from 1 to 8;

Y is independently CH or N;

$R^1$ is hydrogen or a ($C_1$-$C_6$) alkyl group;

$R^2$, $R^5$, and $R^8$ are independently hydrogen or a carboxylic acid protecting group;

$R^3$ and $R^4$ are independently hydrogen, a ($C_1$-$C_{10}$) alkyl group, an ethylene glycolyl group, or a propylene glycolyl group;

$R^6$ is hydrogen or a ($C_1$-$C_6$) acyl group; and $R^7$ is the α-position substituent of an amino acid, and $R^9$ is independently selected from the group consisting of H, alkyl, cycloalkyl, heterocycloalkyl, aryl, alkylaryl, arylalkyl and heteroaryl.

2. The compound of claim 1, wherein

A is $(CH_2)_m$, wherein m is 0, 1, 2, or 3;

$R^1$ is Et;

X is selected from the group consisting of:

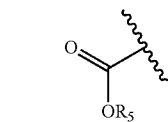

$X_1$

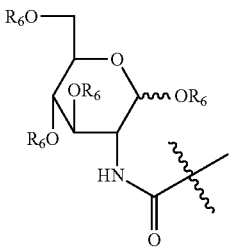

$X_2$

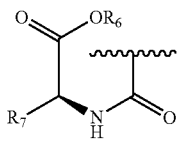

$X_3$

-continued

X4
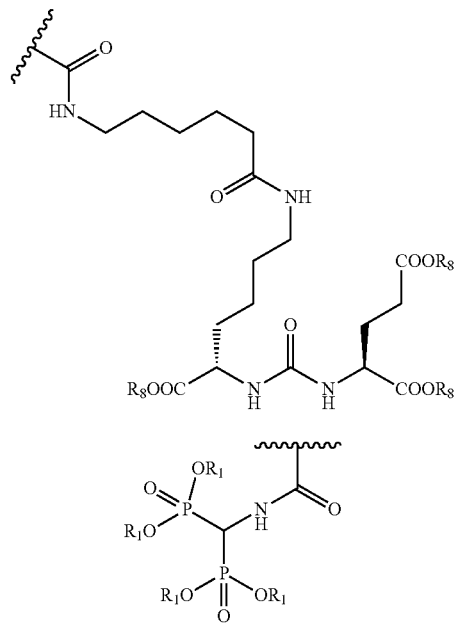

X5
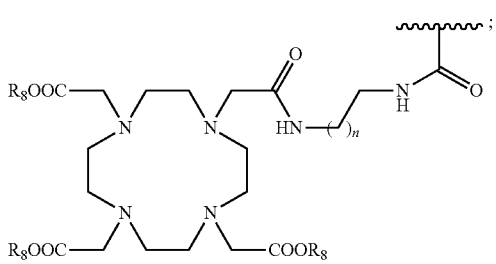

X6
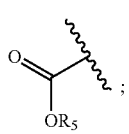... ;

n is from 1 to 8;
R², R⁵, and R⁸ are t-Bu;
R⁶ is AcO; and
B, Y, R³, R⁴, and R⁷ are defined as in claim 1;
or a pharmaceutically acceptable salt thereof.

3. The compound of claim 1, wherein
A is CH₂;
Y is CH;
R⁷ is selected from the group consisting of hydrogen, methyl, —CH₂COOR⁸, and —(CH₂)₂COOR⁸;
R¹, R², R³, R⁴, R⁵, R⁶, and R⁸ are hydrogen;
or a pharmaceutically acceptable salt thereof.

4. The compound of claim 1, wherein
X is

X1
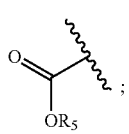

or a pharmaceutically acceptable salt thereof.

5. The compound of claim 1, wherein
X is

X2
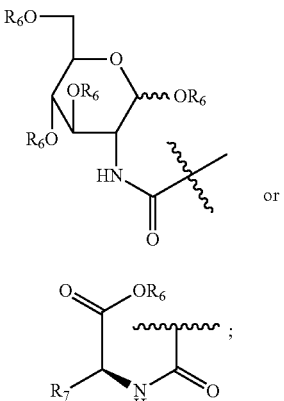

or

X3 or a pharmaceutically acceptable salt thereof.

6. The compound of claim 1, wherein

X4

or a pharmaceutically acceptable salt thereof.

7. The compound of claim 1, wherein
X is

X5
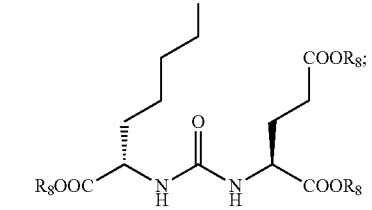

or a pharmaceutically acceptable salt thereof.

8. The compound of claim 1, wherein X is

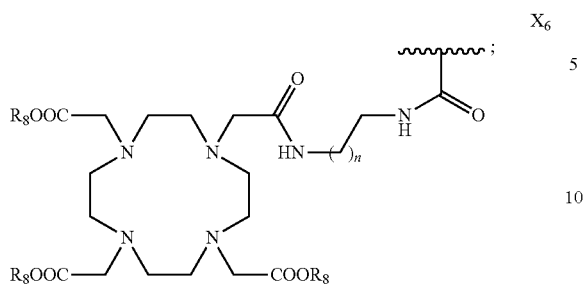

and n is from 1 to 8;
or a pharmaceutically acceptable salt thereof.

9. The compound of claim 1, having the structure:

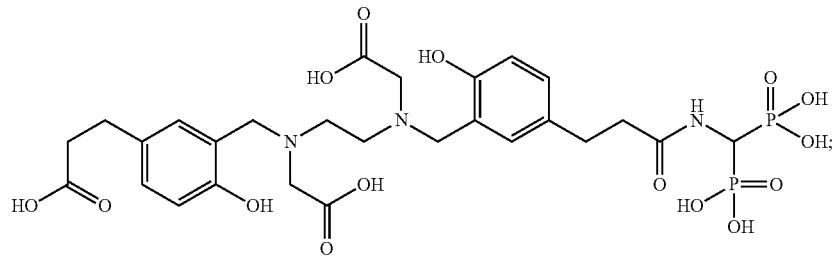 [SMILES: O=C(O)CCc1ccc(O)c(CN(CCN(CC(=O)O)Cc2cc(CCC(=O)NC(P(=O)(O)O)P(=O)(O)O)ccc2O)CC(=O)O)c1]

or a pharmaceutically acceptable salt thereof.

10. The compound of claim 1, having the structure:

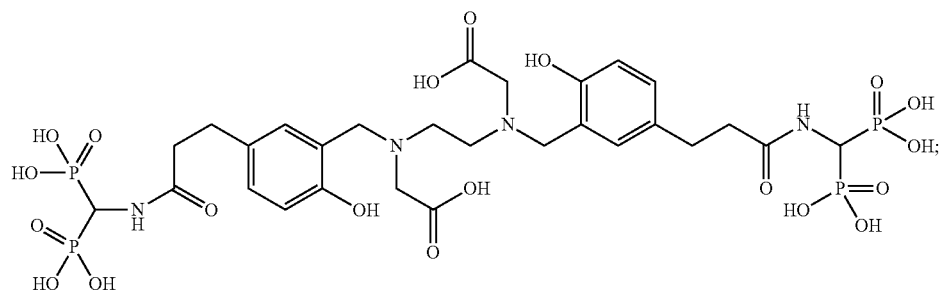 [SMILES: O=C(O)CN(CCN(CC(=O)O)Cc1cc(CCC(=O)NC(P(=O)(O)O)P(=O)(O)O)ccc1O)Cc1cc(CCC(=O)NC(P(=O)(O)O)P(=O)(O)O)ccc1O]

or a pharmaceutically acceptable salt thereof.

11. The compound of claim 1, having the structure:

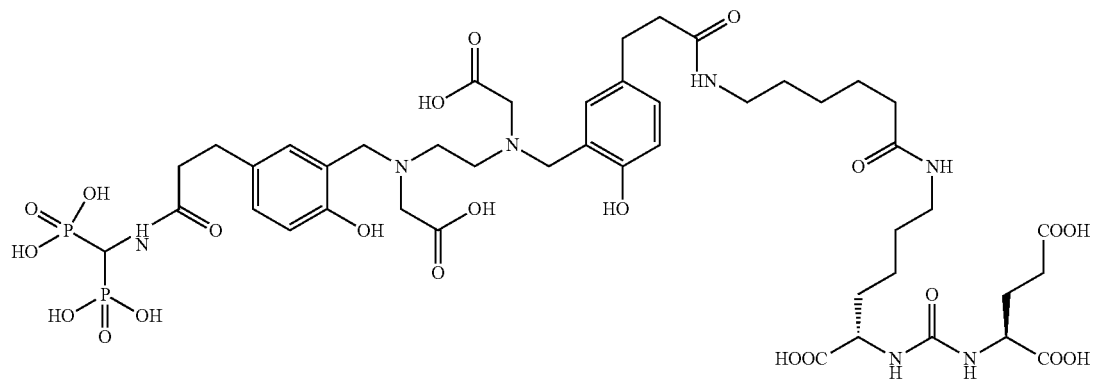 [SMILES: O=C(O)CC[C@H](NC(=O)N[C@@H](CCCCNC(=O)CCCCCNC(=O)CCc1ccc(O)c(CN(CCN(CC(=O)O)Cc2cc(CCC(=O)NC(P(=O)(O)O)P(=O)(O)O)ccc2O)CC(=O)O)c1)C(=O)O)C(=O)O]

or a pharmaceutically acceptable salt thereof.

12. A complex comprising a compound of claim 1 chelated to a metal M, or a pharmaceutically acceptable salt thereof, wherein M is selected from the group consisting of $^{44}$Sc, $^{47}$Sc, $^{203}$Pb, $^{67}$Ga, $^{68}$Ga, $^{72}$As, $^{111}$In, $^{90}$Y, $^{97}$Ru, $^{62}$Cu, $^{64}$Cu, $^{52}$Fe, $^{52m}$Mn, $^{140}$La, $^{175}$Yb, $^{153}$Sm, $^{166}$Ho, $^{149}$Pm, $^{177}$Lu, $^{142}$Pr, $^{159}$Gd, $^{213}$Bi, $^{67}$Cu, $^{111}$Ag, $^{199}$Au, $^{161}$Tb, and $^{51}$Cr.

13. The complex of claim 12, having the structure according to Formula II:

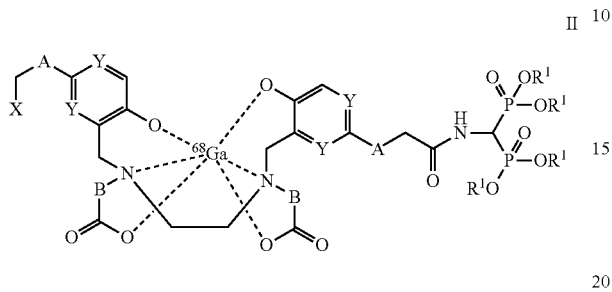

II or a pharmaceutically acceptable salt thereof,
wherein
A is a divalent linking moiety comprising 1 to 10 carbon atoms in a chain, a ring, or a combination thereof, wherein at least one carbon atom is optionally replaced with O, —NR$^9$—, or —C(O)—;
B is CR$^3$R$^4$;
X is selected from the group consisting of:

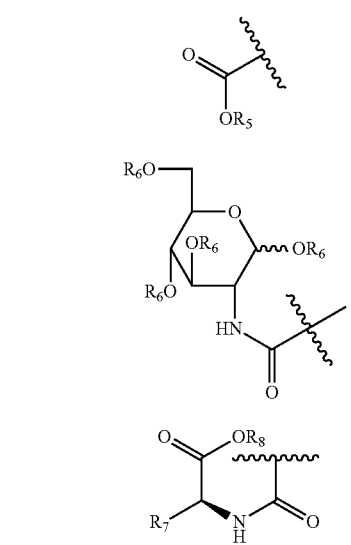

X$_1$

X$_2$

X$_3$

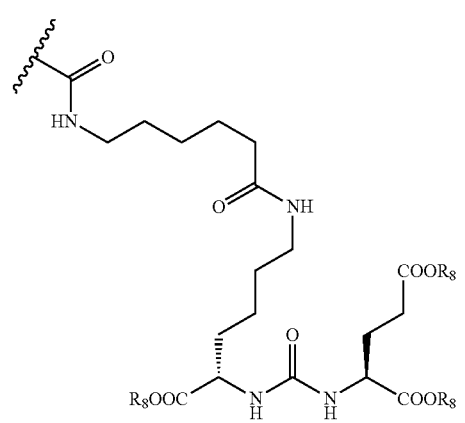

X$_4$

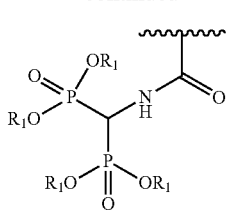

X$_5$

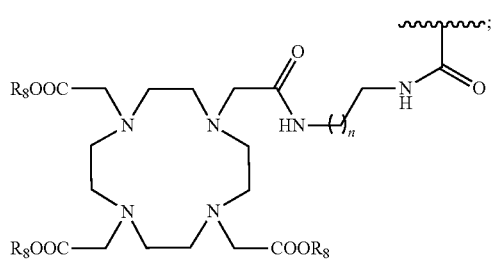

X$_6$ n is from 1 to 8;
Y is independently CH or N;
R$^3$ and R$^4$ are independently hydrogen, a (C$_1$-C$_{10}$) alkyl group, an ethylene glycolyl group, or a propylene glycolyl group;
R$^5$, and R$^8$ are independently hydrogen or a carboxylic acid protecting group;
R$^6$ is a (C$_1$-C$_6$) acyl group;
R$^7$ is the α-position substituent of an amino acid;
R$^9$ is independently selected from the group consisting of H, alkyl, cycloalkyl, heterocycloalkyl, aryl, alkylaryl, arylalkyl and heteroaryl; and
M is a metal selected from the group consisting of $^{44}$Sc, $^{47}$Sc, $^{203}$Pb, $^{67}$Ga, $^{68}$Ga, $^{72}$As, $^{111}$In, $^{90}$Y, $^{97}$Ru, $^{62}$Cu, $^{64}$Cu, $^{52}$Fe, $^{52m}$Mn, $^{140}$La, $^{175}$Yb, $^{153}$Sm, $^{166}$Ho, $^{149}$Pm, $^{177}$Lu, $^{142}$Pr, $^{159}$Gd, $^{213}$Bi, $^{67}$Cu, $^{111}$Ag, $^{199}$Au, $^{161}$Tb, and $^{51}$Cr.

14. The complex of claim 13, wherein
A is (CH$_2$)$_m$, wherein m is 0, 1, 2, or 3;
X is selected from the group consisting of:

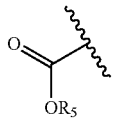

X$_1$

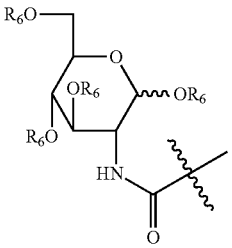

X$_2$

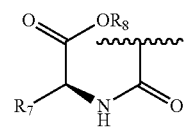

X$_3$

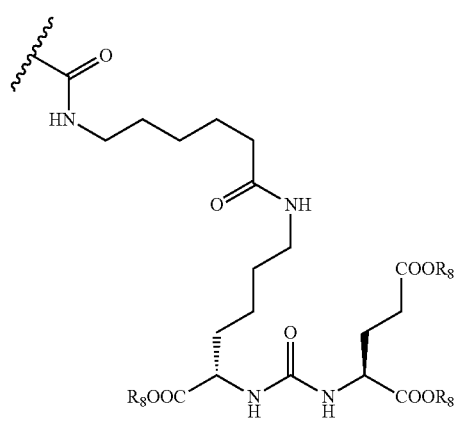

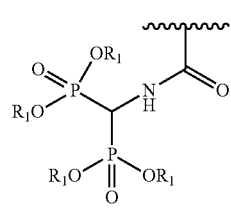

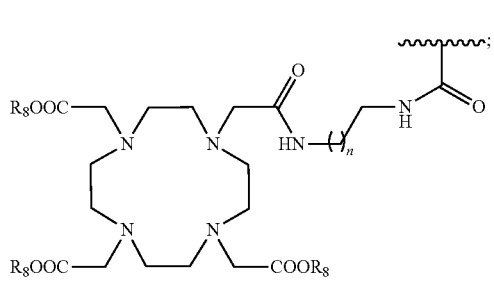

n, Y, $R^3$, $R^4$, $R^5$, $R^6$, $R^7$, and $R^8$ are defined as in claim 13.

15. The complex of claim 13, wherein
A is $CH_2$;
Y is CH;
$R^7$ is selected from the group consisting of hydrogen, methyl, —$CH_2COOR^8$, and —$(CH_2)_2COOR^8$;
$R^3$, $R^4$, $R^5$, $R^6$, and $R^8$ are hydrogen.

16. The complex of claim 13, wherein X is

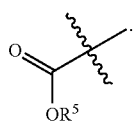

17. The complex of claim 13, wherein X is

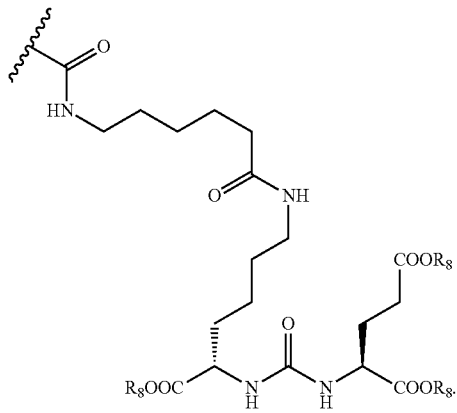

18. The complex of claim 13, wherein X is

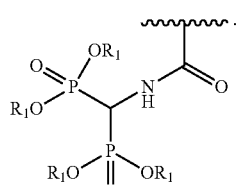

19. The complex of claim 13, wherein X is

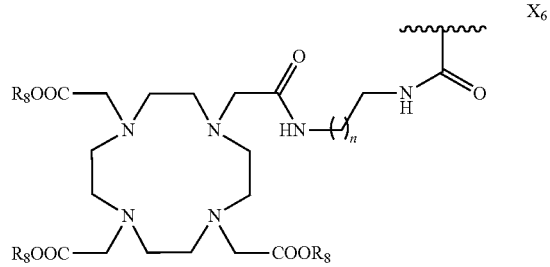

and n is from 1 to 8.

20. The complex of claim 13, having the structure:
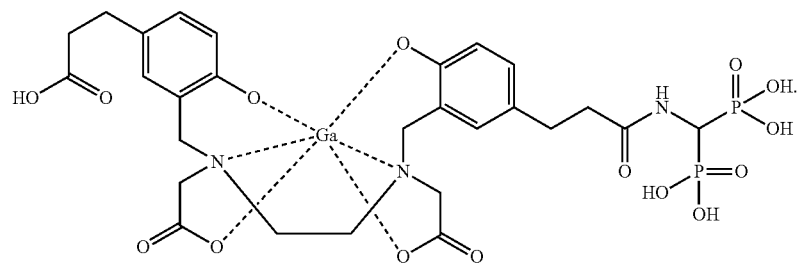
21. The complex of claim 13, having the structure:
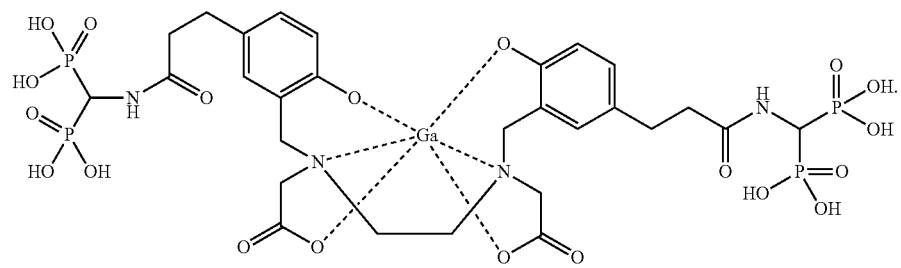
22. The complex of claim 13, having the structure:
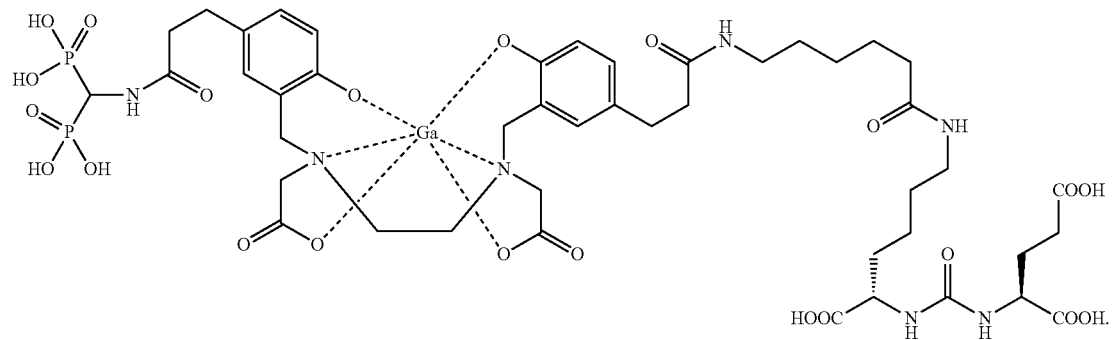
23. The complex of claim 13, having the structure:
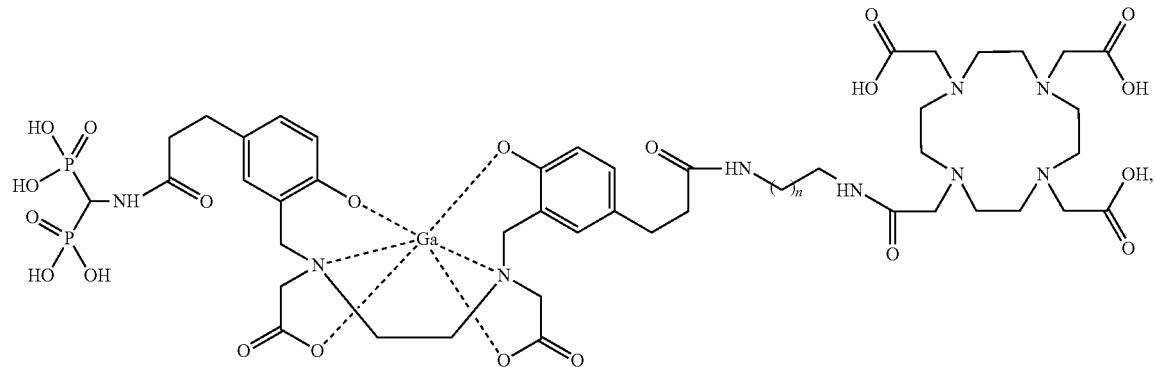
wherein n is from 1 to 8.

24. The complex of claim 12, having the structure:

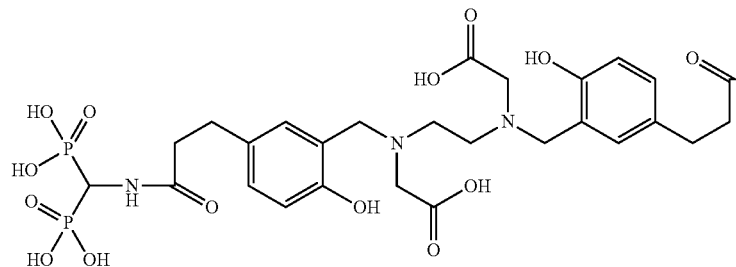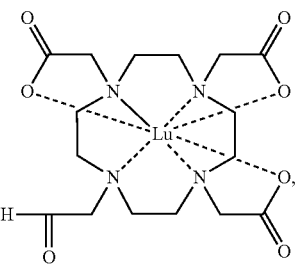

wherein n is from 1 to 8.

25. A pharmaceutical composition comprising a pharmaceutically acceptable carrier and the compound or complex according to claim 1 or a pharmaceutically acceptable salt thereof.

26. A method of in vivo imaging comprising administering an effective amount of the complex according to claim 12 to a subject, and detecting the pattern of radioactivity of the compound in said subject.

27. A method of treating one or more bone tumors in a subject, comprising administering an effective amount of the complex of claim 12, wherein X is

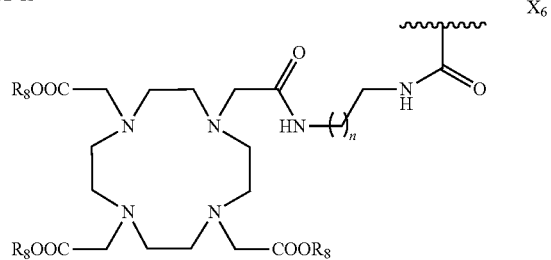

and n is from 1 to 8.

28. A kit comprising a sterile container containing an effective amount of the compound of claim 1 or a pharmaceutically acceptable salt thereof, and instructions for therapeutic use.

* * * * *